(12) United States Patent
Malcolm

(10) Patent No.: US 7,896,017 B2
(45) Date of Patent: Mar. 1, 2011

(54) MEDICAL FLUID DELIVERY SYSTEM AND METHOD RELATING TO THE SAME

(75) Inventor: David R. Malcolm, Parker, CO (US)

(73) Assignee: StnDrd Infusion Corp., Parker, CO (US)

( * ) Notice: Subject to any disclaimer, the term of this patent is extended or adjusted under 35 U.S.C. 154(b) by 0 days.

(21) Appl. No.: 11/952,623

(22) Filed: Dec. 7, 2007

(65) Prior Publication Data

US 2008/0086088 A1    Apr. 10, 2008

Related U.S. Application Data

(63) Continuation of application No. 11/050,031, filed on Feb. 2, 2005, now Pat. No. 7,367,358, which is a continuation-in-part of application No. PCT/US2004/023799, filed on Jul. 23, 2004.

(60) Provisional application No. 60/489,401, filed on Jul. 23, 2003.

(51) Int. Cl.
    *F04B 53/00*    (2006.01)
(52) U.S. Cl. .................. 137/1; 137/636; 137/636.1; 137/595; 251/7; 251/9; 604/34; 417/442
(58) Field of Classification Search .............. 137/1, 137/636, 636.1, 595; 251/7, 9, 6; 604/34; 417/442
See application file for complete search history.

(56) References Cited

U.S. PATENT DOCUMENTS

| 3,698,681 A | 10/1972 | Lacey |
| 3,734,133 A | 5/1973 | Little et al. |
| 3,823,724 A | 7/1974 | Davis |
| 3,841,348 A | 10/1974 | O'Neill |
| 3,850,407 A | 11/1974 | Sekera, Jr. |
| 3,927,436 A | 12/1975 | Inoue et al. |
| 3,938,543 A | 2/1976 | Sorenson |
| 3,942,228 A | 3/1976 | Buckman et al. |
| 3,963,213 A | 6/1976 | Brattberg |
| 3,988,001 A | 10/1976 | Kankaras |
| 3,991,974 A | 11/1976 | Bonafous |

(Continued)

FOREIGN PATENT DOCUMENTS

WO    WO 2005/011082    2/2005

OTHER PUBLICATIONS

International Search Report, Form PCT/ISA210, U.S. Patent and Trademark Office action as International Searching Authority, dated Mar. 6, 2006, 2 pages.

(Continued)

*Primary Examiner*—Kevin L Lee
(74) *Attorney, Agent, or Firm*—Larson & Anderson, LLC

(57) ABSTRACT

A medical fluid delivery system for the use in the delivery of medical fluids. The medical fluid delivery system may include a pumping system, a disposable medical fluid line set and a valve operating system. The disposable tubing line set may include valves adapted to interface with the valve operating system. The valve operating system may be adapted to operate only selected valves using a single drive means. The pumping system may be operated over a wide range of medical fluid delivery rates by employing a bi-directional drive member and a transmission interfaced with the drive member and a pump.

47 Claims, 24 Drawing Sheets

U.S. PATENT DOCUMENTS

| | | |
|---|---|---|
| 4,000,662 A | 1/1977 | Wolfe |
| 4,044,996 A | 8/1977 | Kodaira |
| 4,061,142 A | 12/1977 | Tuttle |
| 4,063,706 A | 12/1977 | Osborne, Sr. |
| 4,084,786 A | 4/1978 | Walters |
| 4,091,815 A | 5/1978 | Larsen |
| 4,116,217 A | 9/1978 | Speidel |
| 4,144,774 A | 3/1979 | Berlinger, Jr. |
| 4,178,814 A | 12/1979 | Ahlen |
| 4,184,815 A | 1/1980 | Casson et al. |
| 4,186,618 A | 2/1980 | Richards |
| 4,191,214 A | 3/1980 | Holley et al. |
| 4,193,174 A | 3/1980 | Stephens |
| 4,196,634 A | 4/1980 | Hehl |
| 4,224,958 A | 9/1980 | Kaplan et al. |
| 4,227,548 A | 10/1980 | Botnick |
| 4,230,149 A | 10/1980 | Worthen et al. |
| 4,243,063 A | 1/1981 | Parkison |
| 4,247,076 A | 1/1981 | Larkin |
| 4,253,491 A | 3/1981 | Worthen et al. |
| 4,282,775 A | 8/1981 | Van Dest |
| 4,282,902 A | 8/1981 | Haynes |
| 4,323,173 A | 4/1982 | Shannon |
| 4,340,202 A | 7/1982 | Hargraves et al. |
| 4,403,626 A | 9/1983 | Paul, Jr. |
| 4,416,595 A | 11/1983 | Cromie |
| 4,421,296 A | 12/1983 | Stephens |
| 4,445,826 A | 5/1984 | Tarr |
| 4,474,309 A | 10/1984 | Solomon |
| 4,484,599 A | 11/1984 | Hanover et al. |
| 4,495,829 A | 1/1985 | Kemper |
| 4,533,113 A | 8/1985 | Francart, Jr. |
| 4,563,175 A | 1/1986 | LaFond |
| 4,590,998 A | 5/1986 | Hopper |
| 4,596,374 A | 6/1986 | Thompson et al. |
| 4,624,663 A | 11/1986 | Danby et al. |
| 4,638,977 A | 1/1987 | Vonhausen |
| 4,696,671 A | 9/1987 | Epstein et al. |
| 4,697,785 A | 10/1987 | Tuseth |
| 4,757,598 A | 7/1988 | Redman |
| 4,818,186 A | 4/1989 | Pastrone et al. |
| 4,903,944 A | 2/1990 | Butzen et al. |
| 4,944,485 A | 7/1990 | Daoud et al. |
| 4,946,434 A | 8/1990 | Plaisted et al. |
| 4,989,641 A | 2/1991 | Jones et al. |
| 5,083,741 A | 1/1992 | Sancoff |
| 5,083,990 A | 1/1992 | Rahm |
| 5,087,018 A | 2/1992 | Blase et al. |
| 5,152,497 A | 10/1992 | Bissell |
| 5,171,301 A | 12/1992 | Vanderveen |
| 5,172,725 A | 12/1992 | Kitagawa |
| 5,176,593 A | 1/1993 | Yasui et al. |
| 5,190,071 A | 3/1993 | Sule |
| 5,199,604 A | 4/1993 | Palmer et al. |
| 5,267,585 A | 12/1993 | Jones et al. |
| 5,267,964 A | 12/1993 | Karg |
| 5,297,773 A | 3/1994 | Collins et al. |
| 5,311,908 A * | 5/1994 | Barone et al. .................. 251/7 |
| 5,320,503 A | 6/1994 | Davis |
| 5,330,000 A | 7/1994 | Givens et al. |
| 5,347,992 A | 9/1994 | Pearlman et al. |
| 5,391,353 A | 2/1995 | Graffunder |
| 5,402,823 A | 4/1995 | Cole |
| 5,405,331 A | 4/1995 | Behnke et al. |
| 5,413,566 A | 5/1995 | Sevrain et al. |
| 5,419,684 A | 5/1995 | Struble et al. |
| 5,466,228 A | 11/1995 | Evans |
| 5,472,420 A | 12/1995 | Campbell |
| 5,489,013 A | 2/1996 | Buuck et al. |
| 5,522,798 A | 6/1996 | Johnson et al. |
| 5,575,631 A | 11/1996 | Jester |
| 5,613,663 A | 3/1997 | Schmidt et al. |
| 5,620,025 A | 4/1997 | Lewin |
| 5,630,710 A | 5/1997 | Tune et al. |
| 5,658,133 A | 8/1997 | Anderson et al. |
| 5,685,844 A | 11/1997 | Marttila |
| 5,687,764 A | 11/1997 | Tanaka et al. |
| 5,699,821 A | 12/1997 | Paradis |
| 5,712,548 A | 1/1998 | Tice et al. |
| 5,723,918 A | 3/1998 | Schilling et al. |
| 5,735,175 A | 4/1998 | Forsyth |
| 5,746,251 A | 5/1998 | Bullard |
| 5,779,016 A | 7/1998 | Kawasaki et al. |
| 5,819,345 A | 10/1998 | Basgall |
| 5,840,058 A | 11/1998 | Ammann et al. |
| 5,845,755 A | 12/1998 | Wahl et al. |
| 5,850,906 A | 12/1998 | Dean |
| 5,853,398 A | 12/1998 | Lal et al. |
| 5,865,915 A | 2/1999 | Owen et al. |
| 5,876,298 A | 3/1999 | Kato et al. |
| 5,924,324 A | 7/1999 | Kilker et al. |
| 5,937,980 A | 8/1999 | Dick |
| 6,716,004 B2 * | 4/2004 | Vandlik et al. ............... 137/881 |
| 7,214,210 B2 * | 5/2007 | Kamen et al. ................ 604/131 |

OTHER PUBLICATIONS

Non-Final Office Action mailed May 29, 2009, U.S. Appl. No. 11/952,530, filed Dec. 7, 2007, Applicant: David R. Malcolm, 12 pages.

* cited by examiner

MEDICAL FLUID DELIVERY SYSTEM AND METHOD RELATING TO THE SAME

CROSS-REFERENCE TO RELATED APPLICATIONS

This application is a continuation of prior U.S. patent application Ser. No. 11/050,031 filed Feb. 2, 2005, now U.S. Pat. No. 7,367,358, entitled "MEDICAL FLUID DELIVERY SYSTEM AND METHOD RELATING TO THE SAME", which is a continuation-in-part of PCT Patent Application Serial No. US2004/023799 filed Jul. 23, 2004, entitled "DRIVE MOTOR TRANSMISSION SYSTEM", which claims priority to U.S. Provisional Patent Application Ser. No. 60/489,401 filed Jul. 23, 2003, entitled "ELECTRIC DRIVE MOTOR TRANSMISSION SYSTEM". The above-referenced patent applications are incorporated herein by reference as if their contents were set forth below in full.

FIELD OF THE INVENTION

This invention is generally directed to a drive motor system which operates over a wide range of speeds and torques through a novel arrangement of motion transfer members (e.g., gears and clutches), a bi-directional drive member (e.g., a bi-directional motor), which can be driven bi-directionally, and a transmission. In a particular application, the invention is directed to fluid pumping with a drive motor system that utilizes a bi-directional motor to achieve a range of fluid movement rates and torques. More particularly, the drive motor system is particularly suited for implementation in a medical fluid delivery system and in methods relating to the same.

The invention is further directed to a fluid pumping system with multiple inlet input lines and a mechanism (e.g., a valve operating system) to selectively open input fluid line valves in any sequence to deliver said fluid to a single fluid output line. In particular, the fluid pumping system and valve operating system may be implemented in a medical fluid delivery system, which may comprise a disposable medical fluid line set. In this regard, a valve operating system may be employed to operate valves utilized in a disposable medical fluid line set. The drive motor system, valves and valve operating systems described by the present invention may be particularly adapted for use with an intravenous infusion pump employable in a medical fluid delivery system.

BACKGROUND OF THE INVENTION

Motors are used to provide motive forces for many applications. In some applications, a single device is tasked with both rapid, low precision movement during a first activity, and slow, precisely controlled movement during a second activity. In order to achieve both types of movement, many devices must use two motors, one for the fast movement and another for the slow movement, thus increasing the cost, size and weight of the device. Other options include the use of stepper motors, which are able to develop significant slow motor speed torque and precise rotational control. However, stepper motors have numerous disadvantages, including high cost, the need for relatively complicated control circuitry, large size, large weight and high power requirements.

The disadvantages of presently available motor systems are particularly problematic in medical infusion pump systems. Intravenous infusion therapy is prescribed where it is desirable to administer medications and other fluids directly into the circulatory system of a patient. Medical infusion pumps have typically employed stepper motors to provide rotational motive force, and thus are limited by the disadvantages of a stepper motor as listed above. Further, for many clinical procedures it is desirable to administer several medical fluids to a patient simultaneously, thus requiring multiple independent gravity flow controllers and/or multiple independent electronic pumps. The use of multiple independent controllers or pumps, however, is disadvantageous for many reasons, including: the increased possibility of infection occasioned by multiple IV venipuncture; the increased discomfort to the patient, the considerable labor and time required for administering multiple IVs and setting up multiple controllers/pumps; the increased clutter around the patient; the comparatively high cost of procuring and maintaining several pumps; and the comparatively high cost incurred in maintaining an inventory of tubes required by each of the different pump types.

Past attempts to overcome some of these above-described difficulties have resulted in devices utilizing multiple valves, such as described in U.S. Pat. No. 4,696,671 to Epstein et al. Epstein et al. disclose a sterile, disposable cassette containing fluid input and output lines and chambers, wherein the cassette is inserted into a pumping mechanism such that plungers from the pump mechanism engage and close the valves of the cassette. Thus, Epstein et al. disclose a system where the valves of the cassette are biased to an open state when not engaged by a pump mechanism. This arrangement may result in unintentional fluid flow to a patient when the valve set is mistakenly removed from or incorrectly aligned within the pump unit. The valves of Epstein et al. must also be opened sequentially in order to reach the valve of interest. Therefore, an additional valve and independent motive force for the valve is required to prohibit flow during a period in which the unintended valve is open, such as by using a third motor. In some circumstances, operation of valves in accordance with the teachings of Epstein et al. is not desirable due to the resultant fluid interactions or fluid damage, such as cell damage to blood cells.

SUMMARY OF THE INVENTION

In view of the foregoing, it is an object of the invention to provide a drive motor system that includes a bi-directional drive member (e.g. a bi-directional motor), a first motion transfer member (e.g. a first gear and a first one-way clutch), where the first motion transfer member is in mechanical contact with an output shaft such that when the bi-directional drive member (e.g. bi-directional drive motor) is turned in a first direction, a first output is produced. Also provided in such a drive motor system is a second motion transfer member (e.g. a second gear, a second one-way clutch and at least one additional transmission gear) in mechanical contact with the bi-directional drive member (e.g. motor), and the output shaft such that when the bi-directional drive member (e.g. bi-directional motor) is turned in a second direction, a second output is produced. More particularly, it is an object of the invention to provide a medical fluid delivery system that comprises the above drive motor system.

A further object of the invention is a method of providing a device with a wide range of motor speeds and torques by providing a drive motor system, where the first and second motion transfer members both drive the output shaft in the same one direction, and at varying speeds, in response to the first and second outputs of the bi-directional motor, respectively. More particularly, it is an object of the invention to utilize a medical fluid delivery system that comprises the above drive motor system for delivering medical fluids over a wide range of flow rates.

A further object of the invention is a fluid pump and a method of pumping fluids using a fluid pump, emphasizing a drive motor system and drive method, as described above. Such a fluid pump may employ additional elements of the present invention, including a rotary or linear pump head, a plurality of fluid input lines in fluid connection with a manifold (which may be in fluid connection with a fluid output line), a plurality of pinch valves which may receive the fluid input lines, a valve operating system, a pressure measurement system, a power supply, a computer processor and control system, and a housing adapted to receive such elements. More particularly, it is an object of the invention to provide a medical fluid delivery system that comprises one or more of the above fluid pump, drive motor system, a rotary or linear pump head, a plurality of fluid input lines, a manifold, a fluid output line, a plurality of pinch valves, a valve operating system, a pressure measurement system, a power supply, a computer processor and control system, and/or a housing.

It is a further object of the invention to provide an improved pinch valve, where the improvements include a biasing means for forcing first and second elongated members in at least a first direction about a pivot point to a pinching position (e.g., a normally-closed position). The improvements may further comprise at least one rib and at least one valley. In one approach, the at least one rib and at least one valley are designed to form a portion of a fluid line into a serpentine shape. The pinch valve may further include at least one adaptation that allows the pinch valve to receive or be received by a valve operating system. Such at least one adaptation may be designed to matably receive and engaged another adaptation (e.g., a male-female arrangement), such as with the use of slots or pins. More particularly, it is an object of the invention to provide a medical fluid delivery system that comprises the above pinch valve. In one aspect, a medical fluid line set is arranged with the pinch valve and within the medical fluid delivery system such that when one or more medical fluid delivery line is removed, either intentionally or unintentionally, fluid flow is substantially or completely occluded through the correspondingly removed medical fluid delivery line(s).

It is a further object of the invention to provide a valve operating system and method for opening and closing pinch valves. Such a system may include a central drive member (e.g. a drive motor and a central drive gear in mechanical contact with the output shaft of the motor), a plurality of activation members (e.g. mutilated gears) in mechanical contact with the central drive member, and a plurality of valve interface members (e.g. actuator gears, actuator clutches and valve actuators) in mechanical contact with the valve activation members (e.g. mutilated gears). In one aspect, the valve actuators are adapted to interface with (e.g., matably receive and/or engage) the pinch valves, such that rotation of the valve actuators may cause the pinch valve to at least partially open or close. More particularly, it is an object of the invention to provide a medical fluid delivery system that comprises the above valve operating system.

In conjunction therewith, a medical fluid delivery system is provided which may implement various aspects of the present invention. It is initially noted that such systems may provide for the delivery of a medical fluid to a patient (e.g., a human or animal) or a receptacle. As such, it will be appreciated that whether reference is made to a patient or receptacle in regards to the various aspect, approaches, applications, embodiments and the like described herein, such a reference is equally applicable to either a patient or receptacle, and is not meant to limit such application of the medical fluid delivery system.

In that regard, the medical fluid delivery system may comprise a medical fluid line set comprising a plurality of medical fluid delivery lines received by (e.g., interconnected with) a corresponding plurality of pinch valves. The medical fluid line set may be further interfaced with a valve operating system that enables the selective opening of only certain valves of the plurality of pinch valves. The valve operating system may include a plurality of valve actuators, where each of the valve actuators is adapted to matably receive and engage the valves such that rotation of the valve actuator causes the pinch valve to at least partially open or close.

The valve operating system may further comprise a valve status determination system for determining the positions of each of the valve actuators associated with a plurality of pinch valves, wherein the system may then determine and take an action in accordance with an input thereto. For example, the valve operating system may receive an input relating to changing from delivering a first medical fluid to a patient to delivering a second medical fluid to a patient. In this regard, the valve operating system, in conjunction with the valve status determination system, may be operable to determine which valve actuator(s) is/are actuated and de-actuate such valve actuator(s). Further, the valve operating system may be operable to determine which valve actuator(s) is/are associated with delivery of the second medical fluid and actuate such valve actuator(s). In one aspect, the valve operating system is operable to actuate the valve actuator(s) associated with the delivery of the second medical fluid without actuating any other valve actuator.

In one aspect, an inventive medical fluid delivery system may utilize a single pump (e.g., such as an infusion pump or a compounding pump) in conjunction with the drive motor system to deliver medical fluids over a wide-range of flow rates, which in the context of medical applications is applicable to an infusion pump. In this regard, the medical fluid delivery system may include a pumping system, which may include a drive motor, a bi-directional drive member (e.g., a bi-directional motor and a motor gear), a first motion transfer member (e.g., a first gear and a first one-way clutch) in mechanical contact with the bi-directional drive member and a pump drive member (e.g., an output shaft), where moving the bi-directional drive member in a first direction produces a first output. The first output moves at least a portion of the pump drive member, via the first motion transfer member, in one direction at a first speed. The pumping system may also include a second motion transfer member (e.g., a second gear, a second one-way clutch and at least one additional transmission gear) in mechanical contact with the bi-directional drive member, where moving the bi-directional drive member in a second direction produces a second output. The second output moves at least a portion of the pump drive member, via the second motion transfer member, in the same one direction at a second speed.

In one approach, the bi-directional drive member may be moved at a wide range of speeds (e.g., by changing the supplied current and/or voltage to electric bi-directional drive motor) and/or operated at intermittent times in both the first and second directions, thereby enabling the first and second outputs to vary in response thereto. Such speed variation and/or intermittent pump operation, thus, enables a pump interfaced with such bi-directional drive member to deliver medical fluids over a wide range of flow rates in corresponding relation to the first and second outputs.

As will be appreciated, the first motion transfer members may be sized, and arranged with the bi-directional drive member, such that their corresponding first and second outputs relate to different medical flow rate ranges. In this regard, the bi-directional drive motor may be operable within a predetermined range. In relation thereto, the bi-directional drive member may selectively provide the first and second outputs within first and second predetermined operating ranges, respectively. In one embodiment, the first predetermined operating range corresponds to a first medical fluid delivery rate range, and the second predetermined operating range corresponds to a second medical fluid delivery rate range. In one particular aspect, the first and second medical fluid delivery rate ranges are at least partially non-overlapping. In another aspect, the first and second medical fluid delivery rate ranges are non-overlapping.

Further in this regard, each of the first and second medical fluid delivery rate ranges may have maximum and minimum flow rates associated therewith. In one embodiment, the first medical fluid delivery rate range has a maximum flow rate 2000 ml per minute, more particularly 1000 ml per minute, and a minimum flow rate of 1 ml per minute, more particularly 5 ml per minute, even more particularly 10 ml per minute. In one embodiment, the second medical fluid delivery rate range has a maximum flow rate of 100 ml per minute, more particularly 50 ml per minute, and a minimum flow rate of 0.1 ml per minute, more particularly 1 ml per minute.

In one approach, the first and second motion transfer members are chosen and arranged with the bi-directional drive member and pump drive member such that at least one, and in some instances each, is capable of changing the fluid delivery rate of the pump by a factor of up to 1000× (e.g., 2×, 3×, 4×, 5×, 10×, 25×, 50×, 75×, 100×, 250×, 500×, 750× and 1000×) in corresponding relation to speed changes and/or changes in time of operation (e.g., more or less intermittent or continuous) of the bi-directional drive member. In another approach, the first and second motion transfer members are chosen and arranged with the bi-directional drive member and pump drive member such that the first output corresponds to a maximum first medical fluid delivery rate that is up to 1000 times greater (e.g., 2×, 5×, 10×, 20×, 50×, 100×, 250×, 500× and 1000×) than a second maximum medical fluid delivery rate, where the second maximum fluid delivery rate corresponds to the second output.

In another approach, the drive motor system of the present invention may be used as a compounding pump. In this application, the multi-fluid capability described in the infusion pump above would be used to compound two or more fluids. Medical compounding pumps typically combine two or more fluids to be administered to a patient. However, these systems are not connected to the patient, and are not used for administration purposes, but are generally used to delivery a medical fluid to a receptacle (e.g., in pharmaceutical applications). Non-medical compounding applications include systems for mixing two-part adhesives, foams and other fluid materials that need to be combined at the point-of-use. The drive motor system of the present invention may be used to continuously deliver two or more compounding fluids, with precise concentrations.

One of skill in the art would also readily understand that the transmission of the motor drive system of the present invention has many applications other than the infusion and/or compounding pump utilized to describe medical fluid delivery system herein. For example, the transmission could be used in a fluid sampling device, such as a device used in a fashion opposite to the described infusion pump in which a single inlet tube accepts a fluid and places fluid samples in multiple containers (e.g., in pharmaceutical applications). A further example includes the use of the transmission in mechanical actuators such as those used in aircraft, spacecraft, robotics, or assembly equipment. In order to move a large mass with precision and speed, the transmission of the present invention may be used. Rotation of a motor in a first direction in conjunction with the transmission of the present invention creates high speed to actuate the majority of the motion rapidly. Rotation of a motor in a second direction in conjunction with the transmission of the present invention leads to slower more precise motion. In an assembly line, for example, an automated arm may quickly rotate to retrieve a part from storage and bring it to the point of assembly. There, a motor may be rotated in a second direction in conjunction with the transmission of the present invention to allow for precise positioning of the part on the item being assembled.

Another embodiment for the transmission of the present invention is a simple, low cost drive mechanism. A motor may be combined with a two-speed transmission of the present invention to provide initial motion via the lowest gear ratio and the most mechanical advantage in a first motor direction, allowing an object to start moving from a complete stop. Switching to a second motor direction allows for faster, sustained motion via a gain in rotational speed created by a lesser mechanical advantage (i.e., higher gear ratio). Exemplary uses of such a two-speed drive transmission and motor include providing motive force for toys, scooters, cars, aircraft, boats, centrifuges, computer hard drives, CD-ROM drives and the like.

In another embodiment, the transmission of the present invention may be used in a human-powered vehicle, such as a bicycle. In such a system, pedaling in one direction engages the lowest gear ratio in order to allow the cyclist to easily begin moving from a complete stop. Pedaling in the opposite direction engages the higher gear ratio in order to maintain or increase speed. Additionally, a geared interface and a mechanism for engaging and disengaging the geared interface may be used with the two-speed bicycle transmission system to allow the cyclist to pedal continuously in one direction while still being able to alternate between the high and low gear ratio.

In order to overcome the disadvantages incumbent in the use of prior motors (e.g., stepper motors), the present invention describes a novel infusion pump mechanism in which a relatively inexpensive and lightweight motor may be driven bi-directionally to achieve a dual speed and torque range system suitable for operating a medical fluid pump over at least two flow rate ranges. This pump mechanism enables the design of a small and lightweight drive motor system capable of operating long term on batteries over wide flow ranges.

The present application hereinafter describes an inventive drive motor system, valve operating system, fluid line set and pinch valve in the context of a medical fluid delivery system. One of skill in the art will readily understand that the drive motor system described in relation to a medical fluid delivery system could be readily utilized as the motive force in any number of devices, particularly in devices which require a wide range of speeds and torques, including but not limited to, medical and non-medical compounding pumps, robotics, electronics and computers, linear and rotary actuators, automated laboratory instruments, spacecraft actuators, aircraft actuators, machine tools such as lathes, milling machines and presses, bicycle drive systems, automotive drive systems, cable drive systems, valve closure devices, centrifuges, high speed devices, fans, and energy storage devices.

In one embodiment, the medical fluid delivery system includes a pumping system. The pumping system may include a bi-direction drive member (e.g. a bi-directional drive motor having a motor shaft and a motor gear attached to the motor shaft), a transmission and a pump drive member. The transmission may comprise a first motion transfer member (e.g. a first gear and a first one-way clutch gear) mechanically interfaced with a portion of the pump drive member (e.g. an output shaft). In operation, turning the bi-direction drive member (e.g., bi-directional motor) in a first direction (e.g., clockwise or counterclockwise) creates a first output, which moves the first motion transfer member (e.g. first gear) and produces an output via (e.g., drives) the pump drive member (e.g., output shaft). However, turning the bi-direction drive member (e.g., bi-directional motor) in a second direction (e.g., counterclockwise or clockwise, whichever is the opposite of the first direction) produces a second drive output, and at least a portion of the first motion transfer member slips such that no output is produced. In other words, the first motion transfer member does not drive the pump drive member in response to the second dive output.

Also provided in the transmission may be a second motion transfer member (e.g. a second gear, a second one-way clutch and at least one additional transmission gear) mechanically interfaced with a portion of pump drive member (e.g. the output shaft). In operation, turning the bi-direction drive member (e.g., a bi-directional motor) in a first direction produces no output via the second motion transfer member. In other words, at least a portion of a second motion transfer member slips in response to the first drive output. That is, the second motion transfer member does not drive the pump drive member in response to the first drive output. However, turning the bi-direction drive member (e.g., a motor) in a second direction imparts motion to (e.g., drives) the second motion transfer member (e.g. second gear, second one-way clutch and at least one additional transmission gear) to produce a second output.

The medical fluid delivery system may further include a pump drive member for providing a mechanical output in one direction. In one approach, the pump drive member is configured and arranged with the transmission such that it is only capable of providing a mechanical output in one direction. The pump drive member may be mechanically interfaced with a pump, the pump being adapted to pump medical fluids. The medical fluid delivery system may further include a third motion transfer member mechanically interfaced with the pump drive member and the at least one additional gear, where the third motion transfer member slips in response to the first drive output. In one approach, the pump drive member, moves in one direction at a first speed in response to the first drive output, and moves in the same one direction at a second speed in response to the second drive output. In one particular aspect, the first speed and second speed are different. In this regard, the first and second outputs may be utilized to drive the pump drive member in one direction and over a wide-range of fluid delivery rates (e.g., from 0.1 ml per hour to 1000 ml per hour).

The present invention also includes a method of providing a medical fluid delivery system, which may include a pumping system operable over a range of motor speeds and torques, for delivering at least one medical fluid over a wide-range of flow rates. In a particular embodiment this method includes providing a bi-direction drive member (e.g., a bi-directional motor having a motor shaft and a motor gear attached to the motor shaft), a first motion transfer member (e.g. a first gear and a first one-way clutch), where the first motion transfer member is mechanically interfaced with the bi-direction drive member and with a portion of a pump drive member (e.g. an output shaft). In operation, the method includes operating the bi-direction drive member in a first direction, which moves the first motion transfer member to produce a first output via the output shaft. However, operating the bi-directional drive member (e.g. bi-directional motor) in a second direction causes the first motion transfer member to slip so no output is produced. The method further includes providing a second motion transfer member (e.g., a second gear, a second one-way clutch and at least one additional transmission gear) mechanically interfaced with the bi-direction drive member and a portion of a pump drive member (e.g. an output shaft). In operation, turning the bi-directional drive member (e.g. bi-directional motor) in the first direction produces no output from the second motion transfer member, but turning the bi-directional drive member (e.g. bi-directional motor) in the second direction moves the second motion transfer member to produce a second output. In one aspect, the first and second outputs are utilized to drive the pump drive member in one direction to drive the pump to achieve a wide-range of fluid delivery rates (e.g., from 0.1 ml per hour to 1000 ml per hour). The pump drive member may be mechanically interfaced with a pump, the pump being adapted to pump medical fluids.

In general terms, the medical fluid delivery system of the present invention may include a housing, a pumping system, (which may include a drive motor, a pump [e.g., a rotary peristaltic pump head] and a transmission), medical fluid lines through which a medical fluid may be flowed (e.g. pumped), a pump speed determination system, a processor for controlling the pump and a power source. Additional features of a medical fluid delivery system of the present invention may include a disposable medical fluid line set, which may include valves that may be opened, partially closed and closed to allow, impede (e.g., at least partially non-occlude), substantially occlude or completely occlude flow of a medical fluid. The medical fluid delivery system may also include a valve operating system adapted to interface with the valves of the disposable medical fluid line set. The valve operating system may include valve actuators adapted to interface with the valves to open and close the valves. The valve operating system may also include a valve status determination system operable to interact with the valve operating system for the selective actuation of one or more valve actuators.

The present invention also includes a method of pumping medical fluids. In a particular embodiment, the method includes providing a medical fluid pumping means having a pumping system described herein and operating such a system to pump a medical fluid.

In another particular embodiment, energy required to operate the medical fluid delivery system of the present invention may be provided by various means, including, but not limited to, electricity, steam, hydropower, wind power, solar power, human or animal power and any other means known to produce energy.

The pump of the pumping system may include a pump head, which may consist of a rotary peristaltic pump mechanism, as is widely known in the field. Briefly, in one aspect, the pump head comprises pinch members (e.g. spring-loaded pinch rollers) equally spaced around the pump head that rotate about roller shafts on a sleeve bearing and pinch a medical fluid line (e.g. flexible tubing) against an anvil surface. The pinch members may be designed to substantially occlude the medical fluid line against the anvil, and, therefore, the pinch members may have the ability to account for system tolerances of different medical fluid line sets. The pinch members may be biased away from the center of head rotation by a pinch-spring (e.g. coil torsion spring), which also retains the pinch roller on its shaft. The pinch members may be allowed to slide an amount slightly more than system tolerances toward and away from the medical fluid line. The motive force may be the pinch-spring (e.g. a novel coil spring), which may engage the roller shafts on either side of the roller in a partial hole provided in the shafts. The pinch-spring, therefore, maintains the placement of the rollers and provides motive force.

The pump head rotates and pinches the medical fluid line against an anvil. In a particular embodiment, the anvil is movable to allow initial placement of a medical fluid line in the channel provided. In a particular embodiment, the anvil is also mechanically coupled to the motion of an angular element (e.g., a cover) of the medical fluid delivery system. Briefly, to access the channels to put a medical fluid line into the pump, an angular element (e.g. cover) is provided that rotates up to approximately 100 degrees about two hinge points. When the cover is opened, the anvil is drawn away from the pinch rollers to allow placement of the medical fluid line. When the cover is closed, the anvil is moved towards the pinch rollers and the medical fluid line is pinched therebetween.

In one embodiment of the present invention, rotation of the pinch members in a first direction moves medical fluid from one or more medical fluid delivery lines to a medical fluid output line (e.g., for delivery to a patient). In an alternate embodiment, rotation of the pinch members in a second direction moves medical fluid from the medical fluid output line to one or more medical fluid delivery lines. Use of the invention in the alternate embodiment would allow for distribution of a medical fluid into multiple receptacles, (e.g., as in a pharmaceutical environment).

The coupling of the motion of the angular element of the medical fluid delivery system (e.g., a cover) to the motion of the anvil may be accomplished as described below. The angular element (e.g., cover) may be pivotally connected to a housing by one or more hinges, as described above. The angular element (e.g., cover) may contain a partial internal gear ring adjacent to a hinge point, which may be arranged to mechanically connect to a gear on the anvil shaft. The gear of the anvil shaft may be chosen to have a pitch diameter smaller than the ring gear of the angular element (e.g., cover). The ratio of the ring gear to the anvil shaft gear may be chosen such that movement of the internal gear ring moves the anvil an amount necessary to enable placement of the medical fluid line within the pump (e.g. 200 degrees of anvil shaft rotation for approximately 100 degrees of angular element (e.g., cover) rotation). The anvil shaft may be constrained to rotate by a sleeve bearing and the anvil may be mechanically engaged to an offset portion of the anvil shaft by an engaging sleeve bearing. This engaging sleeve bearing may be arranged to contact the anvil such that the rotary motion of the anvil shaft produces a linear motion of the anvil. The anvil shaft may also be arranged to rotate approximately 20 degrees past maximum displacement to provide a method of self-holding the anvil and cover in the open position.

In a particular embodiment, a cantilever force beam may be mechanically attached to the anvil such that as the anvil slides towards the pump head, the end of the force beam contacts a medical fluid line at a point downstream from the pump head. This contact compresses the medical fluid line at the point of contact. Pressure inside the medical fluid line causes the cantilever force beam to register more or less force in a substantially linear fashion. The pressure information may be collected continuously as the pump runs and sent to a computer processor, which can use the pressure information to determine whether the pumping system is operating correctly. For example, the processor can determine whether a medical fluid source is empty or whether a medical fluid line is blocked by comparing current pressures to a known pressure profile.

In another aspect, a pressure relating to fluid flow through the medical fluid line may be measured using a force sensor (e.g., a piezoelectric sensor) located downstream of the pump and in physical communication with the medical fluid output line. As is known in the art, the force sensor may be communicatively coupled to a processor to collect pressure information about the medical fluid output line.

The motion of the rotary peristaltic pump head may be driven by a bi-directional drive member (e.g. bi-directional motor) coupled with a transmission (e.g. a system of gears and clutches). In a particular embodiment, the drive motor may be a miniature DC iron-less core motor, with or without an integral gear train, and a motor gear frictionally attached to the output shaft of the motor. In one approach, the bi-directional motor may be operated over a wide range of speeds (e.g., by changing the supplied current and/or voltage to electric bi-directional drive motor) and intermittent times. Such speed variation and/or intermittent operation times, thus, enables the rotary peristaltic pump head interfaced with such bi-directional drive motor to deliver medical fluids over a wide range of flow rates, in corresponding relation to the first and second outputs over various speeds. A transmission may be mechanically interfaced with the bi-directional drive motor and the pump head to help enable the pumping action, as described in further detail below.

One of skill in the art would readily understand that fewer or greater gear combinations and/or gear ratios, as described herein, may be employed to achieve the speed and torque required for the various medical fluid delivery rate ranges for any given application of the pump. In a particular embodiment, gear combinations may be formed of a molded material such as DELRIN or similar material, which provides its own bearing surface on a shaft. However, one of skill in the art will appreciate that different materials could be employed to achieve the same result.

Various methods known to those of skill in the art may be used to measure and control the motion of the pump head. In a particular embodiment, the medical fluid delivery system comprises a pump speed determination system, where the pump speed determination system includes an encoder (e.g., optical, reflective and/or magnetic). As will be appreciated, encoders are well known in the art and may be utilized in accordance with well-known principles to determine the speed, motion, and/or position of the pump head. For example, the encoder may be utilized in relation to the motion of a pump drive member (e.g., an output shaft and/or pump drive shaft) to determine such speed, motion and/or position of the pump head. In a particular embodiment, the encoder may be an optical encoder, such as those supplied by US Digital Communications Inc (Chevy Chase, Md., U.S.A.), including the E4 miniature optical encoder.

In a particular approach, the pump speed determination system may utilize a magnets to determine the pump speed and/or motion. In this regard, a portion of the pump drive member (e.g. an output shaft) may have four magnets equally positioned around its surface. A flex circuit, or other means of connecting electrical switches to a device controller may be provided. For example, a flex circuit containing two reed switches approximately 45 degrees rotationally apart may be placed on a housing or other suitable location adjacent to the magnets to provide a signal for approximately 22½ degrees of the pump head. As the four magnets rotate over the reed switches, a signal is generated that can be sent to a processor. Using this signal, the speed and direction of rotation may be determined based upon the sequence of switch closure, which may allow the processor to insure the system is operating as requested.

Valves and a valve operating system are also provided, as described below. Initially, it is noted that many previously described systems provide valve mechanisms which are formed as part of the infusion pump. However, such arrangements are disadvantageous since once the medical fluid delivery line is removed from the pump, accidental fluid movement to the patient can occur. Therefore, it is advantageous to provide a valve arrangement which cooperates with the mode of operation of the infusion pump, but which can also be manually opened and closed apart from the operation of the infusion pump. In a particular embodiment, such a valve arrangement is designed to automatically close when a valve is removed from the medical fluid delivery system. A particular embodiment of the present invention may include a first pinch valve, which may be designed to be biased to a normally-closed position or normally-open position.

Briefly, a pinch valve operates in a manner similar to a sprung clothespin in that it comprises two elongated members that are coupled by and/or biased by a spring or other biasing force located a distance from a pivot point, where the elongated members are forced together at one end and apart at the other. The valve is further adapted such that a medical fluid delivery line of a disposable medical fluid line set, as described below, can be received by (e.g. run between) the elongated members, and, thus, be pinched by the ends which may be normally together. Thus, when the valve is in a first position (e.g. normally-closed), fluid may not flow through the line. When force is applied to compress the normally apart ends towards each other, the normally together ends will be forced apart, (e.g., releasing the pinched medical fluid delivery line when employing a normally-closed valve). Thus, when the valve is in a second position (e.g. open), medical fluid may flow through the medical fluid delivery line.

In a particular embodiment, the elongated members of the valve may have either a rib (e.g., a ridge) or a valley on the surfaces that may contact the medical fluid line. In one embodiment, the elongated members comprise ribs which engage each other when the valve is in a closed position, thereby substantially occluding fluid flow through a medical fluid line interfaced therewith.

In another approach, a rib and valley may contact the medical fluid such that the line is formed (e.g. moved) into a serpentine path when the valve is in a closed position. In a particular embodiment, a first elongated member may have at least one rib about substantially perpendicular to the flow path of a medical fluid line. At least one valley on the member surface of a second elongated member may interface with the at least one rib when the rib and valley are moved (e.g. biased) together. When the valve is in the closed position, the first elongated member comprising the at least one rib and the second elongated member comprising the at least one valley may compress (e.g., pinch) the medical fluid line. As noted above, in one approach the pinching results in the forming of the medical fluid line into a serpentine path, thus forming at least three contact points, and at least a portion of the inside walls of the line will be forced to meet. Thus, when the at least one rib and at least one valley pinch the medical fluid line, the at least three closure points effectively close the medical fluid line. In one embodiment, when the valve is in the open position (e.g., a non-pinching position), the at least one rib and at least one valley of the elongated members may be spaced a sufficient distance from each other to allow fluid flow through the medical fluid delivery line.

In a particular embodiment, a plurality of guide members integral to the elongated members may be provided for insuring the medical fluid line is retained in the proper place, and that the line may be oriented correctly to be formed into a serpentine path. The elongated members, guides, rib(s), valley(s) and/or biasing means may be formed of any material that will provide the required strength and flexibility, such as plastic.

A system and method for opening and closing the pinch valves is also provided. In one embodiment, the elongated members of a valve may be interfaced with a valve actuator via first and second interface adaptations, respectively. In this embodiment the proximal ends of the elongated members of the valve may be, for instance, normally biased away from each other, such that the action of the valve actuator forces the proximal ends towards each other to open or close the valve. In one aspect, the valve actuator may be held in place by a sleeve bearing, where the valve actuator is axially retained by an actuator return member (e.g. a torsion spring), which may be connected through the center of a valve actuator shaft. The actuator return member (e.g. torsion spring) may provide a motive force (e.g. a rotational motive force) to the valve actuator, and axially retain the valve actuator. In a particular embodiment, the actuator return member (e.g. a torsion spring) axially retains the valve actuator by the inside edge of the spring wire passing through a central hole in the valve actuator shaft. The geometry of the wire form and the preload of the torsion spring may prevent the valve actuator from disengaging from the sleeve bearing.

In one aspect, an actuator gear may engage the valve actuator by use of a suitably sized rotational actuator clutch. This actuator clutch may be frictionally fit to the inside diameter of the actuator gear such that the actuator clutch is arranged to engage the valve actuator shaft when the actuator gear is being turned in a direction required to engage the valve. When the actuator gear is turned in the opposite direction, the clutch slips causing no motion to the valve actuator or valve.

In a particular embodiment, a method for valve actuation is accomplished as described below. The valve actuator is provided with second adaptations (e.g. openings), which are adapted to receive first adaptations (e.g. protrusions) of a pinch valve. As used herein, adaptations is used to broadly define openings and protrusions, for example, slots and pins, respectively, which complement and receive each other, and is not intended to limit these components to any particular shape or size. In one approach, the openings (e.g. slots) are arranged to have a decreasing radius rotationally around one of the valve actuator or valve, so that as the valve actuator is rotated, the decreasing radius of the valve actuator engages the mating first interface adaptations (e.g. pins) and forces the elongated members of the valve, which may be normally biased away from each other, to approach each other, thereby opening or closing the valve. For example, the interface adaptations of the valve or valve actuator may be slots, where the slots have a wide proximal end, a narrow distal end, and an arcuate path between the wide proximal end and the narrow distal end, where at least a portion of the path tapers from the wide proximal end to the narrow distal end.

In one embodiment, the valve comprises at least one pin and the valve actuator comprises at least one slot adapt to receive the at least one pin. In another embodiment, the valve comprises at least one slot and the valve actuator comprises at least one pin.

The valve operating system may also comprise valve interface members (e.g. actuator gears, actuator clutches, and valve actuators) and activation members (e.g. mutilated gears). Each actuator gear may be in intermittent geared contact with a mutilated gear, which may pivot about a shaft on a sleeve bearing. In one approach, each mutilated gear may have two or more vertical sections of teeth. A system utilizing two sections, referred to herein as "upper" and "lower" sections, is described to exemplify the invention only. In a particular example, the edge of the lower section has teeth around the full perimeter (e.g. circumference), whereas the edge of the upper section has teeth on less than the full perimeter of the gear. The amount of the edge of the upper section having teeth is determined by the number of valves to be controlled. For example a two-valve system may have gear teeth on approximately one-half of the perimeter of the upper section, while in a system having four valves the upper section of the mutilated gear would have gear teeth on approximately one-quarter of the perimeter, (e.g. equal to about 90 degrees of rotation). For example, in a four-valve system, the actuator gear may be arranged to make and break contact with the mutilated upper section of the mutilated gear, thus providing a system where each actuator gear is in geared contact for approximately 90 degrees of rotation of its corresponding mutilated gear. In a particular embodiment, the mutilated gears may be arranged in an arc such that the lower section of each mutilated gear is in geared contact with a central drive gear. This arrangement provides a central location where a central drive gear can drive a plurality of mutilated gears simultaneously, and where less than all actuator gears and corresponding valve actuators are imparted motion from the central drive gear via the mutilated gears at any given time.

Alternately, multiple valves may be opened at the same time. For example, an activation member (e.g. a mutilated gear) with 180 degrees of coverage in the upper section may be used in a four-valve system. The 180 degrees of coverage may be contiguous, thus opening two neighboring valves or may consist of two 90 degree sections opposing each other such that every other valve may be opened simultaneously. Likewise, an activation member (e.g., mutilated gear) with full coverage on the upper section could be used in a four-valve system to open all four valves simultaneously. One of skill in the art will understand that various activation member arrangements could be employed in the valve operating system to open and close different valves independently, simultaneously and in numerous combinations.

In another aspect, the medical fluid delivery system comprises a valve status determination system, which may calculate the speed, motion and/or position of the various members of the valve controller. In a particular aspect, the valve status determination system includes an encoder (e.g., optical, reflective and/or magnetic). As described above, such encoders are well known in the art and may be utilized in accordance with well-known principles to determine the speed, motion and/or position of the various component of the valve controller For example, the encoder may be utilized in relation to the central drive gear. In a particular embodiment, the encoder may be an optical encoder, such as those supplied by US Digital Communications Inc (Chevy Chase, Md., U.S.A.), including the E4 miniature optical encoder.

In an another embodiment, magnets may be employed where a central drive gear may contain four magnets that are arranged to rotate above two reed switches approximately 45 degrees rotationally apart. As the four magnets rotate over the two reed switches, a signal may be generated which may be sent to a processor. Using this signal, both speed of rotation and direction of rotation can be determined based upon the sequence of switch closure, allowing the processor to insure the valve operating system is operating as requested.

In one approach, the valve operating system comprises a central drive member, which may comprise the central drive gear, a drive motor and a motor gear. The central drive gear may be in geared contact with the drive motor, either directly or through one or more transfer gears (e.g. a motor gear). The drive motor may be a standard brushed DC motor with an integral gear reduction that can be driven either unidirectionally or bi-directionally. This motor may be sized to deliver appropriate speed and torque to the valve actuator through activation members to motivate the opening of valves. In a particular embodiment, as the motor gear moves in a first direction (e.g. clockwise), the central drive gear turns all four activation members (e.g. mutilated gears) simultaneously, whereby the actuator gears are rotating in a direction of slip with respect to their actuator clutches. Thus, none of the valve actuators will be moved when the motor gear moves in a first direction.

As the motor gear moves in a second direction (e.g. counterclockwise), at least a single actuator gear may be engaged by (e.g. interfaced with) an activation member at any one time due to the rotational offset arrangement of the activation members (e.g. mutilated gears). An actuator gear in geared contact, therefore, will be required to rotate in a direction that causes each clutch of each actuator gear to engage and thereby rotate each valve actuator. As the motor gear moves (e.g. rotates) in the second direction, the motor provides motive force to rotate the valve actuator in order to open the valve. The actuator return member (e.g. a torsion spring) of the valve actuator may provide a motive force to automatically rotate the valve actuator to an initial position (e.g., starting position) when the motive force of the motor is removed, thereby closing the valve. Thus, the motive force or the valve controller (e.g. a motor) can be rapidly placed in random contact with each valve actuator (e.g. via the actuator gear) for opening a corresponding valve (e.g. by moving clockwise or in the direction of non-engagement for the actuator clutches), thus providing a means for opening a single valve at a time without disturbing the fluid valves that are not meant to be opened.

In one embodiment, the elongated members of the valve and/or the valve actuator have walls comprising a slight taper. In the initial rest position the valves may be closed and fit loosely in the second interface adaptations (e.g., the valve actuator slots/recesses). With a medical fluid delivery system cover in place, the valves will be held in the recesses provided and will be forced to open by the action of the valve actuators. However, if the cover is opened while the valve actuator is acting on a valve, the restraining force of the cover is removed and the taper of valve and/or valve actuator walls lifts the valve out of the recess, where a biasing means (e.g. a spring) may cause the valve to return to a closed and safe (e.g. no fluid flow) position. Thus, the cover of the present invention may have dual functionality in that may act as a restraining force to maintain the valves within the medical fluid delivery system, and, as described earlier, it may act as an angular element to assist in the placement of a medical fluid line within the pump.

In one approach, the valve operating system may comprise a valve status determination system, which may comprise sensors to verify valve motion. In a particular embodiment, electrical switches are placed such that a portion of the switch protrudes into a valve housing area. In the absence of a valve, the switch is closed. In the presence of a valve, the switch is opened. As the valve is opened by a valve actuator, the switch again closes and provides a means for a device control unit to determine the number of valves being operated, and the position of each valve at any given time during operation.

In another embodiment, a disposable medical fluid line set is provided, which may include the valves described herein.

When multiple fluid delivery lines are provided, each medical fluid delivery line may be in fluid communication with a common manifold, which in turn may be in fluid communication with a medical fluid output line, which may interface with a pump head. The fluid lines and manifold described herein may be molded or formed as a single, contiguous piece, or may be separate pieces in fluid connection with each other. In a particular embodiment, the medical fluid lines may be made of medical grade silicone tubing, which may either be extruded and cut to length or injection molded to final shape. Also, the manifold may be injection molded of the same silicon as part of a line molding process or injection molded as a separate piece of medical grade plastic.

In another aspect, an inventive medical fluid delivery system may utilize a disposable medical fluid line set in the delivery of a plurality medical fluids. In this regard, an inventive medical fluid delivery system is provided for the delivery of one or more medical fluids. The medical fluid delivery system may include a medical fluid line set, which may include a first medical fluid delivery line for delivering a first medical fluid therethrough, and a first valve adapted to interconnect with the first medical fluid line. In one approach, the valve is one of fixedly interconnected and slidably interconnected to the first medical fluid delivery line. When the valve is slidably interconnected to a medical fluid line, the valve may be move about the fluid line and may be retained at either end of the medical fluid line by a spike or other stopping member.

In another embodiment, the first valve includes a biasing means for biasing the first valve in one of a normally-closed position and normally-open position. In one embodiment, the first valve has a first interface adaptation (e.g., at least one protrusion).

The medical fluid delivery system of may further include a first valve actuator having a second interface adaptation (e.g., at least one opening). The second interface adaptation may be configured to interface and co-move with the first interface adaptation of the first valve. In one particular approach, the first interface adaptation and the second interface adaptation are sized to matably receive each other. In one particular aspect, the second interface adaptation is a slot that includes a wide proximal end for matably receiving the first interface adaptation, a narrow distal end, and an arcuate path between the wide proximal end and the narrow distal end which tapers down to the narrow end. In this particular aspect, the first interface adaptation is sized to matably engaged the slot at a point along the arcuate path.

In one approach, the first valve actuator is positionable to a first and second position, where in the first position a portion of the first medical fluid delivery line is pinched by the valve, thereby accomplishing a first degree of occluding of fluid flow through the first medical delivery line, wherein fluid flow through the medical delivery lined is at least substantially occluded, if not fully occluded. When the first valve actuator is in the second position, a second-degree of occluding of the medical fluid delivery line is accomplished, where fluid flow through the medical delivery line is at least partially non-occluded, and in some instances, completely non-occluded (e.g., open).

In one particular aspect, the first interface adaptation and second interface adaptation of the valve and valve actuator, respectively, are matably engaged in the second position to open the first valve. In yet another approach, the medical fluid delivery system includes an actuator return member operatively interfaced with the valve actuator and adapted to automatic return the first valve actuator from the second position to the first position. The actuator return member may be in the form of a biasing means, such as a torsion spring.

In another embodiment, the medical fluid delivery system further includes a second medical fluid delivery line, a second valve adapted to interconnect with the second medical fluid delivery line, and a second valve actuator for interfacing with the second valve. In one aspect, the second valve comprises at least one of the first interface adaptation and second interface adaptation, and the second valve actuator comprises at least one of the first interface adaptation and second interface adaptation. In one particular approach, the first and second valve each comprise the first interface adaptation and the first and second valve actuator each comprise the second interface adaptation. In one embodiment, the second valve is fixedly interconnected to the second medical fluid delivery line.

In another aspect, the medical fluid delivery system may include a valve controller adapted to mechanically impart motion to the first valve actuator and second valve actuator. In this regard, a first motion output of the valve controller will at least partially actuate the first valve actuator, and a second motion output of the valve controller will lease partially actuate the second valve actuator. In one particular approach, the first motion output and second motion output are at least partially non-overlapping. In one aspect, the first motion output and second motion output are entirely non-overlapping.

In another approach, the medical fluid delivery system includes a bi-directional motor, a transmission adapted to mechanically interface with a bi-directional motor, and a pump drive member for providing a mechanical output in one direction. In this regard, the pump drive member is adapted to mechanically interface with the transmission and the pump, where operation of the bi-directional motor in a first direction produces a first output that drives the pump drive member in one direction. Further in this regard, the pump drive member is adapted to mechanically interface with the transmission of the pump, where operation the bi-directional motor in a second direction produces a second output that drives a pump drive member in the same one direction.

The present invention also includes an inventive method for use in the delivery of one or more medical fluids. In this regard, the inventive method may include the steps of providing a medical fluid line set, interconnecting a pump with the medical fluid output line of the medical fluid line set, interfacing a first interface adaptation of a first valve of the medical fluid line set with a second interface adaptation of a first valve actuator, actuating the first valve actuator to move the first valve from a first position to a second position, and operating, during the actuating step, the pump to deliver a first medical fluid. In this regard, the medical fluid line set may include the first valve, the medical fluid output line, and a first medical fluid delivery line fluidly interconnected to a first medical fluid source. The first valve may be interconnected with the first medical fluid delivery line, such as fixedly interconnected.

In one aspect, the actuating comprises rotational movement of the first valve actuator, and the rotational movement of the first valve actuator comprises no more than 180 degrees of rotation. In another aspect, the operating the pump step comprises the steps of first moving a bi-directional drive member in the first direction to move the pump in one direction at a first speed, and second moving the bi-directional drive member in a second direction to move the pump in the same one direction at a second speed.

The method may further include the step of automatic returning the valve actuator to the first position after the actuating step. In one approach, during the actuating step, the first interface adaptation and second interface adaptation are matably engaged. In this regard, one of the first interface adaptation and second interface adaptation may comprise an opening, and the other of the first interface adaptation and second interface adaptation may include a protrusion. Further in this regard, the interfacing step may comprise the step of inserting the protrusion into the slot.

In another approach, the method may include the steps of interfacing a first interface adaptation of a second valve with a second interface adaptation of a second valve actuator, de-actuating the first valve actuator to return the first valve actuator to the first position, and second actuating the second valve actuator to move the second valve from a first position to a second position. In this regard, when the second valve actuator is in the first position, the second valve will substantially or completely occlude fluid flow through a second medical fluid delivery line. When the second valve actuator is in the second position, the second valve permits fluid flow through the second fluid delivery line. Further in this regard, the medical fluid line set includes the second medical fluid delivery line, which is fluidly interconnected to a second medical fluid source and the medical output line, and the second valve which is interconnected with the second medical fluid line. In this approach, the method may further include the step of operating the pump to deliver the second medical fluid during the second actuating step. In another aspect of this approach, the first actuating step of the method may further include the steps of first creating a first motion output of valve controller, and second creating a second motion output of the valve controller, where the first motion output and second motion output are at least partially non-overlapping. In this regard, the valve controller is mechanically interfaced with the first valve actuator and the second valve actuator.

In another embodiment, the method may include the step of moving a component of the pump in linear response to an angular output of an angular element to enable placement of a portion of a medical fluid line in at least a portion of the pump. In this regard, the component of the pump may be an anvil and the angular element may be a cover. The angular output may also comprise rotational movement of the angular element from a first position to a second position. As used herein, "angular element" means any element associated with the medical fluid delivery system that may move from a first angle to a second angle, such as by rotational movement. In particular, the angular element may include covers, shafts, motion transfer members (e.g. gears) and the like.

The present invention also includes an inventive valve operating system for use in delivering a plurality of medical fluids. The valve operating system may include first and second valve interface members, which may include first and second valve actuators adapted to operatively interface with first and second medical fluid delivery valves, respectively. The valve operating system may further include a valve controller mechanically interfaced with the first and second valve interface members. In this regard, the valve controller may produce a first output that at least partially actuates the first valve actuator, and a second motion output that at least partially actuates the second valve actuator. In one aspect, the first motion output and second motion output are at least partially non-overlapping. In one particular aspect, the first motion output and second motion output are non-overlapping. In one embodiment, the first motion output of the valve controller corresponds to movement of the valve controller from a first controller position to a second controller position, and the second motion output of the valve controller corresponds to movement of the valve controller from the second controller position to a third controller position.

In one embodiment, the valve controller includes first and second activation members adapted to operatively interface with the first and second valve interface members, respectively. In this embodiment, in the first controller position, the first activation member of the valve controller is at least partially interfaced with the first valve interface member, and the second activation member is at most partially interfaced with the second valve interface member. In the second controller position, the first activation member is partially interfaced with the first valve interface member, and the second activation member is partially interfaced with the second valve interface member. In the third controller position, the first activation member is at most partially interfaced with the first valve interface member, and the second activation member is at least partially interfaced with the second valve interface member. In one approach, in the first controller position the second activation member is not interfaced with the second valve interface member.

In one embodiment, the first and second motion outputs of the valve controller comprise circular rotation of at least a portion of the valve controller. In this regard, the first motion output may be a first arcuate rotation of a first activation member, and the second motion output may be a second arcuate rotation of a second activation number. In one approach, the first arcuate rotation corresponds to rotation of the first activation member by no more than 180 degrees. In another approach, the second arcuate rotation corresponds to rotation of the second activation member by no more than 180°. Further this regard, the first and second arcuate rotations may occur at least coincidentally (e.g., in overlapping temporal relation or even contemporaneously).

In another approach, the activation members (e.g., first, second, etc.) included an upper section adapted to mechanically interface with the first of interface member, and a lower section mechanically interfaced with a central motion transfer member. The upper section includes an active interface portion extending about a segment of the perimeter of the lower section of each activation member. The lower section includes a motion transfer mechanism (e.g., geared teeth) about the entire perimeter of the lower section of each activation member. In one approach, the active interface portion is contiguous. In another approach, the active interface portion is noncontiguous. In one particular embodiment, the active interface member comprises gear teeth for mechanically interfacing with its respective valve interface member. As used in this paragraph, the terms "upper" and "lower" are used for illustration purposes only, and are not meant to be limiting in any fashion.

The present invention also includes an inventive method for delivering a plurality of medical fluids. In this regard, the method comprises the steps of fluidly interconnecting at least first and second medical fluid delivery lines with one pump, first operating the one pump to deliver a first medical liquid through the first medical fluid delivery line, and second operating the one pump to deliver a second medical liquid through the second medical fluid delivery line, where the first operating and second operating steps occur during the fluidly interconnecting being step.

In one approach, the fluidly interconnecting step further comprises the steps of interfacing a first valve interconnected with the first medical fluid delivery line with a first valve actuator, and interfacing a second valve interconnected with the second medical fluid delivery line with a second valve actuator. In this regard, the method may further comprise the step of first positioning a valve controller from a first controller position to a second controller position to actuate the first valve actuator. In one approach, the second valve actuator remains in a non-actuated position during the first positioning step. Further in this regard, the method may further comprise the step of second positioning the valve controller from the second controller position to a third controller position to actuate the second valve actuator. As will be appreciated with this approach, the method is able to achieve synchronous or non-synchronous coincidental movement of one or more valve actuators utilizing a single valve controller, as is described in further detail below. This approach is especially useful when employing a plurality of medical fluids for delivery, as it is often desirable to actuate certain valves in a particular order to achieve the desired medical fluid delivery.

In another embodiment, the method further comprises actuating the first valve actuator. In one approach, this actuating step may comprise the steps of first moving a valve controller in a first direction and driving the first valve actuator from a non-actuated position to an actuated position during the first moving step. Further in this regard, the actuating step may further comprise the step of second moving the valve controller in a second direction to position the valve controller for the first moving step, where the second moving step occurs prior to the first moving step. In one approach, the second valve actuator remains in a non-actuated position during the second moving step. In yet another approach, the second valve actuator remains in a non-actuated position during both the first moving and second moving steps. As will be appreciated with this embodiment, the method is able to achieve controlled opening of a selected valve without opening other valves within the medical fluid delivery system, as it described in further detail below. This embodiment is especially useful when employing a plurality of medical fluids for delivery, as it is often desirable to actuate only one valve without actuating other valves to avoid unintentional or unwanted medical fluid delivery.

In another approach, the actuating step occurs prior to the second operating step. In another embodiment, the method further comprises the step of second actuating the second valve actuator. In one approach, the method further comprises automatically returning the first valve actuator to a non-actuated position after the first positioning step.

In another embodiment, the method may include the step of relating the first valve to the first valve actuator by matching a color designation of the first valve to a color designation of the first of actuator. The method may further comprise the step of moving, prior to the fluidly interconnecting step, a component of the pump in linear response to an angular output of an angular element to enable placement of a portion of the medical fluid output line in at least a portion of the pump. In this regard, the component of the pump may be an anvil and the angular element may be a cover. The angular output may also comprise rotational movement of the angular element from a first position to a second position.

The present invention also provides for an inventive method for delivering a medical fluid at varying rates using a single pump. The method may include the steps of interconnecting a medical fluid line with one pump, first operating a bi-directional drive member in a first direction to produce a first drive output, and second operating the bi-directional drive member in a second direction to produce a second drive output.

In one embodiment, bi-directional drive member is operable over an operating range, which may corresponds to a range of first outputs and second outputs. In one embodiment, the range of first outputs corresponds to a first medical fluid delivery rate range, and the range of second outputs corresponds to a second medical fluid delivery rate range. In one particular aspect, the first and second medical fluid delivery rate ranges are at least partially non-overlapping. In another aspect, the first and second medical fluid delivery rate ranges are non-overlapping.

Further in this regard, each of the first and second medical fluid delivery rate ranges may have maximum and minimum flow rates associated therewith. In one embodiment, the first medical fluid delivery rate range has a maximum flow rate 2000 ml per minute, more particularly 1000 ml per minute, and a minimum flow rate of 1 ml per minute, more particularly 5 ml per minute, even more particularly 10 ml per minute. In one embodiment, the second medical fluid delivery rate range has a maximum flow rate of 100 ml per minute, more particularly 50 ml per minute, and a minimum flow rate of 0.1 ml per minute, more particularly 1 ml per minute.

In one aspect of the method, the operating step comprises movement of the bi-directional drive member in one of a clockwise a counterclockwise direction, and second operating step comprises movement of the bi-directional drive member in the opposite direction of the first operating step. In one embodiment, the first operating step includes the step of first driving the pump drive member in a rotational direction in response to motion from a first motion transfer member. In this regard, the pump drive member is mechanically interfaced with the one pump and a first motion transfer member, and the first motion transfer member is mechanically interfaced with bi-directional drive member. In a particular embodiment, the second operating step comprises the step of second driving the pump drive member in the same rotational direction in response to motion from a second motion transfer member. In this regard, the pump drive member is mechanically interfaced with the second motion transfer member, and the second motion transfer member is mechanically interfaced with the bi-directional drive member. In one aspect, the second motion transfer member does not drive the pump drive member during the first driving step. In another aspect, the first motion transfer member does not drive the pump drive member during the second driving step.

The present invention also provides for an inventive medical fluid delivery system including a pinch valve adapted for receiving and engaging a medical fluid line, where the pinch valve will substantially or completely occlude fluid flow through a medical fluid delivery line received therein when the pinch valve is in a first position.

The pinch valve generally includes a first and second elongated members and a biasing means for forcing the first and second elongated members in at least a first direction about a pivot point to said first position to substantially or completely occlude fluid flow. The pinch valve may also include at least one rib, a second elongated member that includes at least one valley, and a biasing means for forcing at least one of the first and second elongated members in a first direction about a pivot point. At least one of the first and second elongated members may be adapted to receive the medical fluid delivery line. In this regard, in a first position of the pinch valve, a portion of the medical fluid delivery line is pinched between the first and second elongated members. In a particular approach, the portion of the medical fluid delivery line is formed into a serpentine path about the at least one rib at least one valley. The at least one rib and at least one valley are adapted for interfacing with each other to form the portion of the medical fluid line into the serpentine path when the pinch valve is in the first position.

In one aspect, in the first position the portion of the medical fluid delivery line is contacted in at least three points by the pinch valve. In a particular embodiment, in the first position, medical fluid is substantially or completely occluded from flowing through the portion of the medical fluid delivery line.

Further in this regard, in a second position of the pinch valve, medical fluid may flow through a portion of medical fluid delivery line.

In a particular embodiment, the pinch valve includes at least one interface adaptation for interfacing the pinch valve with a valve actuator. In this regard, the at least one interface adaptation may be one of a opening (e.g., a slot) or a protrusion (e.g., pin). In one aspect, the opening may be size for may be receiving a protrusion. In another aspect, the protrusion may be size for may deplete protruding into an opening.

In another embodiment, the pinch valve may include a first color designation for relating the pinch valve to a valve actuator. In another aspect, the pinch valve may comprise a lock mechanism for locking the pinch valve into a second position a portion of a medical fluid delivery line is at least partially non-occluded. In this regard, the lock mechanism may be operatively interconnected with at least one of the first and second elongated members to maintain the pinch valve in the second position. In a particular aspect, the lock mechanism is fixedly or slidably interconnected to at least one of the first and second elongated members. In another aspect, the lock mechanism is readily removable (e.g. a disposable) from the pinch valve.

The present invention also provides for an inventive method for delivering a medical fluid. The method may include the steps of first interconnecting a plurality of valves to a corresponding plurality of medical fluid delivery lines, the plurality of valves and plurality of medical fluid delivery lines defining a medical fluid line set, interfacing the medical fluid line set with the pumping system, and delivering medical fluid through at least one of the plurality of medical fluid delivery lines using the pump. The method provides for at least the first interconnecting step to occur at a first location (e.g., a manufacturing, cleaning, preparation and/or sterilization facility), and at least the delivery step to occur at a second location remote from the first location. The second location can be any location remote from the first location has a need to deliver a medical fluid, such as a medical care facility or pharmaceutical facility.

In one embodiment, the interconnecting step of the method comprises fixedly attaching the plurality of valves to the corresponding plurality of medical fluid delivery lines. In another embodiment, the method further comprises the step of second interconnecting the plurality of medical fluid delivery lines with the manifold. In this regard, the second interconnecting may occur at the first location. Further in this regard, the interfacing step method may include the steps of third interconnecting the manifold with a medical fluid output line, and placing the medical fluid output line at a portion of the pump. In one approach, the interfacing the step also occurs at the second location.

In another embodiment, the method may comprise the step of transferring the medical fluid line set from the first location to another location. In a particular aspect, the another location is the second location. In a further embodiment, the method may comprise the step of actuating at least one of the plurality of valves to a non-pinching position prior to the transferring step (e.g., such as at a manufacturing, cleaning, preparation and/or sterilization facility). Further in this regard, in the non-pinching position the at least one of the plurality of valves does not substantially pinch a corresponding one of the plurality of medical fluid delivery lines. In another embodiment, the method may comprise maintaining the at least one of the plurality of valves in the non-pinching position during the transferring step. In yet another embodiment, the method may comprise the step of de-actuating the at least one of the plurality of valves to place the at least one of the plurality of valves in a pinching position. In this regard, the de-actuating step may occur after the transferring step, such as at the second location (e.g., a medical care facility and/or pharmaceutical facility). In another aspect, the method may comprise the step of packaging the medical fluid line set. Further in this regard, the packaging step may occur after the actuating step (e.g., at a manufacturing, cleaning, preparation and/or sterilization facility). In another aspect, the method may comprise the step of sterilizing the medical fluid line set. In this regard, the sterilizing step may occur before the transferring step.

In another aspect, the method may comprise the step of relating the plurality of valves to the plurality of medical fluid delivery lines. In this regard, the relating step may comprise the step of matching a color designation of the plurality of valves to a color designation of the plurality of medical fluid delivery lines.

In another embodiment, the method may comprise the step of second interfacing the plurality of valves with a corresponding plurality of valve actuators. In this regard, each of the plurality of valves may comprise a first interface adaptation, and each of the plurality of valve actuators may comprise a second interface adaptation for interfacing with the first interface adaptation. The method may further comprise the step of relating the plurality of valves to the plurality of valve actuators prior to the second interfacing step. In this regard, the relating step may comprise matching a color designation of a component of the medical fluid line set to a color designation of a second component. Further in this regard, the component of the medical fluid line set may be one of the plurality of valve actuators and the plurality of medical fluid delivery lines. In another aspect, the second component may comprise the plurality of valve actuators. In another aspect, the second component may comprise a housing element, such as a recess of the housing or a port of a housing.

In another embodiment, the method may include the steps of moving a component of the pump in linear response to an angular output of an angular element to enable placement of a portion of a medical fluid line in at least a portion of the pump. In this regard, the component of the pump may be an anvil and the angular element may be a cover. The angular output may also comprise rotational movement of the angular element from a first position to a second position.

As will be appreciated, the inventive medical fluid delivery system may deliver a one or more plurality of medical fluids (e.g., to a patient or receptacle) using a medical fluid delivery system comprising anyone of the following, either alone or in combination: a pinch valve; a disposable medical fluid line set; a pumping system, which may comprise a drive motor system, a transmission, a pump drive member and/or a pump; a valve operating system; a pump speed determination system; a valve status determination system; a pressure measurement system; a power supply; a computer processor and control system; and/or a housing adapted to receive any of such items.

In one aspect, portions of the disposable medical fluid line set, (e.g. valves and/or a manifold) may be placed in corresponding recesses provided in a housing. The valves may be placed in valve recesses and a portion of the disposable medical fluid line set may be placed to interface with a rotary peristaltic pump head. Once in the proper recesses, particular elements of the disposable medical fluid line set may be further held in place by closing a cover. One or more separate means may be provided to assist in maintaining the disposable medical fluid line set in its proper position in the housing.

In another aspect, it may be desirable to hold the valves in the open position (e.g., non-pinching position) during product storage to prevent the medical fluid lines from being permanently deformed or collapsed by the pressure of the valve during storage or due to elevated temperature. In a particular embodiment, the disposable medical fluid line set packaging is arranged of semi-rigid vacuum formed plastic with appropriate structures to hold the valve in the open position during sterilization or storage.

In a particular embodiment, the medical fluid pumping system comprises a pump speed determination system that may sense pump head motion of by optical encoders and/or reed switches, described above. However control of the amount of rotation relates to the motor armature. The pump head diameter, the medical fluid line inside diameter, the transmission components (e.g. gears and their ratios), and the pump drive member components (e.g. worm gear ratio), may be matched in a fashion that the speed ratios of the transmission overlap and provide sufficient torque multiplication for the motor at both speed ranges, yet not overrun the motor armature speed.

The medical fluid pumping system may be controlled by many types of microprocessors commonly used for control applications. As commonly understood, the processor may accept the command inputs of the keys, display the status on a display, monitor the sensors for fault conditions, monitor the voltages of batteries, and direct the valve operating system and/or pumping system for correct operation.

One of skill in the art would readily understand that a medical fluid delivery system of the present invention may also have additional features useful for medical applications. For example, the medical fluid delivery system may comprise interface members so that the medical fluid delivery system may be operated on either battery power or on standard electrical outlets. The medical fluid delivery system may have various clips or features for holding items commonly found in settings where medical treatments are administered, such as clips suitable for attaching standard syringes. The medical fluid delivery system may also have features for mounting or hanging the medical fluid delivery system on a pole, which may be integral to the medical fluid delivery system, or removable in nature. An example of such a pole mount is one which magnetically attaches the medical fluid delivery system to the pole with sufficient force to allow an operator to actuate the keys, but will disengage from the pole should the patient be moved away from the mounting pole without first removing the medical fluid delivery system from the pole.

DETAILED DESCRIPTION OF THE INVENTION

Definitions

For the purposes of the present invention, the following terms shall have the following meanings:

For the purposes of the present invention, "a" or "an" entity refers to one or more of that entity; for example, "a valve actuator" or "an pinch valve" refers to one or more of the components or at least one component. As such, the terms "a" or "an", "one or more" and "at least one" can be used interchangeably herein. It is also noted that the terms "comprising," "including," and "having" can be used interchangeably. Furthermore, a component "selected from the group consisting of" refers to one or more of the components in the list that follows, including mixtures (i.e. combinations) of two or more of the components.

As used herein, a "pump" refers broadly to means for moving fluid. A pump may operate through changes in pressure and/or gravity. Pumps include but are not limited to rotary peristaltic pumps, linear peristaltic pumps, centrifugal pumps, diaphragm pumps and piston pumps.

As used herein, a "fluid" refers to any matter having fluidic properties, including but not limited to liquids, suspensions, gases and mixtures thereof.

As used herein, a "motion transfer member" is intended to broadly refer to any structure commonly used to transfer or receive a motion. Motion transfer members of the present invention may include, for example, gears, toothed or cogged structures, chains, pulleys, friction devices, magnetic couplings and combinations thereof.

The present application hereinafter describes the use of an inventive drive motor system, valve operating system, fluid line set and pinch valve in the context of a medical fluid delivery system. One of skill in the art will readily understand that the drive motor system in reference to a medical fluid delivery system could be readily utilized as the motive force in any number of devices, as described above.

Figure 1:
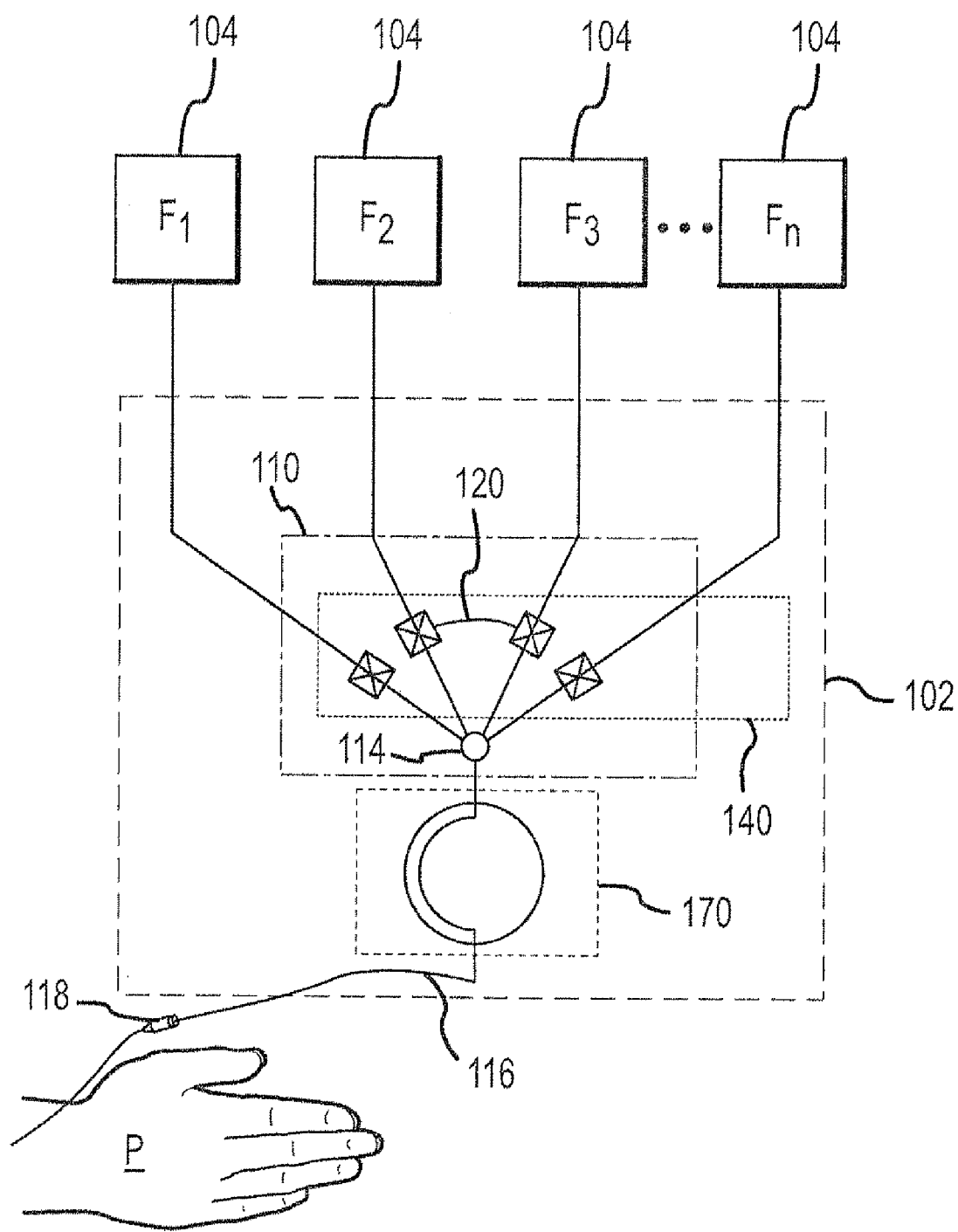
FIG. 1 is as a schematic view of one embodiment of the medical fluid delivery system of the present invention.

Reference will now be made to the accompanying drawings, which at least assist in illustrating the various pertinent features of the present invention. FIG. 1 illustrates a medical fluid delivery system according to the present invention. The medical fluid delivery system 102 may generally comprises a disposable medical fluid line set 110, a valve operating system 140, and a medical fluid pumping system 170. The disposable medical fluid line set 110 is generally fluidly connected to one or more medical fluid sources 104 and may be fluidly connected to a manifold 114. A medical fluid output line 116 may be fluidly connected to the manifold 114 at a proximal end and to a patient, via an IV catheter, at a distal end. In one embodiment, the medical fluid output line 116 is connected to a patient P via a coupler 118 for selectively connecting first and second portions of the medical fluid output line 116. As will be described in further detail below, the disposable medical fluid line set 110 may interface with the valve operating system 140 via valves 120. Generally, the valve operating system 140 operates the valves 120 of the disposable medical fluid line set 110 to enable delivery of one or more medical fluids to a patient P via the pumping system 170.

Figure 2:
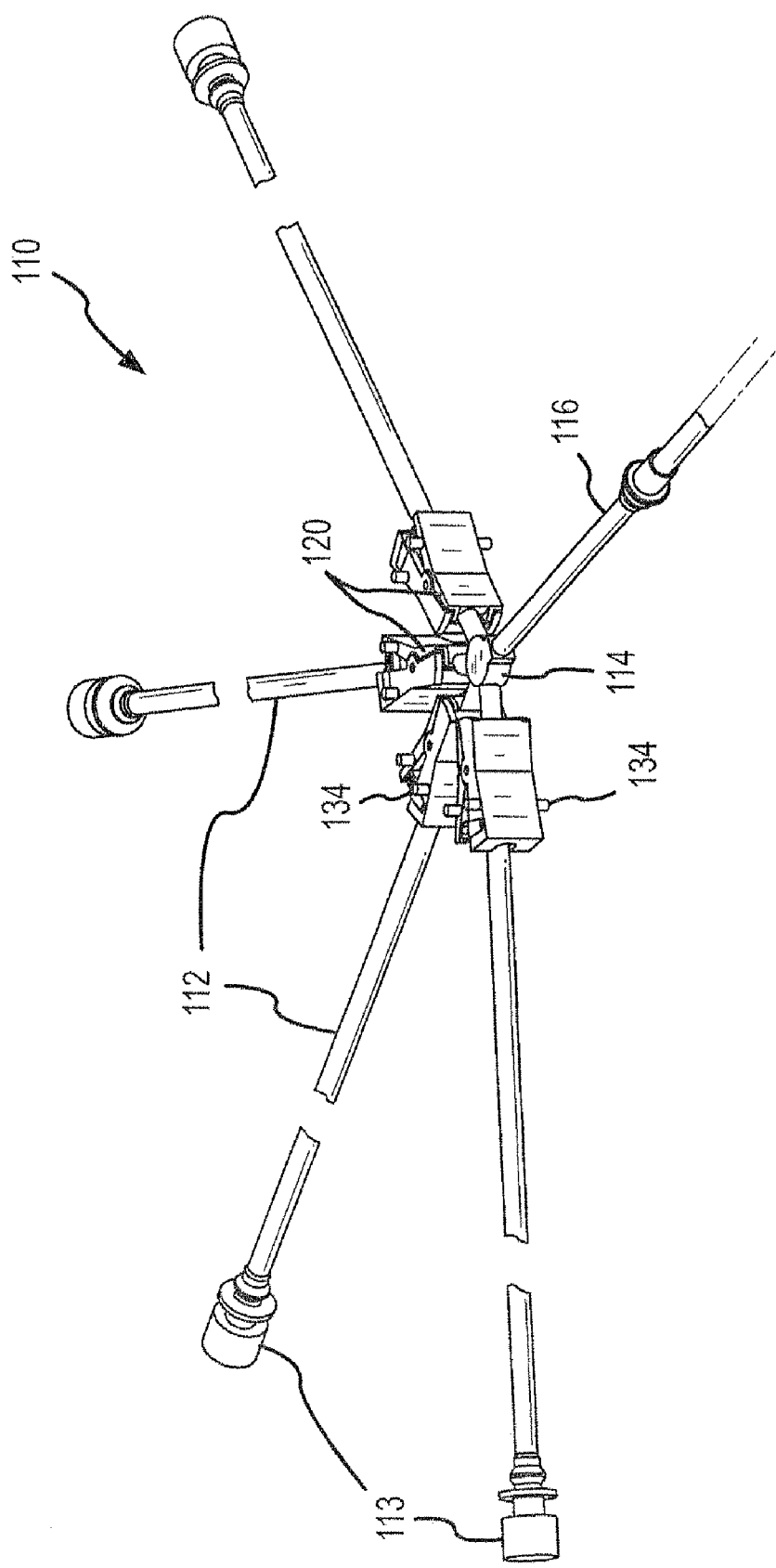
FIG. 2 is a schematic view of one embodiment of the medical fluid line set of the present invention.

In one embodiment, the medical fluid delivery system 102 may include a disposable medical fluid line set 110, which is now described in relation to FIG. 2. The disposable medical fluid line set 110 may be adapted to fluidly communicate with one or more medical fluid sources 104 via the medical fluid delivery lines 112. In one approach, the medical fluid sources may be fluidly connected to the medical fluid delivery lines 112 via couplers 113, as described below.

The medical fluid delivery lines 112 may be any well known type of fluid line used in medical applications, including fluid lines made of materials such as plastic and silicon that are adapted for the delivery of medical fluids. In one embodiment, a distal end of one or more of the medical fluid delivery lines 112 may comprise couplers 113, which may be used to selectively connect to the medical fluid sources 104. In another approach, a proximal end of one or more medical fluid delivery lines 112 is fluidly connected to a manifold 114. In one approach, the medical fluid lines 112, 116 and manifold 114, as described above, may be molded or formed as a single contiguous piece in fluid communication with each other. Alternatively, the medical fluid lines 112, 116 and manifold 114 may be separate pieces adapted to interface and fluidly communicate with one another. As used herein, medical fluid refers to any type of fluid that may be used in the medical field including, without limitation, solutions comprising water and/or drugs, liquids, suspensions, gases and combinations thereof.

In one aspect, one or more of the medical fluid delivery lines 112 may be received by one or more valves 120. As discussed in further detail below, the valves 120 are adapted to control flow of medical fluids through the medical fluid delivery lines 112, such as by opening, closing and achieving positions therebetween, to achieve first and second degrees of occlusion, for permitting and preventing flow of medical fluids to the patient during operation of the medical fluid delivery system 102. In one approach, the valves 120 include first interface adaptations 134 for interfacing (e.g. matably receiving and/or engaging) with a valve operation system 140 of the present invention to accomplish the first and second degrees of occluding of the medical fluid flow. In one aspect, a first degree of occluding may substantially or completely occludes fluid flow through a medical fluid line. In one aspect, a second degree of occluding may partially non-occlude (e.g., impede) or completely non-occlude (allow) fluid flow through a medical fluid line.

Figure 3:
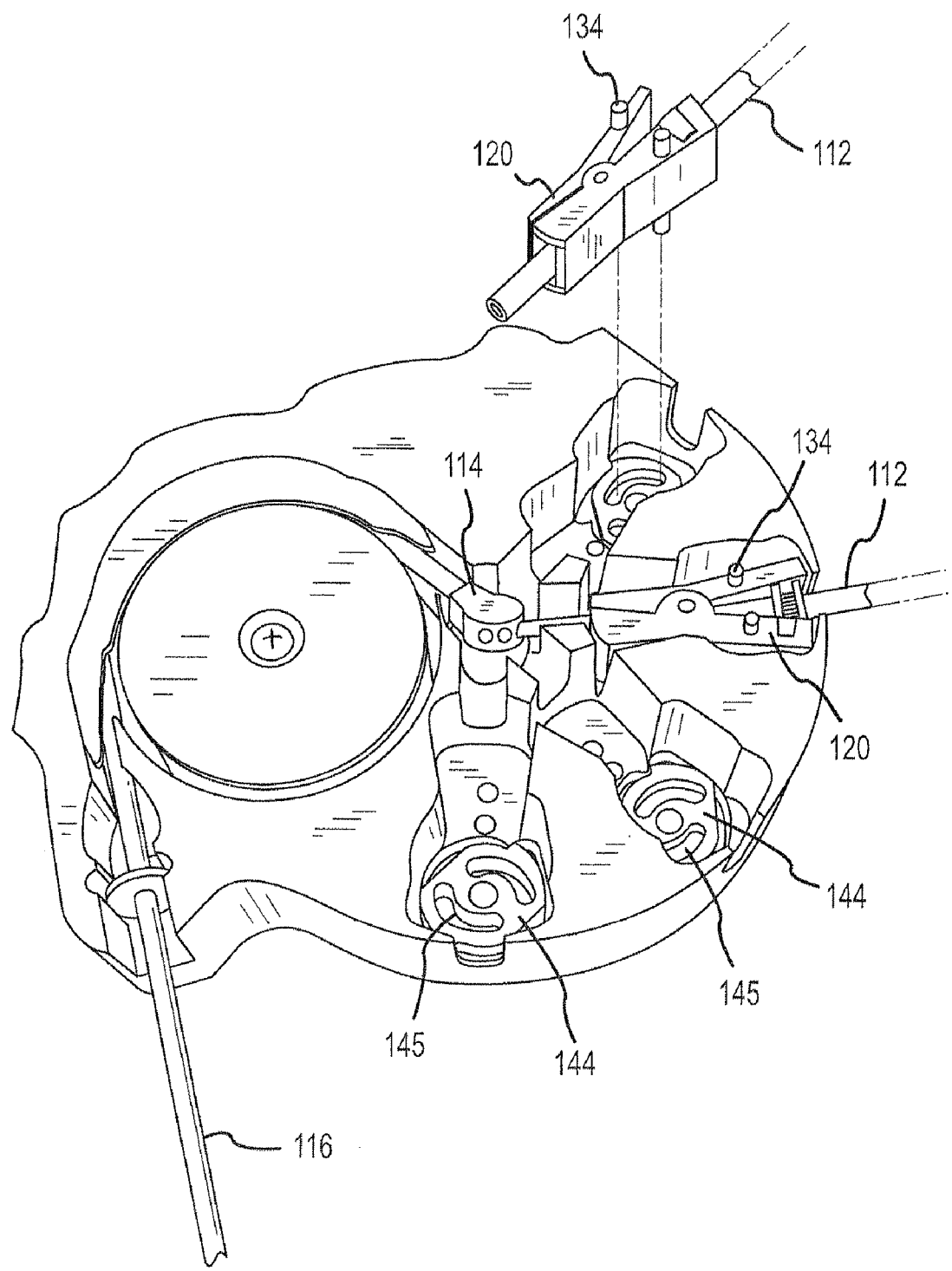
FIG. 3 is a schematic view of one embodiment of the medical fluid line set and valve operating system of the present invention.

One embodiment of the interface of the medical fluid line set 110 with the valve operating system 140 is depicted in FIG. 3. As noted, one or more of the medical fluid delivery lines 112 may be received by one or more valves 120. The one or more valves 120 may include first interface adaptations 134 for interfacing (e.g. matably receiving and/or engaging) with the valve operating system 140. In one approach, the first interface adaptations 134 may be protrusions, such as pins.

As used herein, "matably receiving" and like terms define a situation where the first interface adaptation is sized to receive, or be received by, a second interface adaptation, but the first and second interface are not necessarily in physical communication. In some instances, as described in further detail below, it may be desirable to size the first and second adaptations such that they may easily receive one another, but are not in physical communication in a first position.

Also, as used herein, "matably engaging" and like terms define a situation where the first interface adaptation is in physical communication with said second interface adaptation, such as when the second interface adaptation has moved from a first position to a second position (e.g. via the valve controller) and is exerting a force on the first interface adaptation.

The valve operating system 140 generally comprises a valve controller, as described in further detail below, and a plurality of valve interface members, which may comprise valve actuators 144. The valve actuators 144 generally comprise second interface adaptations 145 for matably receiving and/or engaging with the first interface adaptations 134 of the valve 120 (e.g. via a male-female arrangement). In one approach, the second interface adaptations 145 may be openings, such as slots.

In one embodiment, the one or more medical fluid delivery lines 112 are interconnected with (e.g. fixedly interconnected with) the valves 120 and interfaced with the valve operation system 140, which includes valve actuators 144 which may interface with the valves 120. As will be discussed in further detail below, the interface between the disposable medical fluid line set 110 and the valve operation system 140, via the valves 120 and the valve actuators 144, enables the medical fluid delivery system 102 to deliver multiple medical fluids, either in serial or parallel, to a single patient using a single pumping system. For example, at least one first interface adaptation 134 may be engaged by at least one second interface adaptation 145, whereby the valve operating system 140, via a valve controller, controls a force applied to the at least one first interface adaptation 134 by the at least one second interface adaptation 145. This force causes at least one valve 120 to move from a closed to at least a partially open position, and permit fluid flow through one or more corresponding at least one medical fluid delivery lines 112. In another approach, the first interface adaptations 134 may be engaged by the second interface adaptations 145, whereby the valve operating system, via a valve controller, controls a force applied to the first interface adaptations 134 by the second interface adaptations 145, which causes the valve 120 to move from at least a partially open position to a closed position, and substantially or completely occludes fluid flow through a corresponding medical fluid delivery line 112.

In one approach, all the valves 120 of the medical fluid delivery system 102 may be adapted to cooperatively interface with all of the valve actuators 144 of the medical fluid delivery system 102. For example, all the valves 120 could be sized to matably receive and/or engage any of the valve actuators 144, and vice-versa. In one embodiment, all the valves 120 comprise the same first interface adaptations 134 and all the valve actuators 144 comprise the same second interface adaptations 145, wherein all the first interface adaptations 134 are sized to matably receive and/or engage any of the second interface adaptations 145. Further in this regard, all the recesses and/or ports within a housing of the medical fluid delivery system may be sized to receive any of the valves 120, valve actuators 144, and/or medical fluid delivery lines 112. Such an approach enables the valves 120 and valve actuators 144 to be used interchangeably within the medical fluid delivery system 102, irrespective of location within the medical fluid delivery system and irrespective of which medical fluid is connected to a specific medical fluid delivery line 112.

In another aspect, the medical fluid delivery lines 112, the valves 120, the valve actuators 144 and/or other components of the medical fluid delivery system (e.g., portions of a housing such as recesses or ports) may include a human sensory engagement descriptor (e.g., a color code), such as by including a color designation located on the surface of such items. In this regard, certain colors may be utilized by (e.g., included on the surface of) certain medical fluid delivery lines 112, valves 120 valve actuators 144 and/or other components of the medical fluid delivery system to correspond with one another and/or a certain medical fluid (e.g., a certain drug solution). Thus, a user of the medical fluid delivery lines 112, valves 120, valve actuators 144 and/or other components of the medical fluid delivery system may be able to easily connect various component in relation to the color codes.

Figure 4:
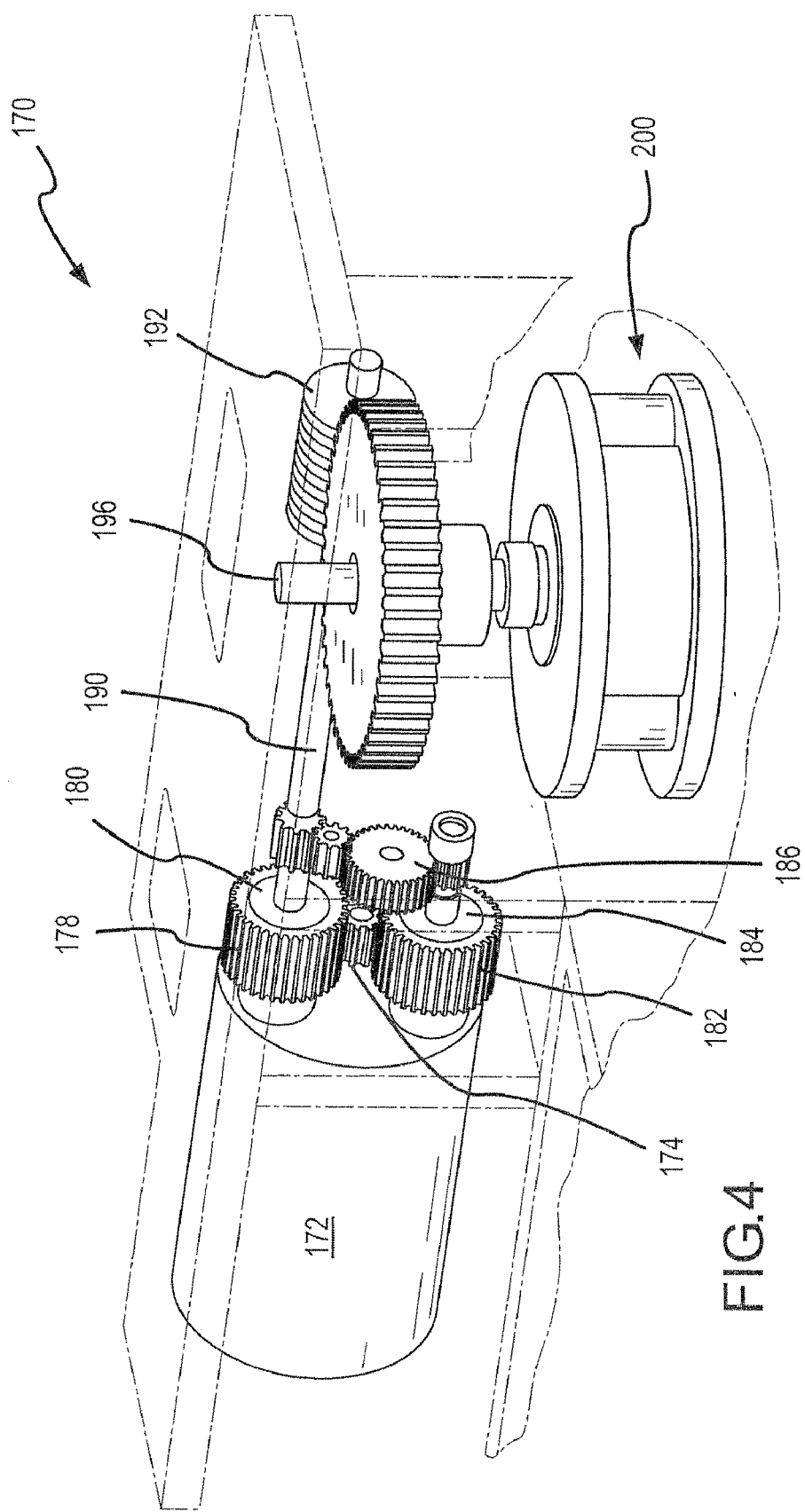
FIG. 4 is a schematic view of one embodiment of the pumping system of the present invention.

The medical fluid delivery system 102 of the present invention also may include a pumping system 170 adapted to deliver medical fluids to a patient, which will now be described further in reference to FIG. 4. The pumping system 170 generally comprises a bi-directional drive member mechanically interfaced with a pump drive member via a transmission for driving the medical fluid pump. The bi-directional drive member, transmission and pump drive member are generally interfaced and adapted such that movement of the bi-directional drive member in a first direction imparts a first output to the pump drive member, thereby causing a portion of it (e.g., the output shaft 190) to move in one direction. The bi-directional drive member, transmission and pump drive member are also generally interfaced and adapted such that movement of the bi-directional drive member in a second direction imparts a second output to the pump drive member, also causing the pump drive member (e.g., the output shaft 190) to move in the same one direction.

For example, and as will be described in further detail below, the bi-directional drive member generally may comprise a bi-directional drive motor 172 mechanically interfaced with motor gear 174. The first motion transfer member may comprise a first gear 178 mechanically interfaced with the motor gear 174 and a first one-way clutch 180, whereby operation of the bi-directional drive member in the first direction drives the first gear 178 and first one-way clutch 180 to move the output shaft 190 in the one direction. The second motion transfer member may also comprise a second gear 182 mechanically interfaced with the motor gear 174 and a second one-way clutch 184. However, while operation of the bi-directional drive member in the first direction drives the second gear 182, the second one-way clutch 184 is interfaced with the second gear 182 such that no significant motion is produced (e.g., the second one-way clutch 184 slips) and a mechanical output from the second motion transfer member is not imparted to the output shaft 190.

Conversely, when the bi-directional drive member is operated in the second direction to produce the second output, the first gear 178 is driven, but the first one-way clutch 180 is interfaced with the first gear 178 such that no significant motion is produced (e.g., the first one-way clutch 180 slips) and a mechanical output from the first motion transfer member is not imparted to the output shaft 190. However, when the bi-directional drive member is operated in the second direction, the second gear 182 and a second one-way clutch 184 are driven, and a mechanical output is provided from the second motion transfer member to the output shaft 190 via the at least one additional transmission gear 186 to drive the output shaft 190 in the same one direction.

As will be appreciated, the arrangement of the bi-directional drive member, transmission and pump drive member enables the medical fluid delivery system to operate over a wide range of speeds and corresponding fluid flow delivery rates using a single pump 200. As will be described in further detail below, this novel arrangement can enable the delivery of medical fluids over a wide variety of flow ranges, for example from 0.1 ml per hour to 2000 ml per hour.

Figure 5:
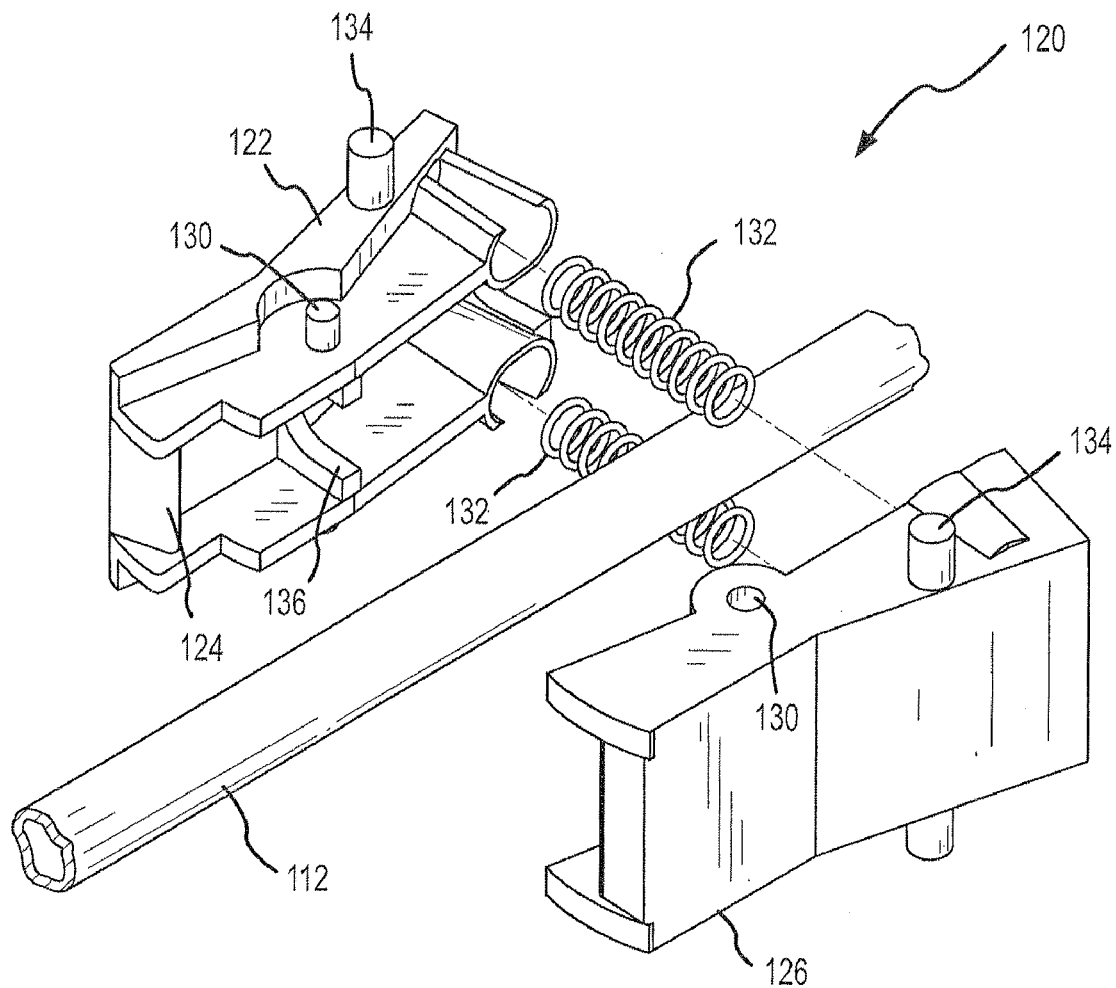
FIG. 5 is a perspective view of one embodiment of a valve of the present invention.
Figure 6:
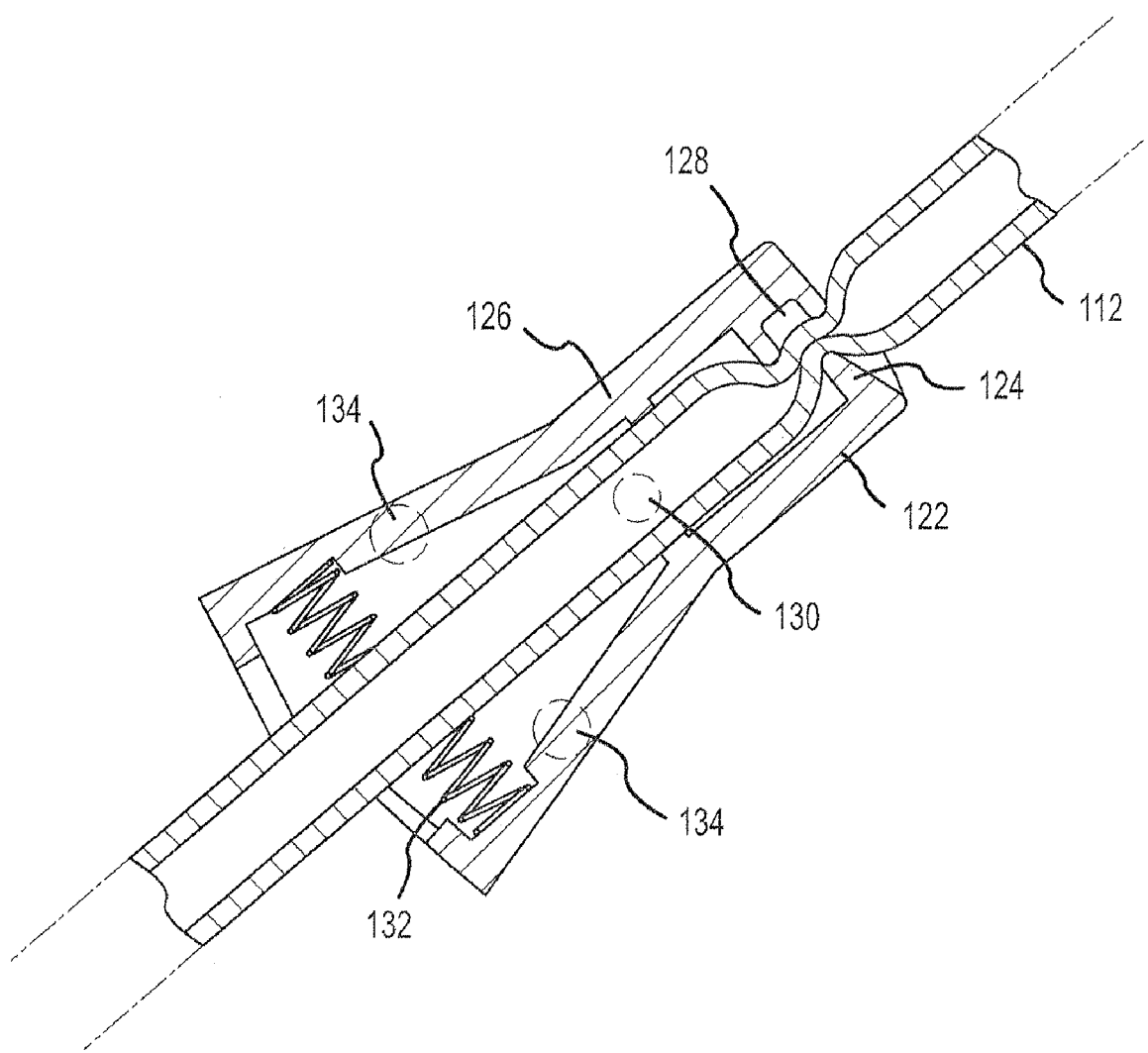
FIG. 6 is a cross-sectional view of one embodiment of a valve of the present invention.

As noted above, the medical fluid delivery system 102 may include a disposable medical fluid line set 110, which may include valves 120, which are now described in further detail with reference to FIGS. 5 and 6. Each valve 120 generally comprises elongated members 122, 126. The elongated members 122, 126 are generally interfaced about one or more pivot points 130, and may be biased at one end by one or more biasing means 132, such as by one or more springs. In one approach, the biasing means 132 is included within the valve 120 such that the valve 120 is in a normally-closed position to substantially or completely occlude fluid flow through the medical fluid delivery line 112. In another approach, the biasing means is included within the valve 120 such that the valve in a normally open position to permit fluid flow through the medical fluid delivery line.

In a particular embodiment, a first elongated member 122, may comprise at least one rib 124, and the second elongated member may comprise at least one valley 126. In the normally-closed approach, the at least one rib 124 and at least one valley 128 are normally interfaced. In this approach, when a medical fluid delivery line 112 is received by the valve 120, the at least one rib 124 and at least one valley 128 will pinch the medical fluid delivery line 112 such that fluid flow is substantially or completely occluded. However, in an at least partially open position, the at least one rib and 124 at least one valley 128 will at least not fully pinch the medical fluid delivery line 112, which may permit some fluid flow through the medical fluid delivery line 112.

In the normally-open approach, the at least one rib 124 and at least one valley 128 are normally not interfaced. In this approach, when a medical fluid delivery line 112 is received by the valve 120, fluid flow will be at least partially non-occluded or completely non-occluded in a normally open position, but will be substantially or completely occluded in the closed position by interface of the at least one rib 124 and at least one valley 128 with the medical fluid delivery line 112.

In one embodiment, when the medical fluid delivery line 112 is pinched by the at least one rib 124 and at least one valley 128, the medical fluid delivery line 112 is contacted by the at least one rib 124 and at least one valley 128 in at least three points. Contacting the medical fluid delivery line 112 in at least three points may insure substantial or complete occlusion of fluid flow through the medical delivery line 112, thereby preventing fluid flow to the patient P.

In another embodiment, the valve 120 may include guide members 136 for receiving a medical fluid delivery line 112. The guide members 136 may be used to retain the medical fluid delivery line 112 in the proper place within the valve 120.

In one aspect, at least one of the first and second elongated members includes first interface adaptations 134 for interfacing (e.g. matably receiving and/or engaging) with the valve operating system 140, as described in further detail below. In one embodiment, the first interface adaptation 134 may be a protrusion or opening. In the case of a protrusion, the first interface adaptation 134 may be a pin. In the case of an opening, the first interface adaptations 134 may be a slot. As used herein, the terms opening and protrusion are used broadly to define separate adaptations that complement each other such that they may be matably received and engaged by one another.

In a particular embodiment, the valve 120 comprises first interface adaptations on opposing sides of at least one elongated member. As will be appreciated, such an arrangement enables the valve 120 to be interfaced with the valve actuator 144 in two orientations.

Figure 7A:
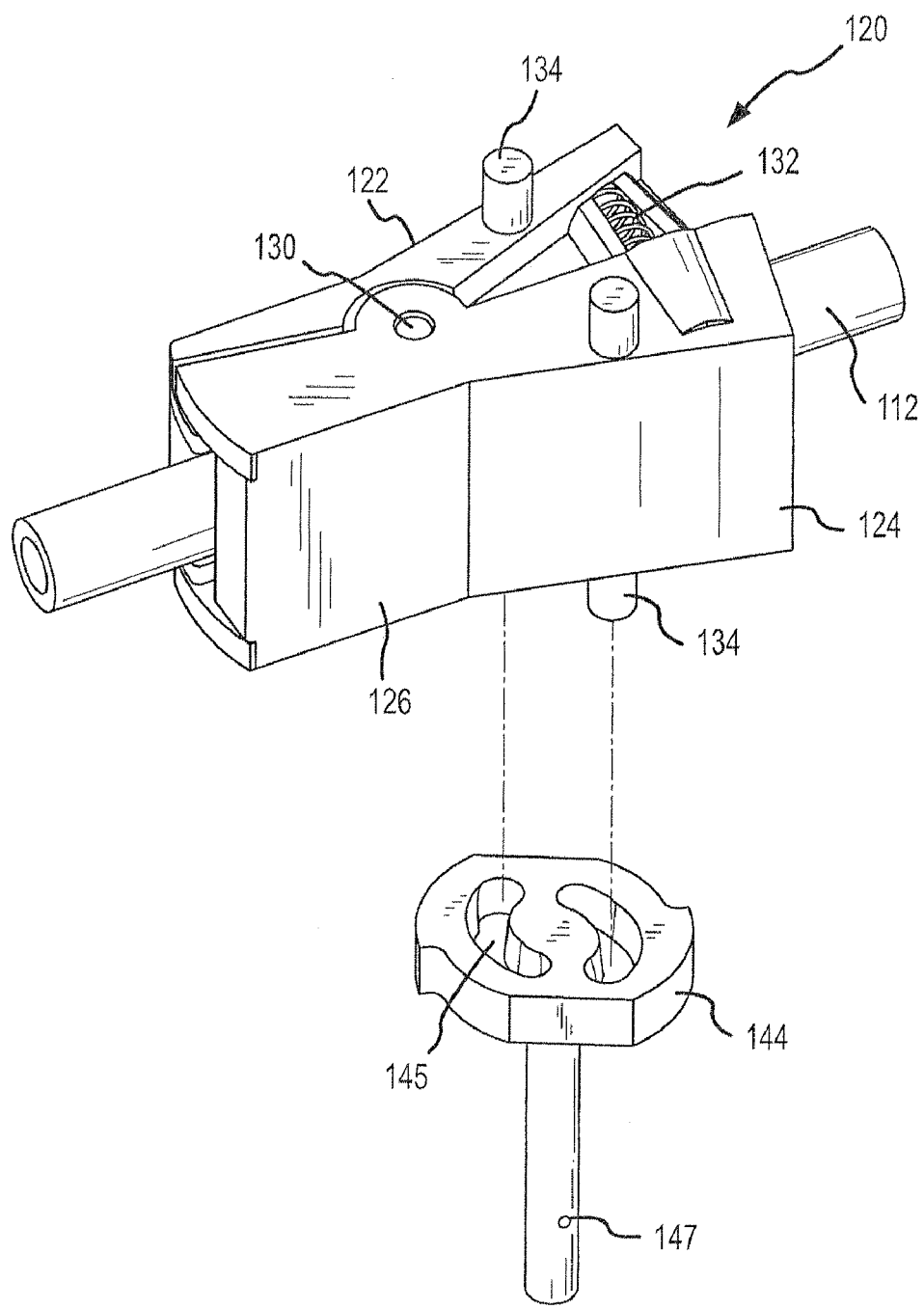
FIG. 7a is a perspective view of one embodiment of a valve and a valve actuator of the present invention.

The interface of the valve 120 with the valve actuator 144 is now described in reference to FIG. 7A. As described above, the valve 120 generally comprises first interface adaptations 134 for matably receiving and/or engaging second interface adaptations 145 of a valve actuator 144. In one approach, the first interface adaptations 134 may be protrusions, such as pins, that are adapted to be received by the second interface adaptations 145 of the valve actuator 144. In this approach, the second interface adaptations 145 may be openings, such as slots, that are adapted to be received by the protrusions of the first interface adaptations 134. In another approach, the first interface adaptations 134 may be openings, such as slots, that are adapted to be received by the second interface adaptations 145 of the valve actuator 144. In this approach, the second interface adaptations 144 may be protrusions, such as pins, that are adapted to be received by the openings of the first interface adaptations 134. In one aspect, the valve 120 comprises at least two first interface adaptations 134 and the valve actuator 144 comprises at least two second interface adaptations 145 for matably receiving and/or engaging the at least two first interface adaptations 134.

In operation, and as will be described in further detail below, a valve controller 154 actuates the valve actuator 144, thereby causing the second interface adaptations 145 to engage the first interface adaptations 134. The engagement of the first interface adaptations 134 by the second interface adaptations 145 results in a force on first interface adaptations 134. This force generally causes the biasing means 132 to compress, which forces the biased ends of the elongated members 122, 126 to be brought at least partially closer together. The other ends of the elongated members 122, 126 are consequently moved at least partially further apart from one another.

In one approach, ribs 124 and/or valleys 128 are located on the nonbiased ends of the elongated members 122, 126. In this approach, when the valve actuator 144 engages the first interface adaptations 134 via second interface adaptations 145 and forces the biased ends of the elongated members 122, 126 at least partially closer together, the ribs 124 and/or valleys 128 are at least partially moved out of an interfaced position, where some medical fluid may flow through the medical fluid delivery line 112. This embodiment is generally known as a normally-closed valve approach, as described above. The utility of this approach will be appreciated in that any displacement, whether intentional or accidental, of the valve 120 from the valve actuator 144 will result in the valve 120 closing, thereby substantially or completely occluding fluid flow through the medical fluid delivery line 112. Thus, any intentional or accidental displacement of the valve 120 from the valve actuator 144 will result in the medical fluid delivery system 102 preventing medical fluid flow to the patient 106.

In another approach, ribs 124 and/or valleys 128 are located on the biased ends of the elongated members 122, 126. In this approach, when the valve actuator 144 engages the first interface adaptations 134 via the second interface adaptations 145 and forces the biased ends of the elongated members 122, 126 at least partially closer together, the ribs 124 and/or valleys 128 are moved into an at least partially interfaced position, where less or no medical fluid may flow through the medical fluid delivery line 112. This embodiment is generally known as a normally-opened valve approach, as described above.

Figure 7B:
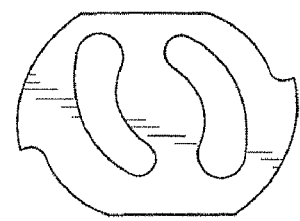
FIG. 7b is a top view of one embodiment of a valve actuator of the present invention.

As noted above, the valve actuator generally comprises a second interface adaptation, which may comprise an opening or a slot. In a particular embodiment, depicted in FIG. 7b, the second interface adaptation 745 is a slot that includes a wide proximal end for matably receiving the first interface adaptation, a narrow distal end, and an arcuate path between the wide proximal end and the narrow distal end, where at least a portion of the path tapers from the wide proximal end to the narrow distal end. In this particular embodiment, the first interface adaptation is sized may be engage the slot and a point along the arcuate path.

The interface of the valve actuators 144 with the valve controller 154 in the valve operating system 140 will now be described in reference to FIG. 8. Each valve actuator 144 is generally one component of a valve interface member 142. Each valve interface member 142 may generally comprise a valve actuator 144, an actuator return member 150, an actuator clutch 148 and actuator gear 146. The valve actuator 144 may be mechanically interfaced with an actuator return member 150 (e.g., a torsion spring), which may be interfaced with a stationary position 149. The actuator gear 146 is generally interfaced with an actuator clutch 148.

The actuator gear 146 and actuator clutch 148 are generally interfaced such that motion of the actuator gear 146 in a first direction will engage the actuator clutch 148, thereby imparting motion to valve actuator 144 such that the valve actuator 144 is moved from a starting position to a second position. Conversely, motion of the actuator gear 146 in a second direction will not engage the clutch 148, and motion to valve actuator 144 will not be imparted. It will be appreciated that the above-referenced second position of the valve actuator may be any position of the full range of movement of the valve actuator 144, excluding the starting position.

The actuator return member 150 (e.g., a torsion spring) is generally mechanically interfaced with the valve actuator 144 via a hole 147 on the valve actuator shaft, where a proximal end of the actuator return member is interlocked with the hole 147. The actuator return member 150 is also generally mechanically interfaced with a stationary portion 149, where a distal end of the actuator return member 150 is interlocked with a portion of a stationary portion 149 (e.g., a hole in a housing).

In operation, when the actuator gear 146 is moved in a first direction, the actuator clutch 148 is engaged by the actuator gear 146 and the valve actuator 144 is moved in corresponding relation thereto from a starting position to a second position. When the actuator gear 146 no longer engages the actuator clutch 148, the actuator return member 150 imparts a force on the valve actuator 144, thereby causing the valve actuator to return from the second position to the starting position. Thus, in relation to a valve 120, the second interface adaptations 145 engage the first interface adaptations 134 when the actuator clutch 148 moves the valve actuator 144, and act to operate the valve 120, as described above. Moreover, when the actuator gear 146 no longer engages actuator clutch 148, the second interface adaptations 145 of the valve actuator 144 no longer engage the first interface adaptations 134, and the valve actuator 144 will be returned to a starting position by the actuation return member 150. Corresponding thereto, the valve 120 will also be returned to a normally closed or normally opened position, as described above. In one aspect, the valves 120 and valve actuators 144 are interfaced such that the valves 1209 are loose in the starting position.

Figure 8:
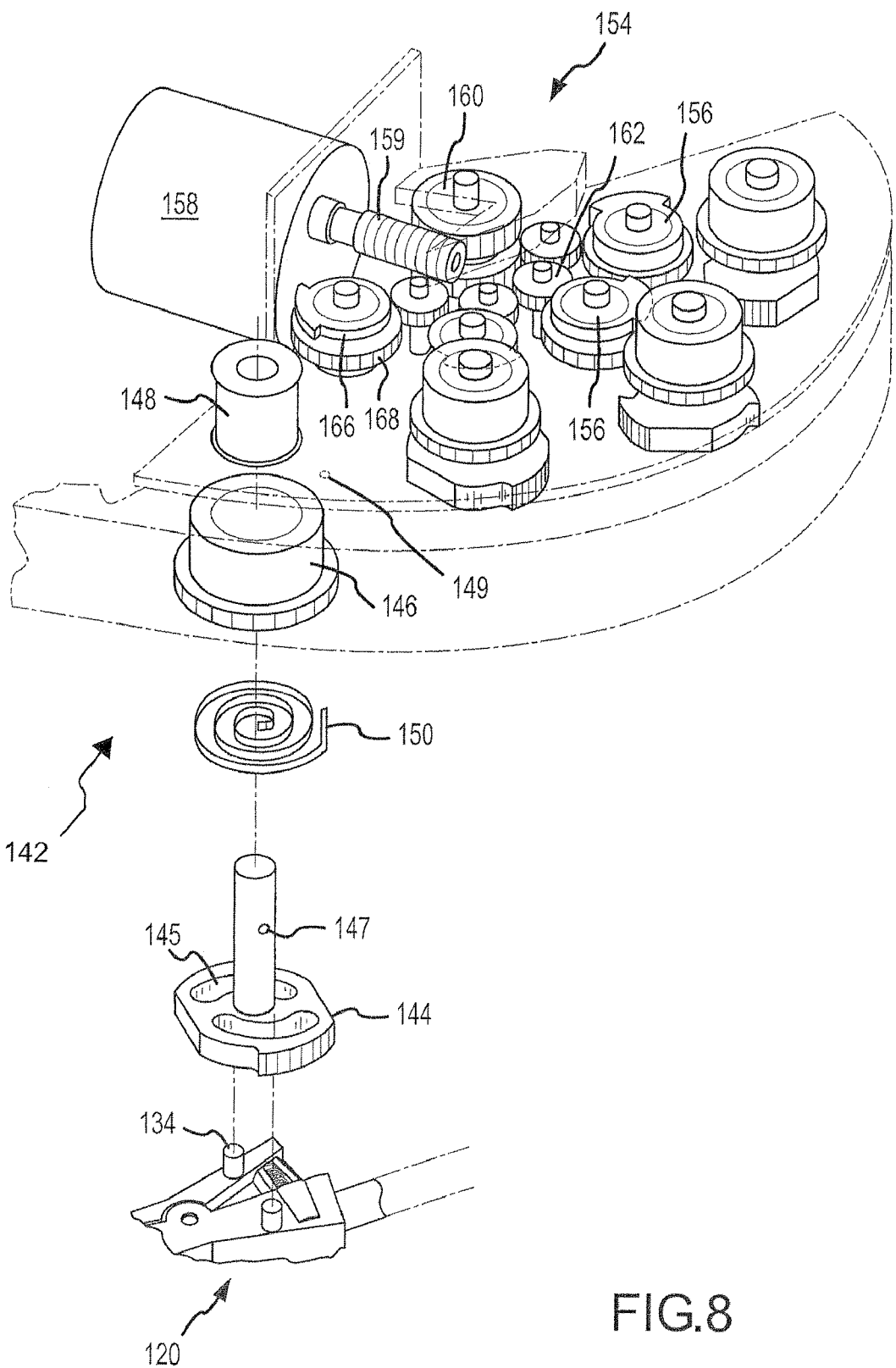
FIG. 8 is a perspective view of one embodiment of a valve operating system of the present invention.

With continued reference to FIG. 8, each valve interface member 142 is generally interfaced with the valve controller 154. The valve controller 154 generally comprises a central motion transfer member and a plurality of activation members 156. The central motion transfer member may include a drive motor 158, a drive motor gear 159, a central drive gear 160 and at least one additional central gear 162. The drive motor 158, motor gear 159 and central drive gear 160 are generally mechanically interfaced such that motion of the drive motor 158 will be imparted to the central drive gear 160 via the motor gear 159. In one aspect, the central drive gear 160 directly imparts mechanical motion to the plurality of activation members 156. In another aspect, the at least one additional central gears 162 may be provided to transfer mechanical motion from the central drive gear 160 to the plurality of activation members 156. Generally, the at least one additional central gear 162 is utilized to provide sufficient spacing between activation members 156, the valve interface members 142 and/or the central drive member.

Each of the activation members 156 generally comprises a lower section 168. The lower section 168 of each of the activation members 156 is generally interfaced with the central motion transfer member (e.g., via the central drive gear 160). In one approach, the lower section 168 of each activation member includes a plurality of teeth located about the perimeter of the lower section 168 for interfacing with a central drive gear 160. Thus, as the central motion transfer member moves in a first direction, each of the activation members 156 interfaced therewith will be imparted motion (e.g., via lower sections 168 and central gear 160). In one approach, this motion is rotational motion.

Each of the activation members 156 generally also comprises an upper section 166. The upper section 166 of each of the activation members 156 generally comprises an "active" interface portion, adapted to interface with a corresponding actuator gear 146 during, at least, movement of the activation member 156 from a first position to a second position. The upper section 166 of each of the activation members 156 also generally comprises a "inactive" interface portion, which will not interface with the corresponding actuator gear 146 during, at least, movement of the activation member 156 from a third position to a fourth position. In one approach, the active interface portion of the upper sections 166 may be contiguous. In another approach, the active interface portion of the upper sections 166 may be non-contiguous.

Figure 9A:
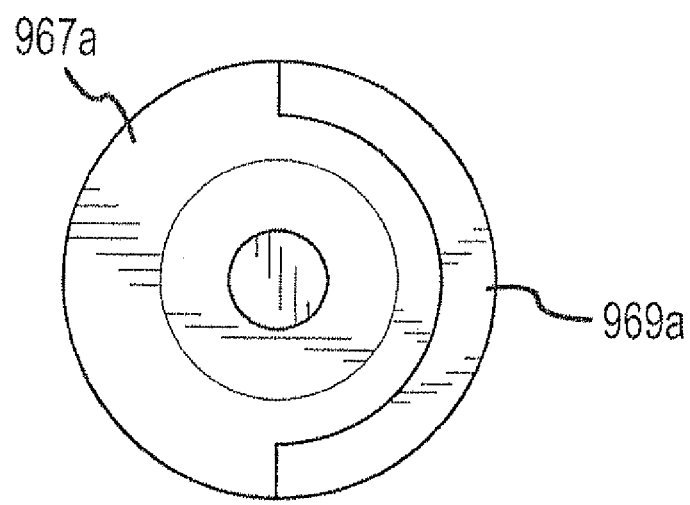
FIG. 9a is a top view of one embodiment of an activation member of the present invention.
Figure 9B:
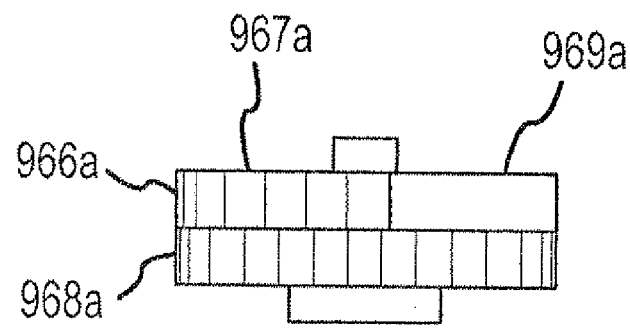
FIG. 9b is a side view of one embodiment of an activation member of the present invention.
Figure 9C:
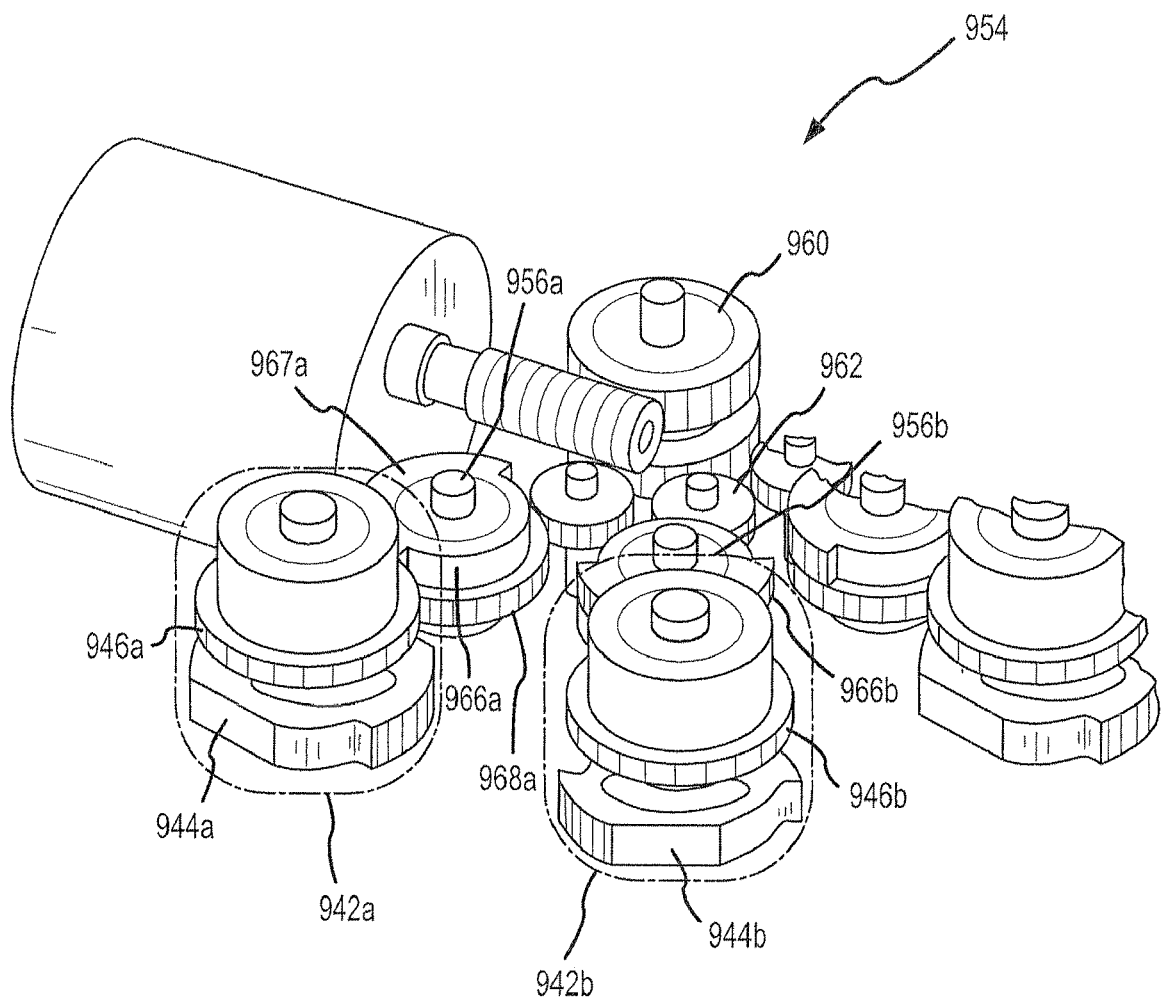
FIG. 9c is a perspective view of one embodiment of a valve operating system of the present invention.

One embodiment of a valve operating system in accordance with the present invention is depicted in FIGS. 9a-9c. In this embodiment, each of the activation members 956a, 956b is in the form of a mutilated gear comprising an upper section 966a, 966b and a lower section 968a, 968b, where each of the lower sections 968a, 968b are interfaced with the central drive gear 960 via additional central gears 962. Thus, as the central drive gear 960 moves, each of the activation members 956a, 956b interfaced therewith, via lower sections 968a, 968b, will be imparted motion. In one approach, this motion is rotational motion.

As a central drive gear 960 moves in a first direction, each of the activation members 956a, 956b interfaced therewith, via the additional central drive gears 962, will also be moved. However, each of the upper sections 966a, 966b of each of the activation members 956 is generally positioned within the valve controller in relation to a corresponding one valve interface member 942a, 942b, (e.g., via the above-described actuator gears) such that less than all of the valve interface members 942 will be activated in relation to a particular output of the central drive gear 960. That is, the active interface portion 967a of a first active member 956a is positioned within the valve controller 954 such that it may interface with a corresponding first valve interface member 942a during movement of the central drive gear 960 from a first position to a second controller position (e.g. a first motion output), and the active interface portion 967b of a second active members 956b is positioned within the valve controller 954 such that it may interface with a corresponding second valve interface member 942b during movement of the central drive gear 960 from a third controller position to a fourth controller position (e.g. a second motion output).

As used herein, the term "motion output", in reference to the valve controller of the valve operating system, means of a portion of the valve controller is interfaced with a portion of a corresponding valve interface member, and may be imparting motion to the valve interface member. For example, a first motion output of the valve controller means the valve controller is interfaced with a corresponding first valve interface member. A second motion output of the valve controller means the valve controller is interfaced with a corresponding second valve interface member. In this regard, the valve controller may be interfaced with the interface members, such that the motion outputs (e.g., first and second motion outputs) are non-overlapping. Further, the first motion output and second motion output may result in coincidental motion of the first and second valve interface members, respectively.

Thus, as the first interface member 942a is interfaced with the first activation member 956a, its corresponding valve actuator 944a will be activated (e.g., actuated), and the corresponding valve associated therewith will be at least partially opened or closed, as described above. As the second interface member 942b is interfaced with the second activation member 956b, its corresponding valve actuator 944b will be activated (e.g., actuated), and the corresponding valve associated therewith will be at least partially opened or closed, as described above.

Referring back to FIG. 8, in one approach, the valve interface members 142 and activation members 156 are arranged within the valve operating system 154 such that the motion of a first interface member does not overlap with the motion of a second interface member. That is, when a first interface member is actuated via a first activation member (e.g. via a first motion output of the valve controller), thereby acting on a corresponding first valve via corresponding first valve actuator, a second interface member is not actuated via its corresponding second activation member, thereby leaving a corresponding second valve in its normal position (e.g., a normally-opened or normally-closed position).

In another approach, the interface members 142 and activation members 156 are sized and arranged within the valve controller 154 such that the motion of a first interface member partially overlaps with the motion of a second interface member. That is, when a first interface member is actuated via a first activation member (e.g. via a first motion output of the valve controller), thereby acting on a corresponding first valve via corresponding first valve actuator, a second interface member is also at least partially actuated via its corresponding second activation member, thereby coincidentally also acting on its corresponding second valve via corresponding second valve actuator.

As will be appreciated, the central drive member and the valve interface members may be sized and arranged in any configuration to achieve the desired opening and closing of a plurality of valves in the medical fluid delivery system of the present invention. For example, the valve controller may be configured to operate 2, 3, 4, 5, 6, 7, 8, 9, 10 or even more valves (and any multiple thereof) associated with a medical fluid delivery system, either in serial or parallel, and in any combination, sequence or order. It will be appreciated that the number of valve interface members will generally correspond to the number of valves desired to be operated. Thus, if the medical fluid delivery system requires the operation of 6 valves, 6 valve interface members would be generally be required, although different configurations utilizing less or more valve interface members is possible.

Moreover, it will be appreciated that if it is desired to operate each of the valves independently, the upper sections of 166 of the active members 156 should be sized, adapted and configured within the valve controller in relation to the number of valves associated with the medical fluid delivery system. Generally, this may be accomplished by relating the number of valves desired to be opened to the full rotation (360°) of the central drive member. For example, if the medical fluid delivery system is designed to operate two valves, then 180° (360°/2) of rotation should be reserved by the central drive gear 160 for each active member 156. In such a case, the upper sections 166 of each of the active members 156 would comprise active interface portions over not more than half of the upper sections 166 and inactive interface portions over no more than the other half of the upper sections 166.

In a medical fluid delivery system designed to operate 3 valves, then 120° (360°/3) of rotation should be reserved by the central drive gear 160 for each active member 156, and the upper sections 166 of each the active members 156 should comprise active interface portions over no more than one-third of the upper section 166.

In a medical fluid delivery system designed to operate 4 valves, then 90° (360°/4) of rotation should be reserved by the central drive gear 160 for each active member 156, and the upper sections of each active members should comprise active interface portions over no more than one quarter of the upper sections 166.

In a medical fluid delivery system designed to operate 5 valves, then 72° (360°/5) of rotation should be reserved by the central drive gear 160 for each active member 156, and the upper sections of each active members should comprise active interface portions over no more than one-fifth of the upper sections 166.

In a medical fluid delivery system designed to operate 6 valves, then 60° (360°/6) of rotation should be reserved by the central drive gear 160 for each active member 156, and the upper sections of each active members should comprise active interface portions over no more than one-sixth of the upper sections 166.

In a medical fluid delivery system designed to operate 7 valves, then about 51.4° (360°/7) of rotation should be reserved by the central drive gear 160 for each active member 156, and the upper sections of each active members should comprise active interface portions over no more than one-seventh of the upper sections 166.

In a medical fluid delivery system designed to operate 8 valves, then 45° (360°/8) of rotation should be reserved by the central drive gear 160 for each active member 156, and the upper sections of each active members should comprise active interface portions over no more than one-eighth of the upper sections 166.

In a medical fluid delivery system designed to operate 9 valves, then 40° (360°/8) of rotation should be reserved by the central drive gear 160 for each active member 156, and the upper sections of each active members should comprise active interface portions over no more than one-ninth of the upper sections 166.

In a medical fluid delivery system designed to operate 10 valves, then 36° (360°/10) of rotation should be reserved by the central drive gear 160 for each active member 156, and the upper sections of each active members should comprise active interface portions over no more than one-tenth of the upper sections 166.

As will be appreciated, the medical fluid delivery system may be designed to operate more than 10 valves, and corresponding calculations as those provided above may be utilized to relate the number of valves interface members to the degrees of rotation required to be reserved by the central transfer member, as well as the amount of active interface portions on the upper sections of each of the activation members.

Another aspect of enabling independent valve operation is the arrangement of the activation members 156 within the valve controller 154 in relation to each other. As will be appreciated, if it is desired to operate each valve independently, the upper sections 166 of each of the active members 156 should be arranged within the valve controller such that each upper section 166 engages their respective valve interface member 142 over a specific range (e.g., 90°) of the entire range (e.g., 360°) of the central transfer member. Moreover, as will be appreciated, the valve interface members, its valve activation members and their relative components should be sized accordingly in relation to the number of such members used in the valve control system.

For example, in a medical fluid delivery system comprising four valves, the upper section 166 of a first activation member should engage the first valve interface member over a first quarter of movement of the central transfer member (e.g., the first 90° of rotation of a central drive gear 160). The upper section 166 of a second activation member should engage the second valve interface member over a second quarter of movement of the central transfer member (e.g., the second 90° of rotation of a central drive gear 160). The upper section 166 of a third activation member should engage the third valve interface member over a third quarter of movement of the central transfer member (e.g., the third 90° of rotation of a central drive gear 160). The upper section of a fourth activation member should engage the third valve interface member over a fourth quarter of movement of the central transfer member (e.g., the fourth 90° of rotation of a central drive gear 160). As noted above, in such an embodiment, each of the upper sections 166 should comprise active interface portions over no more than a quarter of their respective upper sections 166. This arrangement will enable the actuation of each of the four valves independently from each other. It will be appreciated that similar arrangements for medical fluid delivery systems comprising 2, 3, 5, 6, 7, 8, 9, and 10 or more valves may be implemented using the above-referenced methodology.

In another approach, the medical fluid delivery system may be configured with a valve operating system that enables two or more valves to be operated simultaneously. It will be appreciated, that variations of the above-described methodology may be employed to achieve such simultaneous valve operation. For example, in a medical fluid delivery system comprising 4 valves, the valve operating system could be adapted such that first and second valves open simultaneously and independently of the opening of the third and fourth valves, which may or may not open simultaneously. In such a case, the first and second activation members may be identical and arranged within the valve operating system, such that their respective upper active members each engage their respective valve interface members over a first portion of movement of the central transfer member (e.g., the first 120° of rotation of the central drive gear 160). Likewise, the third activation member may be adapted and arranged within the valve operating system such that its upper active member engages its respective valve interface member over a second portion of movement of the central transfer member (e.g., the second 120° of the rotation of the central drive gear 160). The fourth activation member may be adapted and arranged within the valve operating system such that its upper active member engages its respective valve interface member over a third portion of movement of the central transfer member (e.g., the third 120° of rotation of the central drive gear 160). It will be appreciated that similar arrangements for medical fluid delivery systems comprising 2, 3, 5, 6, 7, 8, 9, and 10 or more valves may be implemented using the above-referenced methodology to achieve simultaneous valve operation.

As noted, the central motion transfer member may comprise a drive motor 158 to impart motion to each of the active members of the valve controller. In one embodiment, the drive motor 158 of the valve controller 154 is a unidirectional drive motor adapted to impart motion to the central drive gear 160 via the motor gear 159, whereby the central drive gear 160 may be driven in one direction. In another embodiment, the drive motor 158 of the valve controller 154 is a bi-directional drive motor adapted to impart motion to the central drive gear 160 via the motor gear 159, whereby the central drive gear 160 may be driven in two directions.

In one aspect, the drive motor 158 is a bi-directional motor and the valve controller comprises components to enable selective operation of each valve interface member without operating at least one other valve interface member. As noted above, the actuator gear 146 and actuator clutch 148 are adapted such that movement (e.g., rotation) of the actuator gear 146 in one direction engages the actuator clutch 148, but movement (e.g., rotation) of the actuator gear 146 in a second direction does not engage the actuator clutch 148. This arrangement is particularly useful when operating the valve controller 154 to selectively operate a selected valve interface member 142.

For example, as the bi-directional drive motor of the valve controller 154 moves (e.g., rotates) its motor gear 158 in a first direction (e.g., counterclockwise rotation), a first direction of movement is imparted to each of the actuator gears 146 by their respective activation members 156. In this first direction of movement, the actuator gears 146 and actuator clutches 148 may be arranged such that they do not engage one another. However, as the bi-directional drive motor of the valve controller 154 moves (e.g., rotates) its motor gear 158 in a second direction (e.g., clockwise rotation), a second direction of movement is imparted to each of the actuator gears 146 by their respective activation members 156. In this second direction of movement, the actuator gears 146 and actuator clutches 148 may be arranged such that they engage one another, thereby imparting motion to their associated valve interface members as the bi-directional motor rotates its motor gear 158 about its full range of second direction motion (e.g., clockwise rotation). Thus, to prevent opening one or more valves (e.g., so that medical fluids may not be inadvertently delivered to a patient), it may be desirable to operate the bi-directional motor in the first direction until a specific point is reached, at which time the bi-directional motor is operated in a second direction to open a specific valve or valves, as described in further detail below.

As described above, as the bi-directional drive motor moves in the first direction, each of the actuator gears 146 will be moved in a first direction of movement once they have interfaced with the upper sections 166 of the activation members 156. As the bi-directional drive motor continues to move in the first direction, the actuator gear 146 will no longer be moved in a first direction of movement once the active interface portions of the upper section 166 have moved outside the scope of interface. Thus, stopping the bi-directional motor at a location after the active interface portion of the upper section 166 has moved outside the scope of interface with the actuator gear 146, and then moving the bi-directional motor in the second direction will result in operating the corresponding valve interface member to open only the corresponding valve.

In one approach, the bi-directional motor stops moving in the first direction just proximal to the scope of interface between the active interface portion of the upper section 166 and actuator gear 146. In such an approach, the bi-directional motor is then moved in a second direction to activate the corresponding first interface member 142, and its corresponding valve actuator 144 and valve 120. In this regard, a valve status determination system may be employed with the valve operating system to selectively control the valves of a medical fluid delivery system of the present invention. It will be appreciated that this selective open methodology could be employed with any number of valves and valve interface members depending on the desired arrangement of the valve operating system, as described above. Thus, the medical fluid delivery system of the present invention may be adapted to selectively open one or more valves without opening at least one other valve within the medical fluid delivery system.

In one embodiment, the medical fluid delivery system is operatively interfaced with a valve status determination system, which comprises the necessary components to determine when a portion of each of the valve interface members 142 (e.g., each actuator gear 146) is interfaced with a corresponding activation member 156. Thus, the valve status determination system is operable to help achieve the above described selective valve opening, as will now be described in relation to FIG. 10.

Figure 10:
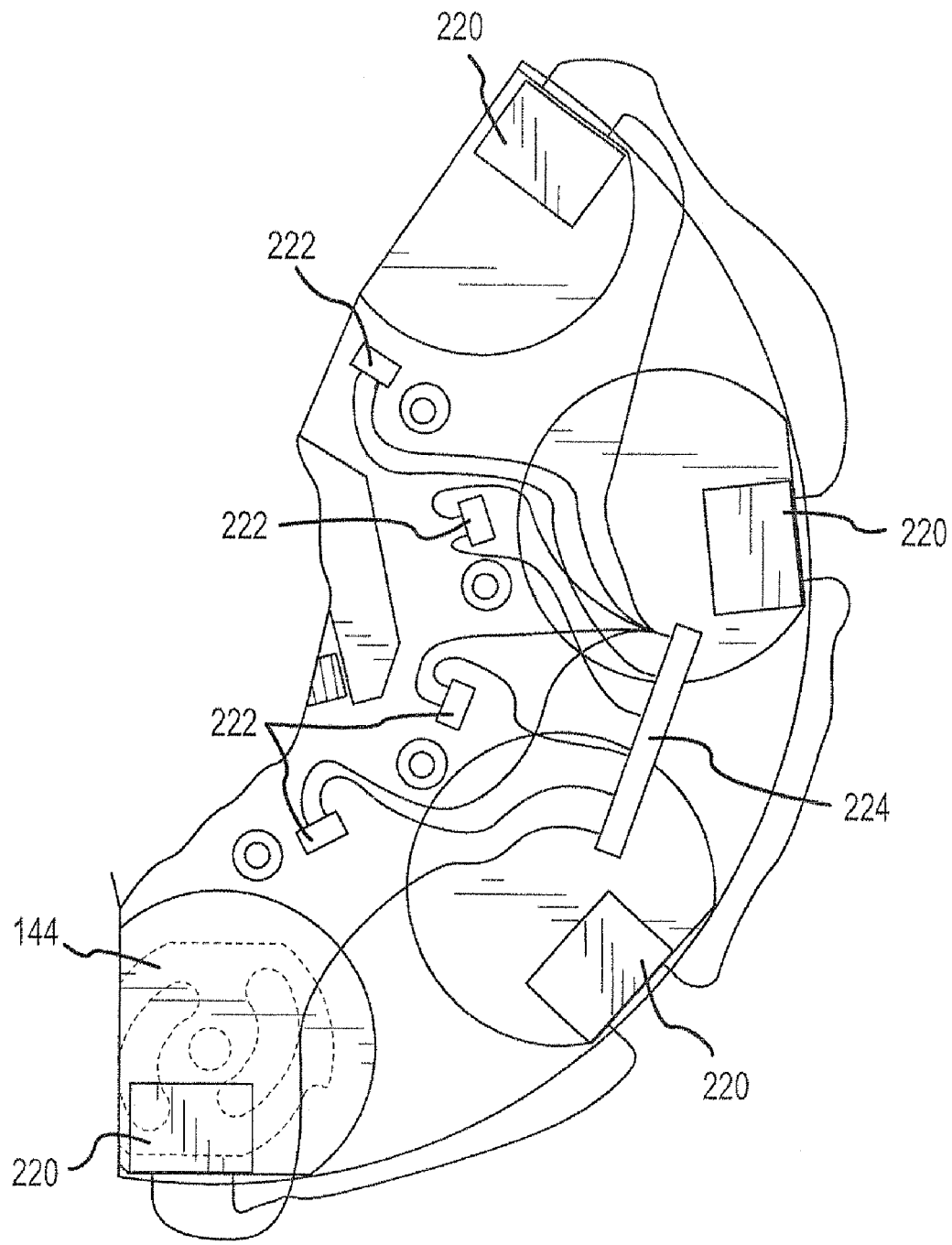
FIG. 10 is a perspective view of one embodiment of a valve status determination system of the present invention.

As depicted in FIG. 10, a medical fluid delivery system may comprise a disposable medical fluid line set 110 interfaced with a valve operating system 140. The medical fluid delivery system may also comprise a valve status determination system, which may comprise components integrated with the valve operating system 140 for the determination of the position of the various components of the valve operating system 140. In one approach, a microswitch 220 for each valve actuator is provided and is adapted to interface with a terminal portion of a corresponding valve actuator 144. In one embodiment, the at least one microswitch 220 is in communication (e.g., mechanical, electrical, magnetic and/or optical communication) with a terminal portion of the corresponding valve actuator 144 when the valve actuator 144 is in a first position. Conversely, the at least one microswitch 220 is not in communication with a terminal portion of the corresponding valve actuator 144 when the valve actuator 144 is a second position. The at least one microswitch 220 may also be in communication (e.g., mechanical, electrical, magnetic and/or optical communication) with other microswitches 220, so that the microswitches 220 may communicate with one another. In one embodiment, the microswitches 220 are interfaced with a communicative connector 224, which may be interfaced with a processor. The processor may be utilized in conjunction with the microswitches 220 to enable selective activation of valves, as described above.

In operation, when at least one microswitch 220 is in communication with a terminal portion of the a corresponding valve actuator 144, it may send signals to the other microswitches 220 and/or communicative connector 224 to communicate the position of the valve associated with the microswitch. In one aspect, the medical fluid delivery system may be configured such that when a terminal portion of a valve actuator 144 is in communication with a corresponding microswitch 220, the communication may indicate the corresponding actuator gear 146 position.

In another aspect, the valve status determination system may also or alternatively comprise microswitches 222 adapted to interface with a terminal portion of a shaft utilized in the activation members 156. In one embodiment, at least one microswitch 222 is in communication (e.g., mechanical, electrical, magnetic and/or optical communication) with a terminal portion of a shaft of the corresponding activation member 156 when the activation member 156 is in a first position. Conversely, the at least one microswitch 222 is not in communication with a terminal portion of a shaft of the corresponding activation member 156 when the activation member 156 is a second position. The at least one microswitch 222 may also be in communication (e.g., mechanical, electrical, magnetic and/or optical communication) with other microswitches 222, so that the microswitches 222 may communicate with one another. In one embodiment, the microswitches 222 are interfaced with a communicative connector 224, which may be interfaced with a processor. The processor may be utilized in conjunction with the microswitches 222 to enable selective activation of valves, as described above.

In operation, when at least one microswitch 222 is in communication with a terminal portion of the shaft of a corresponding activation member 156, it may send signals to the other microswitches 222 and/or communicative connector 224 to communicate the position of its corresponding activation member 156. In one aspect, the medical fluid delivery system may be configured such that when a terminal portion of the shaft of an activation member 156 is in communication with a corresponding microswitch 222, the communication may indicate the position of the corresponding upper section 166 of the activation member 156.

In another aspect, microswitches 220 and 222 may be utilized together to determine the relative positions of each of the actuator gears 146 and upper sections 166 of activation members 156. The use of the microswitches 220, 222, either alone or in combination, in conjunction with a processor, may help the medical fluid delivery system to accomplish the selective opening of individual valves, as described above.

In another embodiment, the valve status determination system may comprise a single sensor operatively interfaced with the central motion transfer member. In this regard, the central motion transfer member may be operable to move over a range of motion (e.g., a full circle, such as in relation to a central drive gear). The single sensor may be adapted to sense the relative position of the central drive member in relation to the range of motion (e.g. the relative position of the central drive gear in relation to a full circle). As the activation members of the valve controller move in corresponding relation to the motion of the central drive member, the sensed position of the central drive member may be used to calculate the relative positions of the valve activation members and/or valve interface members.

Figure 11A:
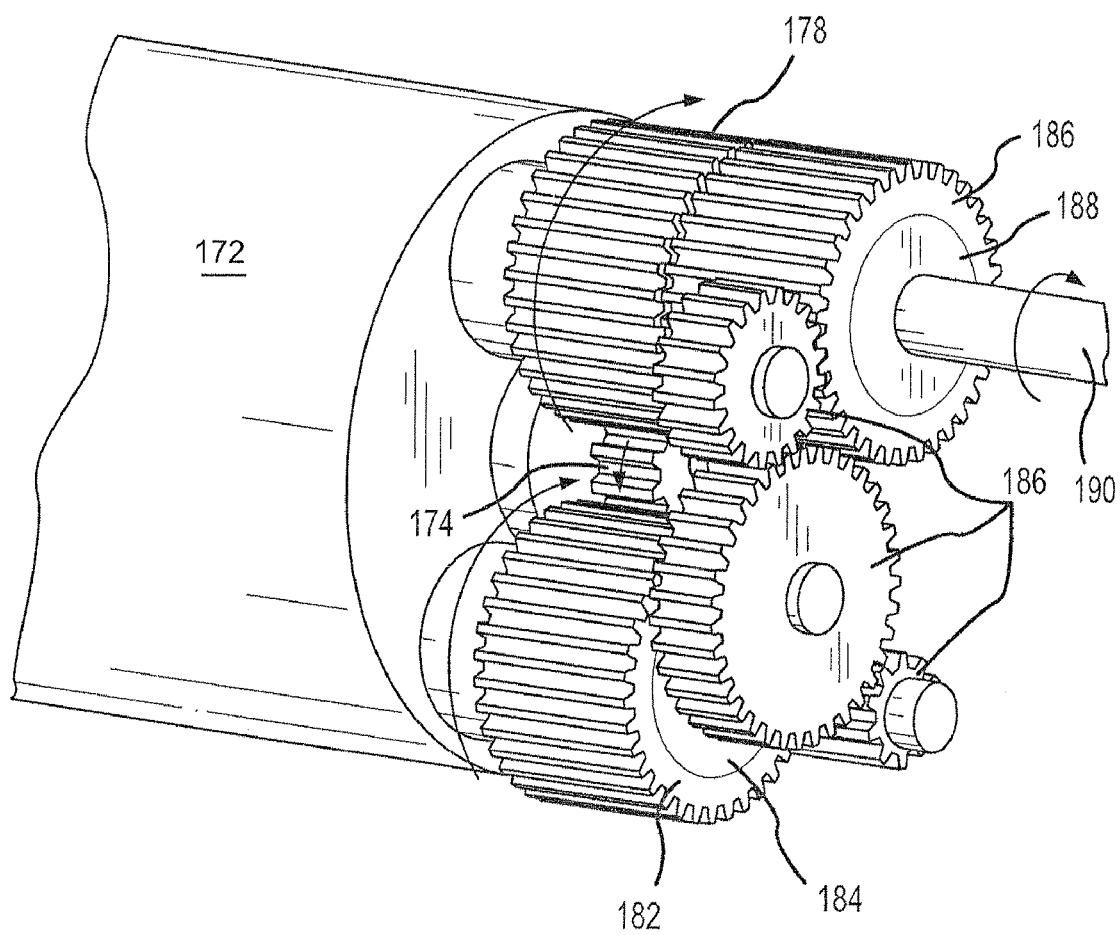
FIG. 11a is a perspective view of one embodiment of a transmission of the present invention.

The medical fluid delivery system 102 of the present invention may also include a pumping system 170, which may include a transmission of the present invention. Referring now to FIG. 11*a*, one embodiment of a transmission useful in accordance with the pumping system 170 of the present invention is depicted. The transmission generally comprises a first motion transfer member (e.g., a first gear 178 and first one-way clutch 180) mechanically interfaced with a bi-directional drive member (e.g., a bi-directional drive motor 172 and a motor gear 174). The transmission also generally comprises a second motion transfer member (e.g., a second gear 182, a second one-way clutch 184, and at least one additional transmission gear 186). Both the first motion transfer member and the second motion transfer member may be mechanically interfaced with the bi-directional drive member and a portion of a pump drive member (e.g., an output shaft 190) for imparting motion to the pump drive member.

The first motion transfer member of the transmission may be any type of device that is adapted to receive and transfer the mechanical output of the bi-directional drive member to the pump drive member, as described above. In one approach, the first motion transfer member includes one or more gears, which may be mechanically interfaced with one or more clutches. In the depicted embodiment, the first motion transfer member includes a first gear 178 mechanically of this of with a motor gear 174 and a first one-way clutch 180 (hidden in this embodiment). The first one-way clutch 180 is mechanically interfaced with an output shaft 190, which is mechanically interfaced with the pump, as depicted previously in FIG. 4.

The second motion transfer member of the transmission may be any type of device that is adapted to transfer the mechanical output of the bi-directional drive member to the pump drive member, as described above. In one approach, the second motion transfer member includes one or more gears, which may be mechanically interfaced with one or more clutches. In the depicted embodiment, the second motion transfer member includes a second gear 182 mechanically interfaced with a motor gear 174 and a second one-way clutch 184. The second one-way clutch is mechanically interfaced with the output shaft 190 via a series of at least one additional transmission gears 186. In one embodiment, the second motion transfer member also includes a third one-way clutch 188, as described in further detail below.

The bi-directional drive member may be any mechanical or electrical device capable of imparting motion to the first motion transfer member and second motion transfer member. In the depicted embodiment, the bi-directional drive member includes a bi-directional motor 172 and a motor gear 174. The bi-directional motor 172 is mechanically interfaced with the motor gear 174 and is capable of moving the motor gear 174 in a first direction to impart a first output to of the first motion transfer member and second motion transfer member. The bi-directional motor 172 is also capable of moving the motor gear 174 in a second direction to impart a second output to the first motion transfer member and second motion transfer member. In one approach, the bi-directional drive motor 172 is a DC iron-less core motor, with or without an integral gear train, adapted to provide a wide range of output speeds to the motor gear 174 in both the first and second directions. In one embodiment, as described in greater detail below, the bi-directional drive motor 172 is in communication with a processing system to control the speed of rotation of motor gear 174, and correspondingly, the pump drive member and pump.

The pump drive member may be any device capable of receiving motion from either of the first motion transfer member or the second motion transfer member and transferring at least a portion of such motion to a pump. Referring back to FIG. 4, the pump drive member may comprise an output shaft 190, an output worm gear 192, and a mating pump worm gear 194. In one approach, the output shaft 190 is mechanically interfaced with the first and second motion transfer members and receives the output from such first and second transfer members. The output shaft 190 may be mechanically interfaced with the output worm gear 192, which is mechanically interfaced with the mating pump worm gear 194. As the output shaft moves (rotates) in the one direction, the output worm gear 192 may impart motion to the pump via the mating pump worm gear 194 and the pump shaft 196.

Operation of the transmission will be described in reference to FIGS. 11*a* and 11*b*, which uses a system of gears and one-way clutches. However, it will be understood that, as noted above, the first motion transfer member and second motion transfer member could comprise the use of any one of the listed motion transfer mechanisms.

Referring now to FIG. 11*a*, in operation, as motor gear 174 is moved (e.g., rotated) in a first direction by the bi-directional motor 172 (e.g., counterclockwise as depicted by the arrow), the motor gear 174 creates a first output, in the form of mechanical motion, and transfers the first output to the first gear 178 and second gear 182. Both first gear 178 and second gear 182 are consequently moved (e.g., rotated about their axis) in response to the first output (e.g., both gears are rotated in the clockwise direction). In this direction of movement (e.g., rotation), first gear 178 and first one-way clutch 180 are mechanically interfaced such that first gear 178 engages first one-way clutch 180 when receiving the first output, and first one-way clutch 180 imparts the first output to the output shaft 190 and moves (e.g., rotates) it in one direction (e.g., clockwise) at a first speed. However, second gear 182 and second one-way clutch 184 are mechanically interfaced such that second gear 182 does not engage second one-way clutch 184 when receiving the first output. Therefore, the first output received by the second gear 182 is not imparted to the output shaft 190 via the second one-way clutch 184 and the at least one additional transmission gear 186.

Figure 11B:
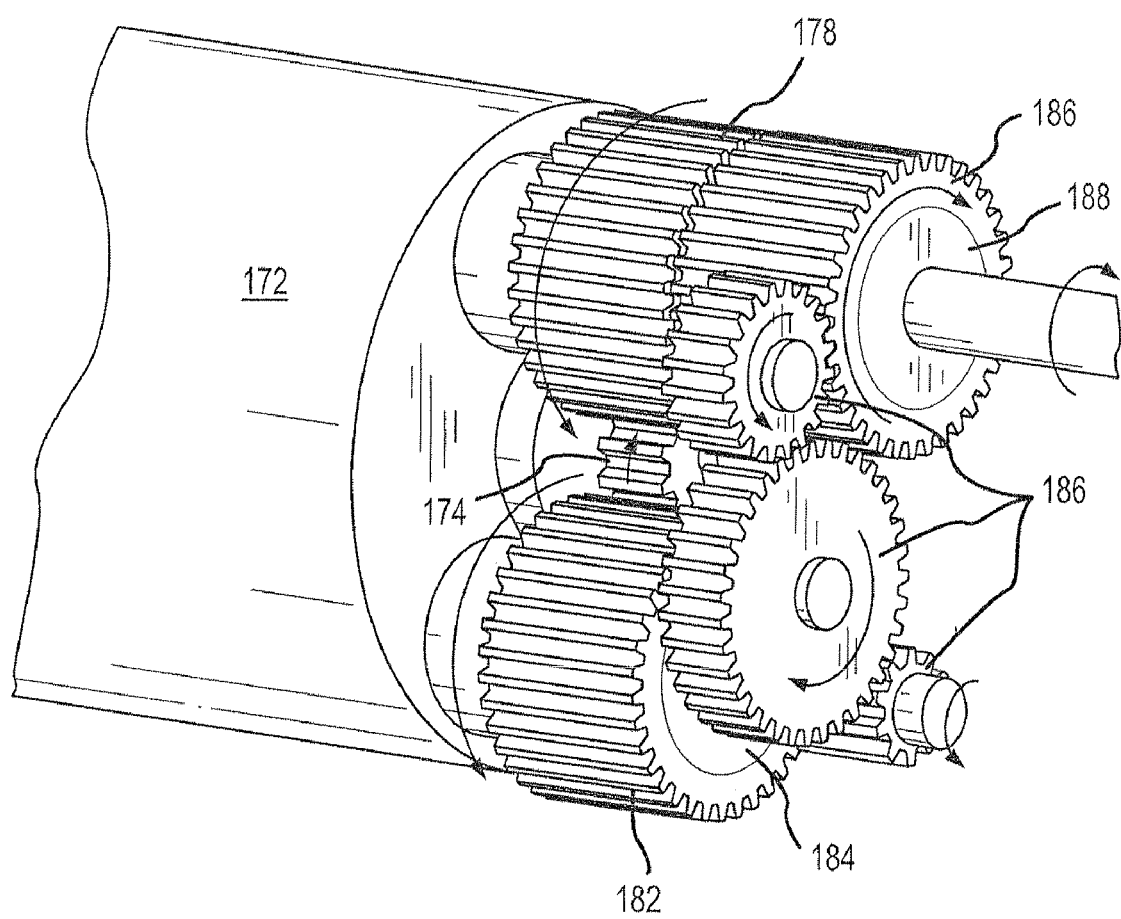
FIG. 11b is a perspective view of one embodiment of a transmission of the present invention.

Referring now to FIG. 11*b*, conversely, when motor gear 174 is moved (e.g., rotated) in a second direction (e.g., clockwise as depicted by the arrow) by the bi-directional motor 172, the motor gear 174 creates a second output of, in the form of mechanical motion, and transfers the second output to the first gear 178 and second gear 182. Both first gear 178 and second gear are consequently rotated about their axis in response to the second output (e.g., both gears are rotated in the counterclockwise direction). In this direction of rotation, first gear 178 and first one-way clutch 180 are mechanically interfaced such that the first gear 178 does not engage first one-way clutch 180 when receiving the second output. However, second gear 182 and second one-way clutch 184 are mechanically interfaced such that second gear 182 does engage second one-way clutch 184 when receiving the second output. The second one-way clutch 184, therefore, engages the at least one additional transmission gear 186, for example via a pinion shaft, and imparts motion to (e.g., drives) the output shaft 190. The output shaft and the at least one additional transmission gear 186 are arranged with the second one-way clutch 184 and second gear 182 such that the output shaft 190 is rotated in the same one direction (e.g., clockwise) as was created with the first output from the bi-directional drive member, but at a second speed.

As noted above, the first motion transfer member and second motion transfer member may comprise a system of gears and one-way clutches. Referring now back to FIG. 4, in one embodiment, due to the arrangement of the at least one additional transmission gear in the second motion transfer member, as the output shaft 190 rotates in the one direction, the at least one additional transmission gear 186 also rotates, irrespective of whether the bi-directional drive member is moving in a first direction or second direction. In some embodiments, such an arrangement may require additional considerations. As will be appreciated, the gears of the first motion transfer member and second motion transfer member should be sized and arranged to avoid a binding situation, such as would occur if the first output resulted in the output shaft moving the at least one additional transmission gear 186 and corresponding second one-way clutch 184 (e.g., via a pinion shaft) in one direction faster than the rotation of slip of the second one-way clutch 184. Additionally, extra power may be required to overcome the mechanical energy utilized to rotate the at least one additional transmission gear 186 during the first output.

Referring back to FIGS. 11*a* and 11*b*, in another aspect of the transmission of the pumping system, the second motion transfer member may comprise a third one-way clutch 188 mechanically interfaced with the output shaft 190 and one of the at least one additional transmission gear 186. The third one-way clutch 188 may be integrated in the transmission such that when the output shaft 190 moves at a certain speed, the third one-way clutch 185 will slip, where no substantial motion is imparted to the at least one additional transmission gear 186 in response to the first output. As will be appreciated, benefits from utilizing the third one-way clutch 188 include reduced power requirements and reduced noise as the at least one additional transmission gear 186 will not be moved. Also, the transmission may have an increased lifetime and a reduced probability of failure as the amount of movement of the gears within the system will be reduced.

As noted above, both the first output and second output result in movement of the pump drive member in the one direction. The speed of movement (e.g., rotation) of the pump drive member (e.g., output shaft 190) in the one direction in response to the first output (i.e., the first speed) may be the same or different than the speed of movement (e.g., rotation) of the pump drive member in the one direction in response to the second output (i.e., the second speed). In one approach, the second speed of the pump drive member (e.g. output shaft 190) is less than the first speed. In another approach, the second speed of the pump drive member (e.g. output shaft 190) is greater than the first speed.

Thus, the pump of the medical fluid delivery system of the present invention may be driven in a single direction by a bi-directional drive member (e.g., a bi-directional motor 172) at various speeds, irrespective of whether the bi-directional drive member is moving in a first or second direction. The benefits of such a system will be appreciated by those skilled in the art. For example, the components of the pumping system (e.g., the bi-directional drive member, transmission and drive pump drive members) may be chosen, arranged and interfaced with the pump to enable the pump to deliver medical fluids to a patient over a wide range of flow rates. For example, the gear ratios of each of the first and second motion transfer members may be chosen to drive the pump drive member over a wide range of speeds such that the pumping system is adapted to provide medical fluid flow to a patient over a wide range of flow rates. In one embodiment, the pumping system is adapted to provide medical fluid flow to a patient in the range of 0.1 ml per hour to 2000 per hour. More particularly, the pumping system may be adapted to provide medical fluid flow to a patient in the range of 0.1 ml per hour 1000 ml per hour.

In one approach, the bi-directional drive member may be moved at a wide range of speeds (e.g., by changing the supplied current and/or voltage to electric bi-directional drive motor) and/or operated at intermittent times in both the first and second directions, thereby enabling the first and second outputs to vary in response thereto. Such speed variation and/or intermittent pump operation, thus, enables a pump interfaced with such bi-directional drive member to deliver medical fluids over a wide range of flow rates in corresponding relation to the first and second outputs. In one approach, the first and second motion transfer members are chosen and arranged with the bi-directional drive member and pump drive member such that at least one, and in some instances each, is capable of changing the fluid delivery rate of the pump by a factor of up to 1000× (e.g., 2×, 3×, 4×, 5×, 10×, 25×, 50×, 75×, 100×, 250×, 500×, 750× and 1000×) in corresponding relation to speed changes and/or changes in time of operation (e.g., more or less intermittent or continuous) of the bi-directional drive member.

In another approach, the first and second motion transfer members are chosen and arranged with the bi-directional drive member and pump drive member such that the first output corresponds to a maximum medical fluid delivery rate that is up to 1000 times greater (e.g., 2×, 5×, 10×, 20×, 50×, 100×, 250×, 500× and 1000×) than the maximum medical fluid delivery rate that corresponds to the second output. In one aspect, the first output corresponds to a medical fluid delivery rate of between 10 ml per hour and 1000 ml per hour, and the second output corresponds to a medical fluid delivery rate of between 0.1 ml per hour and 10 ml per hour. In another aspect, the first output corresponds to medical fluid delivery of between 100 ml per hour and 2,000 ml per hour, and the second output corresponds to medical fluid delivery rate of between 1 ml per hour and 100 ml per hour. As will be appreciated, the first output and second output could be rearranged such that the first output corresponds to the lower fluid delivery rate and the second output corresponds to the higher fluid delivery rate.

Figure 12:
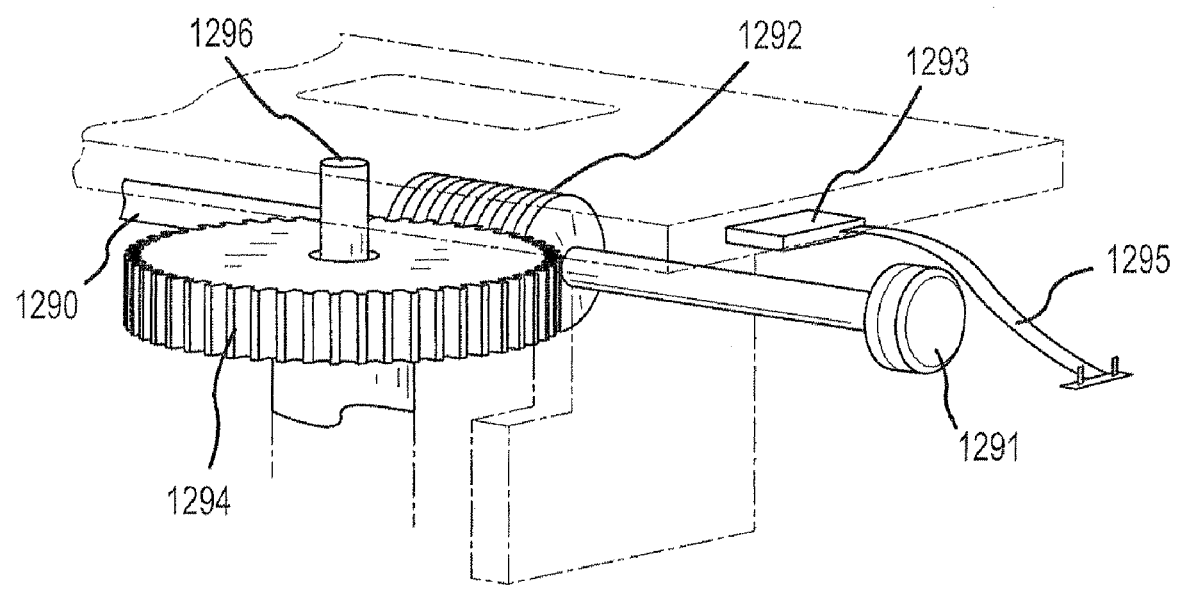
FIG. 12 is a perspective view of one embodiment of a pump speed determination system of the present invention.

The pumping system of the present invention may also include a pump speed determination system to enable a determination of the speed of the pump. In one embodiment, the pump speed determination system comprises the use of an encoder, as described above, and as will now be described in reference to FIG. 12. The pump and the pump speed determination system may include a pump drive member (e.g., an output shaft 1290, output worm gear 1292, mating worm gear 1294) mechanically interfaced with the 1200 pump (not shown) via a pump drive shaft 1296. The pump drive member may also include components for calculating the speed of rotation of the pump head. The pump speed determination system may further include at least one encoder and an electrical output line to 1295. The at least encoder 1291 is generally in communication the electrical output line 1295.

In one approach, the at least one magnet is used as the encoder 1291 and includes four magnets equally positioned about the output shaft 1290. A reed switch 1293, which may contain two switches approximately 45° rotationally apart, maybe in magnetic vacation with the magnetic encoder 1291.

The pumping system 170 of the medical fluid delivery system of the present invention may be any device adapted for the moving medical fluid to the patient. For example, the pumping system 170 may operate through changes in pressure and/or gravity, such by using a rotary peristaltic pump, linear peristaltic pump centrifugal pump, diaphragm pump or piston pump.

Figure 13:
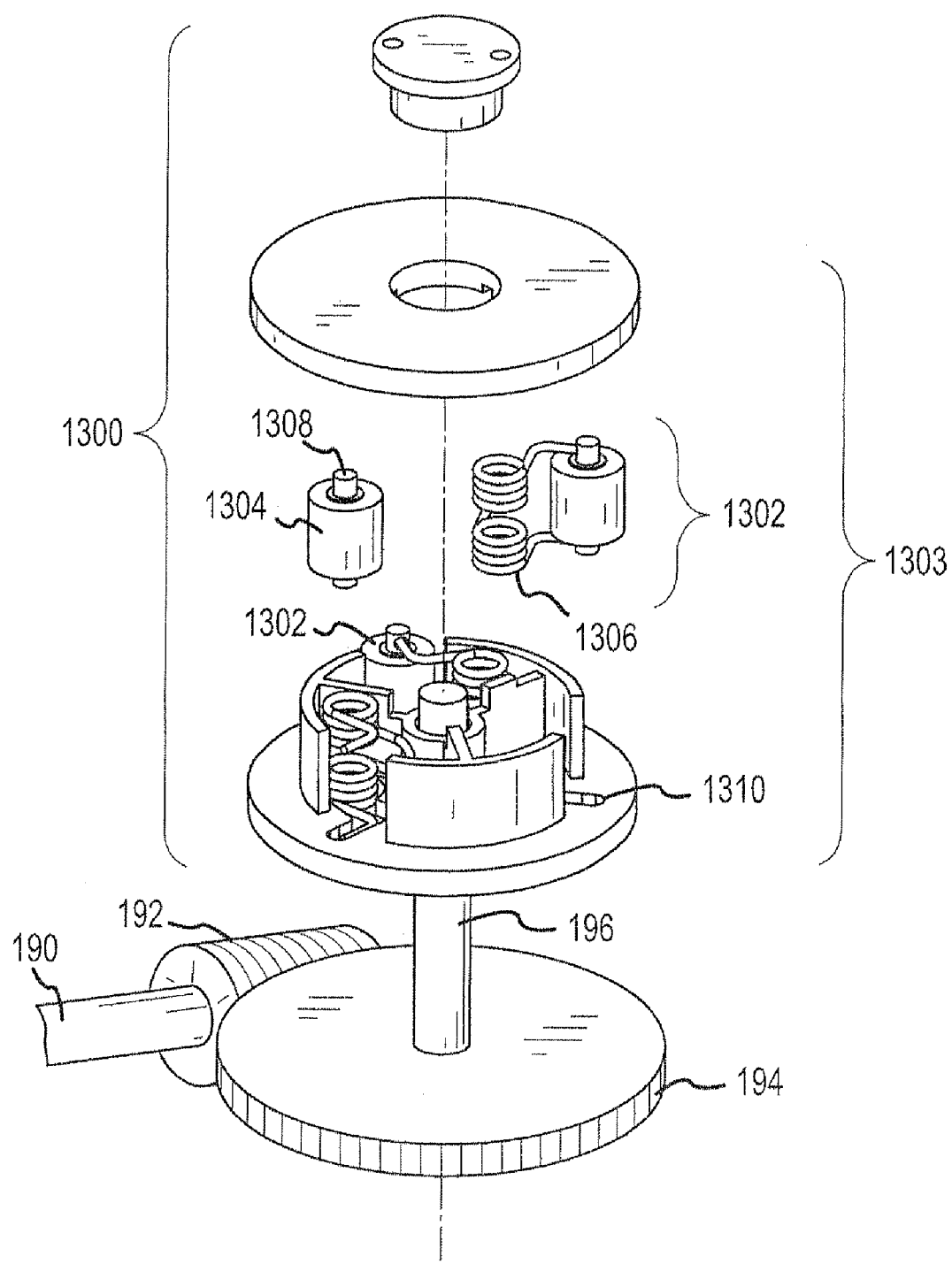
FIG. 13 is an exploded view of one embodiment of a pump of the present invention.
Figure 14A:
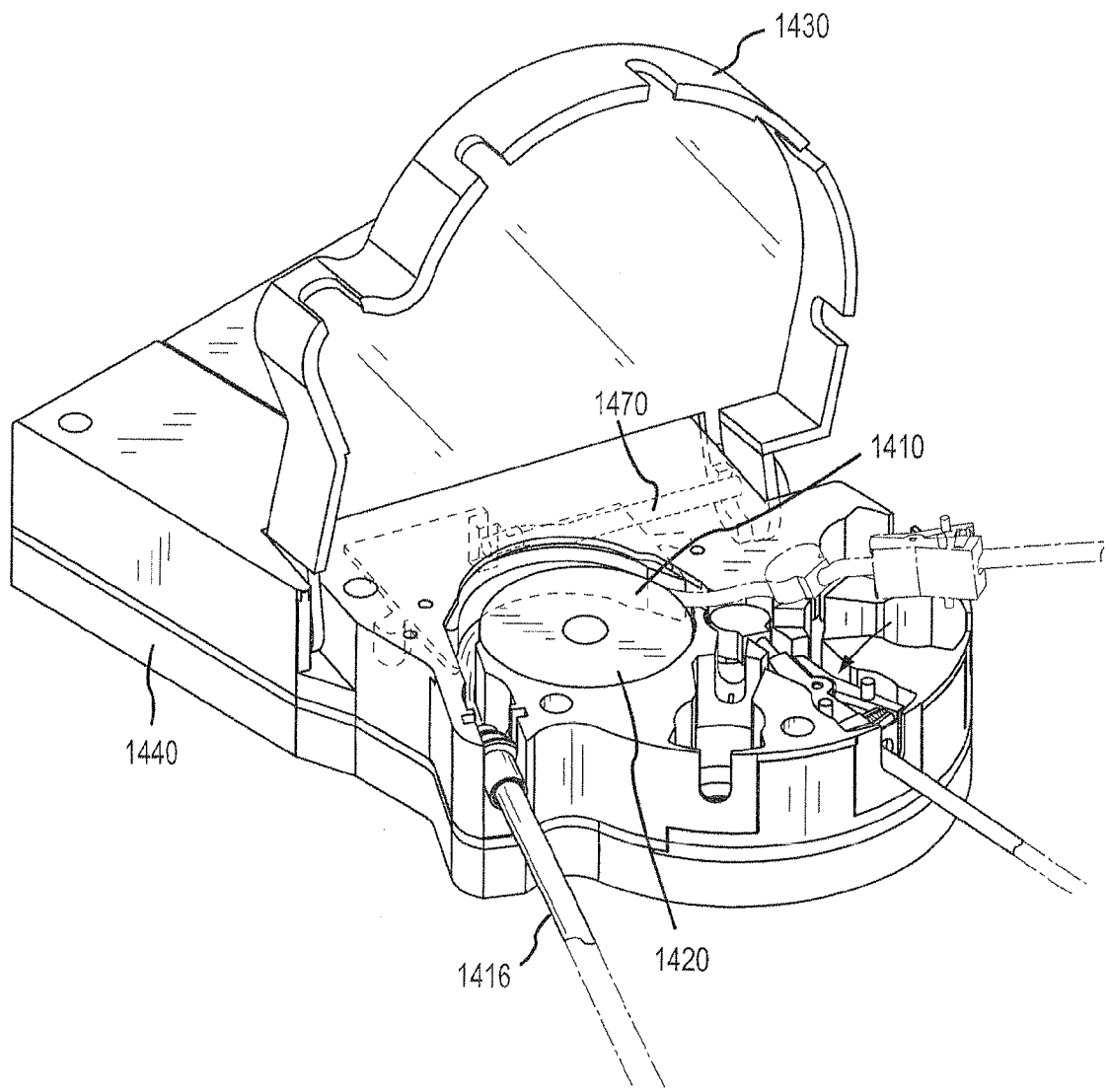
FIG. 14a is a perspective view of one embodiment of the medical fluid delivery system of the present invention.
Figure 14B:
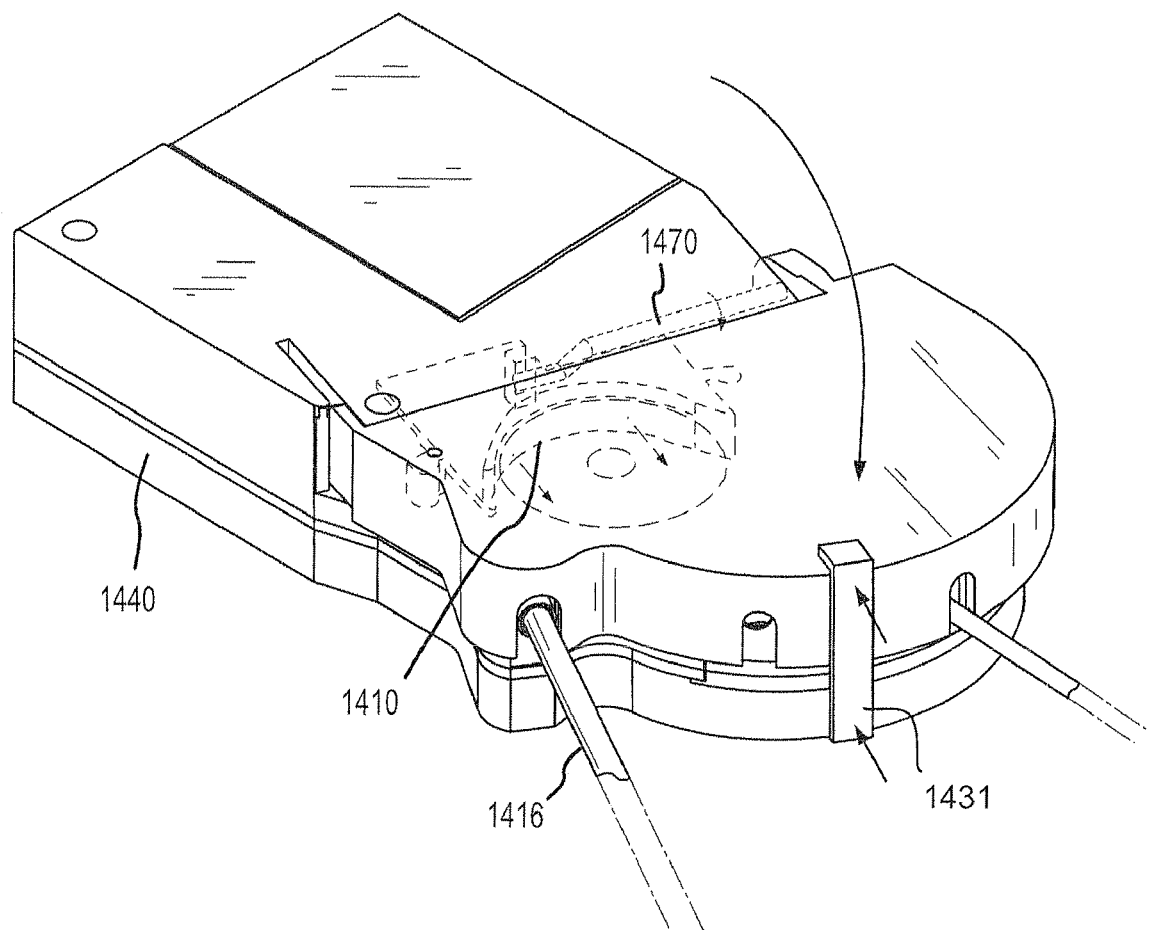
FIG. 14b is a perspective view of one embodiment of the medical fluid delivery system of the present invention.
Figure 14C:
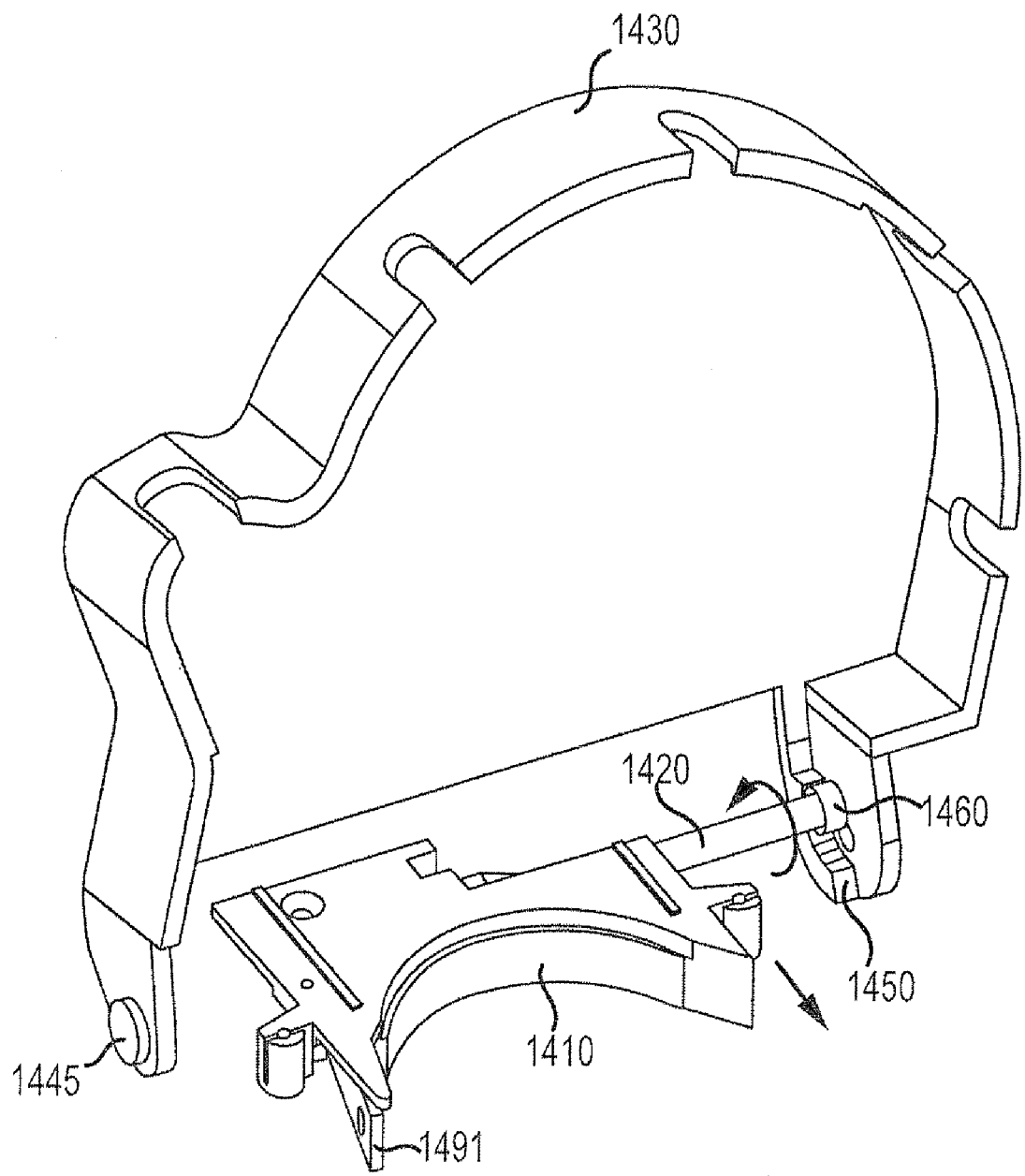
FIG. 14c is a perspective view of one embodiment of a cover and pump anvil of the present invention.
Figure 14D:
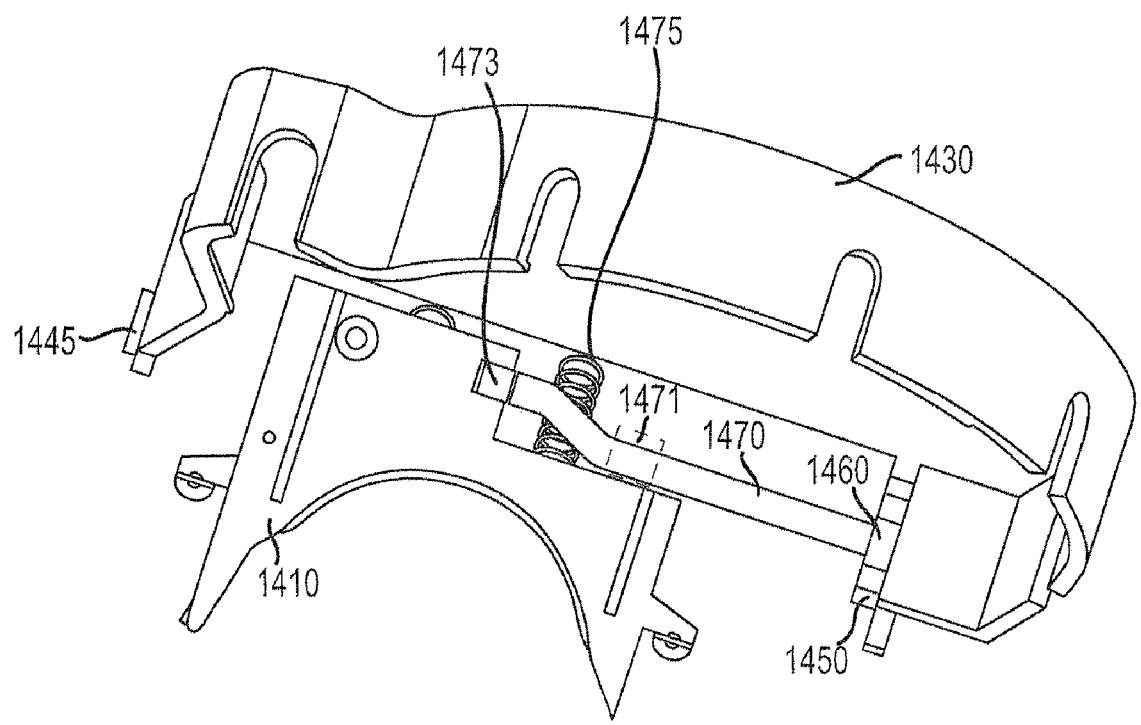
FIG. 14d is a top-view of one embodiment of a cover and pump anvil of the present invention.

In one embodiment, the pumping system 170 comprises a rotary peristaltic pump, as is now further described in relation to FIG. 13. A rotary peristaltic pump 1300 generally comprises a pump head 1303, which comprises pinch members 1302, which comprise a pinch-roller 1304, a pinch-spring 1306 and a pinch-roller shaft 1308. The pinch members 1302 may be equally spaced around the pump head 1303 and may rotate about the pinch roller shafts 1308 on a sleeve bearing to pinch a medical fluid line against an anvil surface (not shown). The pinch members 1304 may be designed to substantially or completely occlude the medical fluid line against the anvil, and, therefore, the pinch members 1304 may have the ability to account for system tolerances of different medical fluid line sets. In one aspect, the pinch-rollers 1304 may be biased away from the center of head rotation by a pinch-spring 1306 (e.g., a coil torsion spring), which may retain the pinch-roller 1304 on the pinch-roller shaft 1308. The pinch-springs 1306 provide a motive force for pushing the pinch-rollers 1304 toward the outer perimeter (e.g., circumference) of the pump head 1303, which acts to pinch the pinch-rollers 1304 against the medical fluid line and the anvil surface. The pinch members 1302 may also be allowed to slide an amount slightly more than the system tolerances utilizing the holes 1310. Thus, the pinch members may be able to move toward and away from the anvil and the medical fluid line contained in the pump head, which receive the pinch-roller shafts 1308. In operation, as the pump head 1303 rotates, the pinch members 1302 pinch the medical fluid line against the anvil, and any medical fluid within the medical fluid line will be forced, (e.g., via motive and pressure head forces) through the line in the direction of movement of the pump head, as is well known in the art.

In one embodiment, rotation of the pinch members in a first direction moves medical fluid from one or more of the medical fluid delivery lines to a medical fluid output line, such as to a patient, as described above. In an alternate embodiment, rotation of the pinch members in a second direction moves medical fluid from a medical fluid output line to at least one medical fluid delivery line. Rotation of the pinch members in this second direction would enable distribution of a medical fluid into multiple receptacles, for example.

Placement of the medical fluid line within the pump head may be accomplished via any known means, such as removal of a portion the top of the pump head, followed by subsequent replacement of the portion of the pump head. In one aspect of the present invention, the medical fluid delivery line system comprises a cover interfaced with the pump to enable movement of at least a portion of the pump so that a medical fluid line may be placed or removed without removing of any of the parts of the pump.

Referring now to FIGS. 14*a*-14*d*, one embodiment of a medical fluid delivery system including a moveable portion for placement and removal of a medical fluid line is depicted. In this embodiment, the anvil 1410 of a pump is movable to allow initial placement of the medical fluid line 1416 in the channel of the pump head 1420. In one aspect, the anvil 1410 may be mechanically coupled to the motion of an angular element, in this embodiment, a cover 1430, such that as the cover 1430 rotates about two hinge points (e.g., approximately 100 degrees), the anvil 1410 is drawn away from the pinch members, thereby allowing placement of a medical fluid line 1418. When the cover 1430 is closed, the anvil 1410 moves back towards the pinch members and the medical fluid line may be pinched therebetween, as described above. A latch 1431 may be used to maintain the cover in a closed position.

In a particular embodiment, the coupling of the motion of the cover 1430 is pivotally connected to the medical fluid delivery system housing 1440 by one or more hinges. The cover 1430 may contain a partial internal gear ring 1450 adjacent to the hinge point(s) 1445, which is arranged to mechanically interfaced with a anvil gear 1460 on the anvil shaft 1470. The anvil gear 1460 of the anvil shaft 1470 is chosen to have a pitch diameter smaller than the internal ring gear 1450 of the cover 1430. The ratio of the internal gear ling 1450 to the anvil gear 1460 should be arranged and interfaced such that movement of the internal gear ring 1450, via the cover 1430, moves the anvil 1410 an amount necessary to enable placement of the medical fluid line within the pump. For example, the internal gear ring 1450 and anvil gear 1460 may be arranged and interfaced such that 100 degrees of rotation of the cover 1430 rotates that anvil shaft 1470 approximately 200 degrees.

In one aspect, the anvil shaft 1470 may be constrained in the direction of rotation by a rotational sleeve bearing 1471. Further, the anvil may also be mechanically engaged to an offset portion of the anvil shaft 1470 by an engaging sleeve bearing 1473. The engaging sleeve bearing 1473 may be arranged to contact the anvil 1410 such that the angular (e.g., rotary) motion of the anvil shaft 1470 results in a linear motion for the anvil 1410. In another approach, the anvil shaft 1470 may also be arranged to rotate approximately 20 degrees past maximum displacement to provide a method of self-holding the anvil 1410 and pump cover 1430 in the open position.

In one embodiment, a biasing means 1475 (e.g., a spring) may be used to bias the anvil 1410 in a desired direction to maintain its position within the pump head 1420. Thus, the biasing means 1475 may help ensure that the medical fluid line 1416 is properly arranged within the pump head 1420 (e.g., in physical communication with the anvil and pump rollers, described above) so that the pump deliver medical fluids, as described above.

In a particular embodiment, a cantilever force beam 1491 is mechanically attached to the anvil 1410 such that as the anvil 1410 slides towards the pump head 1420, the end of the cantilever force beam 1491 contacts the medical fluid line 1416 at a point downstream from the pump head 1420. This contact may compress the medical fluid line 1416 at the point of contact. Pressure inside the medical fluid line causes the cantilever force beam to move in a substantially linear fashion. The movement of the cantilever force beam in response to the pressure profile within the medical fluid line may be coupled to a sensor and/or processor to statically or dynamically collect pressure information about the medical fluid line 1416. For example, the processor may utilize the pressure information to determine whether the pump is operating correctly (e.g., whether a fluid reservoir is empty or whether a line is blocked). In one aspect, the processor may determine whether the pump is operating correctly by comparing the measured pressure profile of the medical fluid delivery line to a known pressure profile.

In another aspect, the pressure inside the medical fluid line may be measured using a force sensor (e.g., a piezoelectric sensor) located downstream of the pump in physical communication with the medical fluid output line 1416, such as those supplied by Honeywell International, Inc. (Morristown, N.J., U.S.A.), (e.g., a Model 1865 Force Sensor). As is known by those in the art, the force sensor may be communicatively coupled to a processor to collect pressure information about the medical fluid output line 1416.

The medical fluid delivery system of the present invention may include any one of the above described components and in any combination. In one approach, the medical fluid delivery system may simply comprise a single medical fluid line interfaced with a pump. In one aspect of this approach, the medical fluid line may be received by a valve of the present invention. In an additional aspect of this approach, the medical fluid line maybe interfaced with a valve operating system of the present invention via the valve. In yet another embodiment of this approach, the pump may comprise a pumping system of the present invention.

In another embodiment, the medical fluid delivery system may comprise a disposable medical fluid line set interfaced with a pump, where the disposable medical fluid line set comprises a plurality of medical fluid delivery lines. In one aspect of this embodiment, at least one of the plurality of medical fluid delivery lines may be received by at least one valve of the present invention. In another aspect of this embodiment, the disposable medical fluid line set may be interfaced with a valve operating system of the present invention. In yet an additional approach to this embodiment, a pumping system of the present invention may be interfaced with the disposable medical fluid line set.

Figure 15:
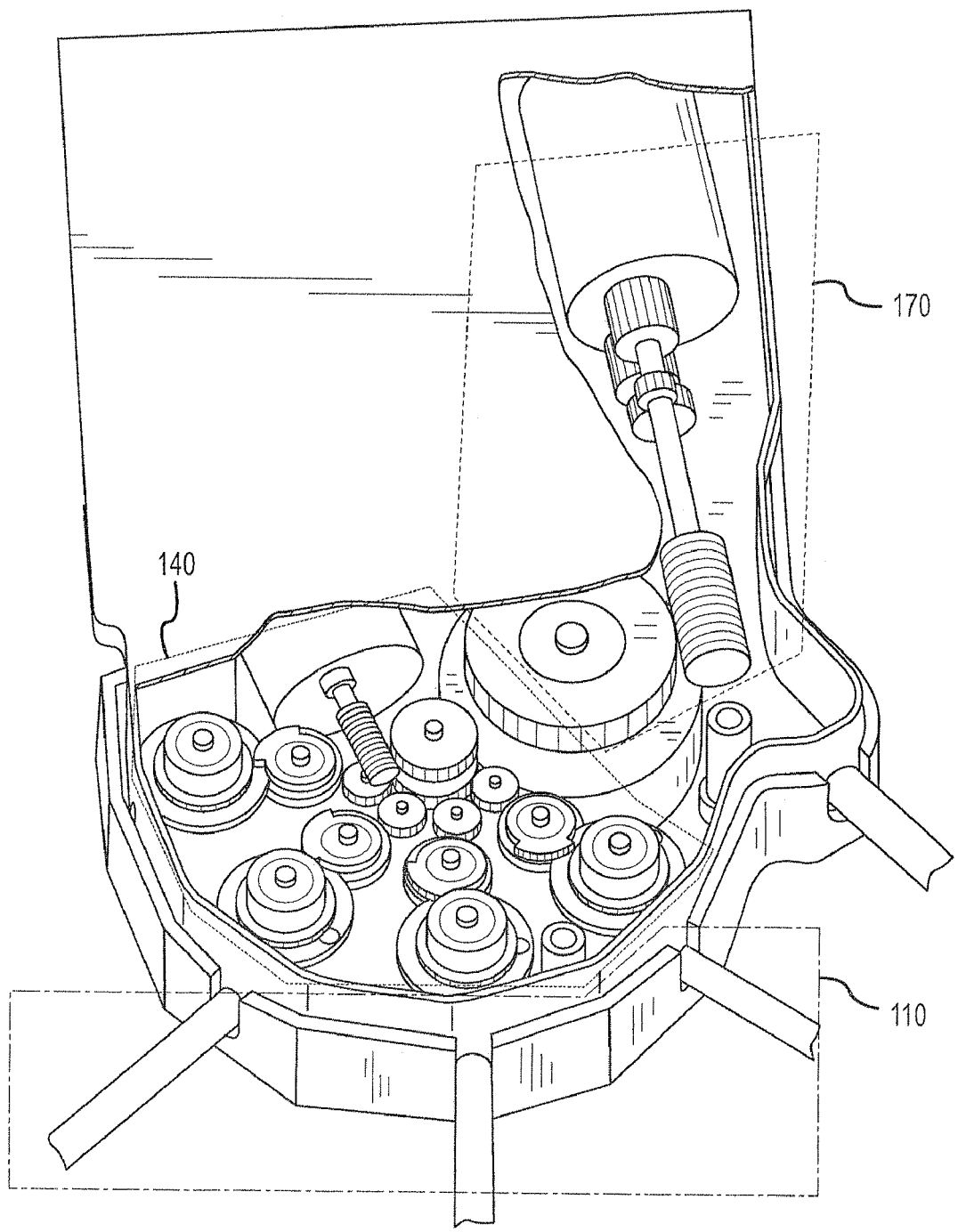
FIG. 15 is a perspective view of one embodiment of the medical fluid delivery system of the present invention.
Figure 16:
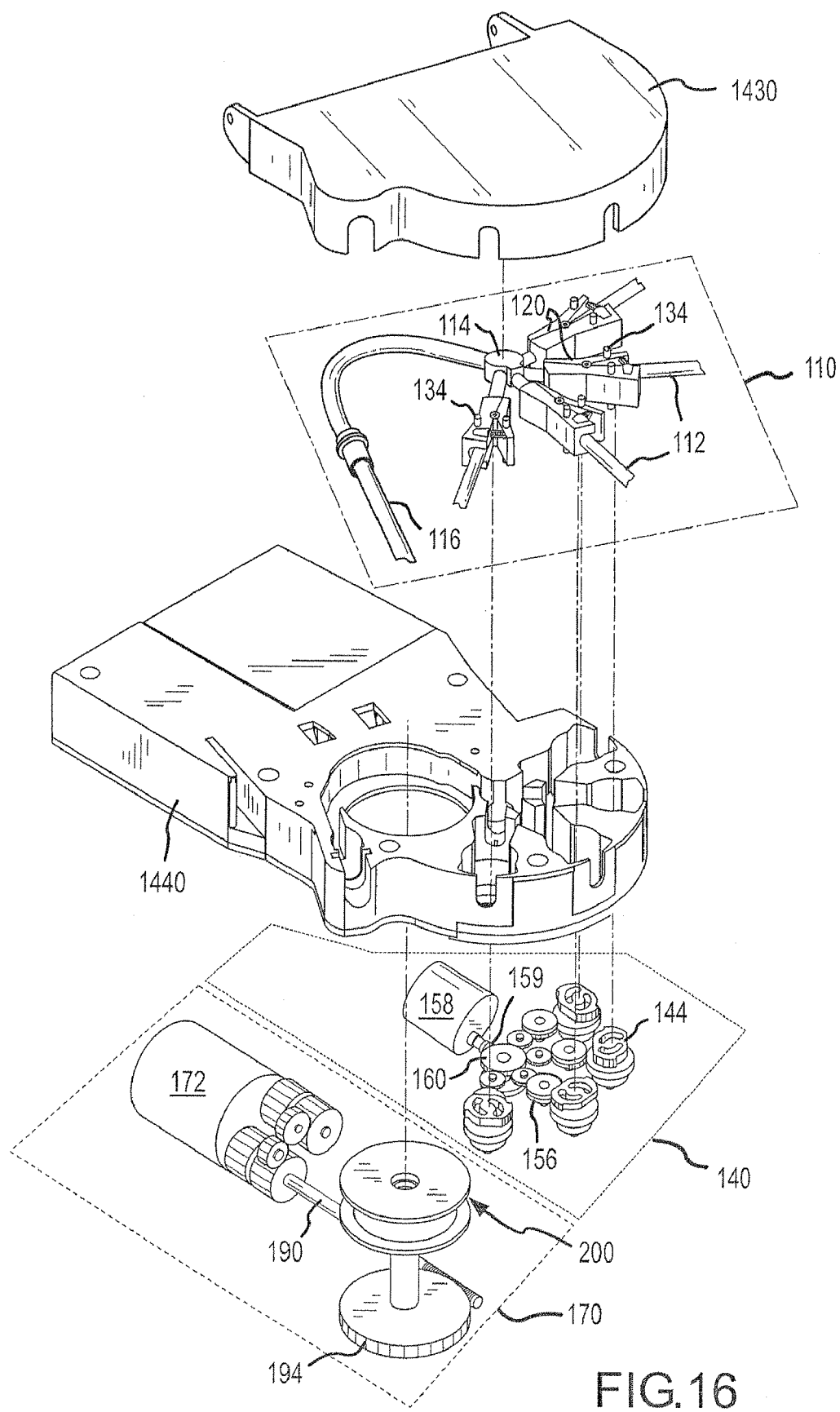
FIG. 16 is an exploded view of one embodiment of the medical fluid delivery system of the present invention.

In one embodiment, the medical fluid delivery system comprises all of a disposable medical fluid line set, at least one valve, a valve operating system and a pumping system, as depicted in FIGS. 15 and 16. In such an embodiment, the medical fluid delivery system comprises a disposable medical fluid line set 110 interfaced with a valve operating system 140 and a pumping system of the present invention, each contained within a single housing 1440. However, any of the components of the medical fluid delivery system may be interfaced with one another without using a housing or using a plurality of housings.

One embodiment of the speed range in relation to the motor armature is described below and in reference to FIGS. 17a and 17b. Various embodiments of a pump speed determination system are also described below in relation to FIGS. 18a and 18b. In reference to FIGS. 17a, 17b, 18a and 18b, the terms "clockwise" and "counterclockwise" are used for illustration purposes, but such terms are used only for the purposes of illustration, and are not meant to be limiting in any fashion.

Figure 17A:
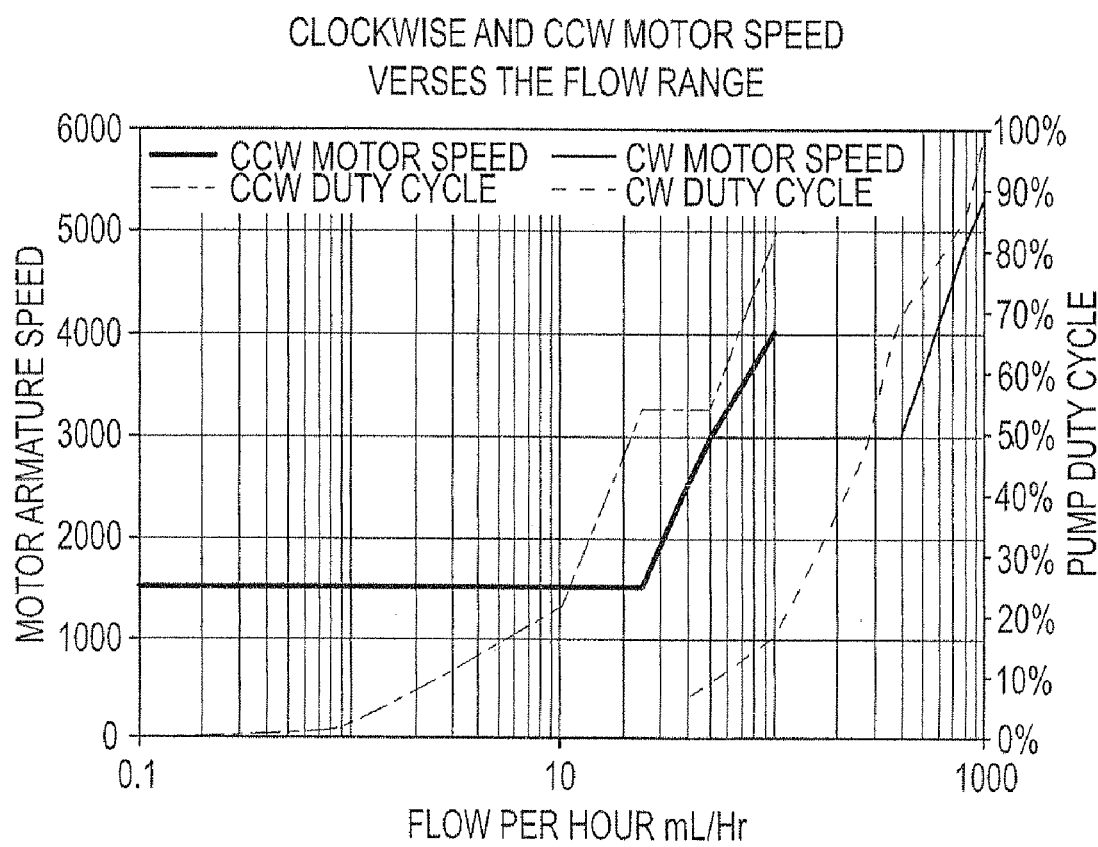
FIG. 17a is a chart relating fluid flow rate to motor armature speed and pump duty cycle in one embodiment of the present invention.
Figure 17B:
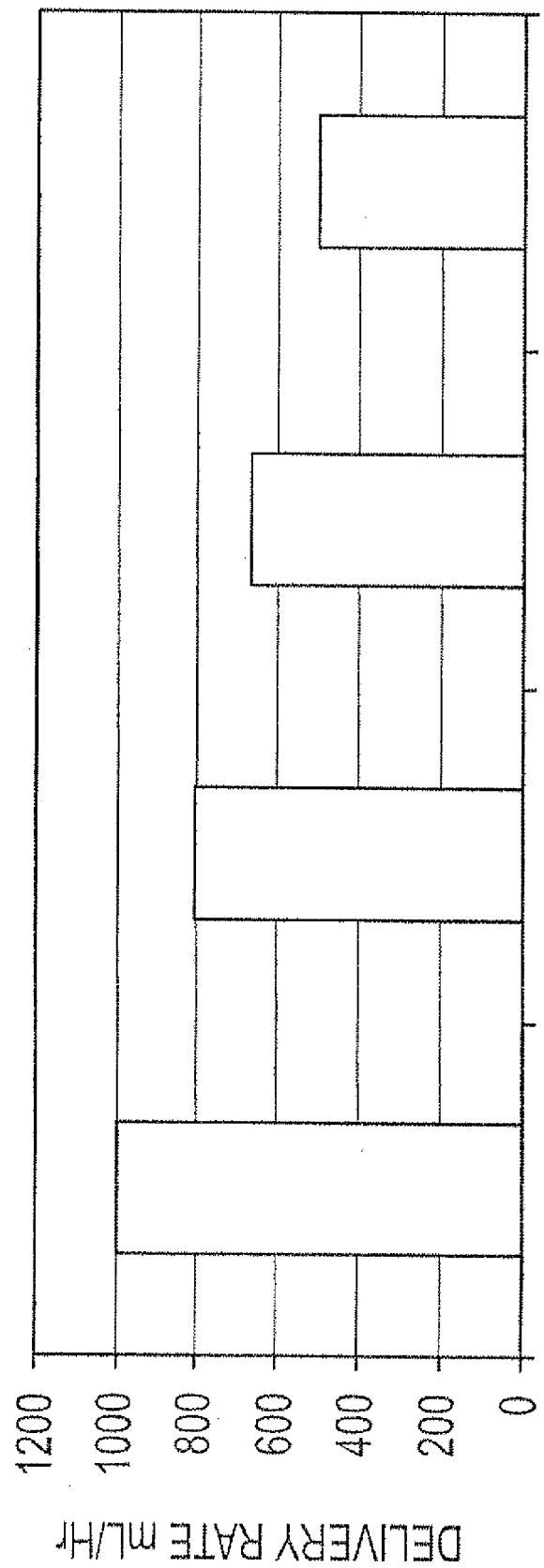
FIG. 17b is a chart relating fluid flow delivery rate to the number of lines being utilized according to one embodiment of the present invention.

FIG. 17a depicts the motor speed versus desired flow for movement of a motor in a first direction (e.g., clockwise) and movement of the motor in a second (e.g., counterclockwise) direction. The first solid line (as moving across the page left to right) shows the counterclockwise motor speed is held constant at 1500 rpm for flow ranges from 0.1 to 25 ml/hr. The first dashed line is the counterclockwise motor duty cycle associated with that flow rate. In this embodiment, the duty cycle is less than 10% for flow rates less than 2 ml/hr. In one aspect, the counterclockwise motor speed may be constant at about 1500 rpm relating to a fluid delivery rate of 0.1 to 25 ml/hr, and the duty cycle may be increased to achieve the desired flow. To deliver 25 ml/hr to 100 ml/hr, the rpm and/or duty cycle may be increased to achieve the selected flow. At approximately 50 m/hr or higher, the flow may be achieved from clockwise rotation of the motor. In one aspect, the clockwise motor speed may be maintained at about 3000 rpm to deliver from 50 to 400 ml/hr, again with a variable duty cycle. To achieve from about 400 ml/hr to 1000 ml/hr, the motor speed and/or duty cycle may be increased. In one aspect, the maximum motor speed may be about 5500 rpm, which may include a duty cycle of 99%.

The time to change between the fluid lines may consume pumping time and reduce the available duty cycle and/or fluid delivery rate. FIG. 17b depicts one embodiment of a 4 fluid line system. As shown, two lines may be limited to a fluid delivery rate of 800 mL/hr, three lines may be limited to a fluid delivery rate of 650 ml/hr, and four lines may be limited to a fluid delivery rate of 500 mL/hr.

In one embodiment of the pump speed determination system, a Hall effect sensor is used to monitor the rotation of the 50-tooth worm gear attached to the pump head shaft. This gives a (360/50) 7.2 degree per pulse resolution. For example, at a 1000 ml/hr flow rate, the sensor output frequency is 47 Hz or 2820 cycles per min, which will require an electrical sensing of 2820 cycles per min +/−28 cycles to achieve a +/−1% control accuracy. At a clockwise speed of 3000 rpm, the frequency output may be reduced to 26 Hz and +/−15 cycles per min to achieve a 1% control accuracy.

Figure 18A:
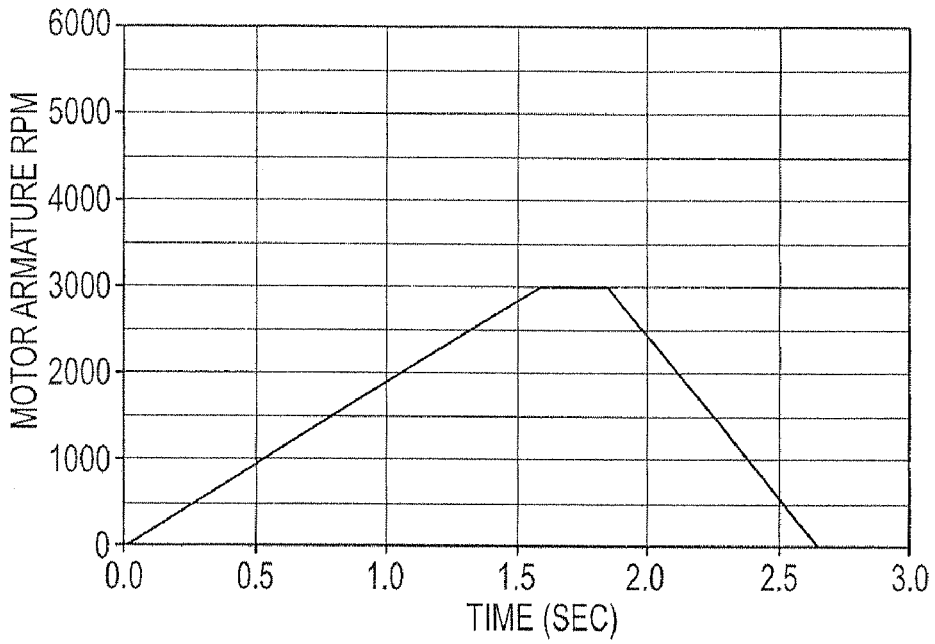
FIG. 18a is a chart of a minimum first direction motor speed profile according to one embodiment of the present invention

FIG. 18a is a chart depicting one embodiment of a minimum motor speed verses time in the clockwise direction. In one embodiment, at a minimum clockwise speed, one motor pulse would be greater than the 15 cycles/min for accuracy purposes. Therefore, in one embodiment, a processor and associated circuitry may intermittently drive the pump motor in the counterclockwise direction to achieve a correct number of sensor pulses. For example, if at the end of a clockwise delivery pulse in a 30-second time frame, the pulse count may be less than the desired count, and the motor may need to be driven in a counterclockwise direction to achieve the correct pulse count. Conversely, if the pulse count is larger than the target count, the next clockwise run may be purposefully reduced, and the correct count may be achieved by counter-clockwise rotation within a 30-second time frame.

Figure 18B:
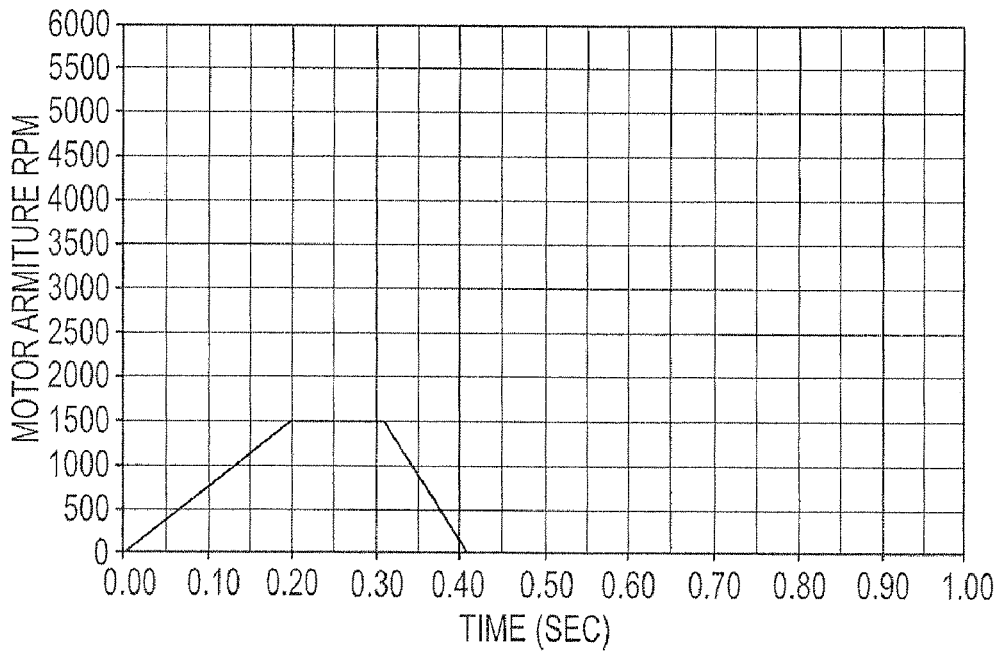
FIG. 18b is a chart of a minimum second direction motor speed profile according to one embodiment of the present invention

FIG. 18b shows a simplified embodiment of one expected minimum counterclockwise motor speed verses time. In this embodiment, a minimum motor pulse corresponds to 3.9 degrees of pump head rotation. At a minimum flow rate of 0.1 mL/hr the motor would pulse 30 times at 3.9° per pulse to rotate the pump head 117° per hour.

At the maximum flow rate of 1000 mL/hr the motor would rotate the pump head 3250 revolutions per hour or 27 revolutions per 30 second pump cycle. At the clockwise gear ratio the motor may be rotating at 5300 rpm.

All of the concepts, devices and methods disclosed and claimed herein can be made and executed without undue experimentation in light of the present disclosure. While the concepts, devices and methods of this invention have been described in terms of particular and preferred embodiments, it will be apparent to those of skill in the art that variations may be applied to the concepts, devices and methods and in the steps or in the sequence of steps of the methods described herein without departing from the concept, spirit and scope of the invention. More specifically, it will be apparent that certain components may be substituted for the components described herein and the same or similar results would be achieved. All such similar substitutes and modifications apparent to those skilled in the art are deemed to be within the spirit, scope and concept of the invention as defined by the appended claims.

What is claimed is:

1. A method of operating at least one medical fluid delivery line valve, the method comprising:
   mechanically interfacing a valve controller with a first medical fluid delivery line valve, wherein the valve controller is operable in a first direction and a second direction, wherein operation of the valve controller causes a first activation member associated with the first medical fluid delivery line valve to move to at least a first position and a second position, and wherein operation of the valve controller in the second direction does not actuate the first medical fluid delivery line valve, and wherein operation of the valve controller in the first direction at least partially actuates the first medical fluid delivery line valve during movement of the first activation member from the first position to the second position;
   operating the valve controller in the second direction to move the first activation member to the first position, wherein the first medical fluid delivery line valve is not actuated during operation of the valve controller in the second direction; and
   operating the valve controller in the first direction to move the first activation member to the second position, whereby the first medical fluid delivery line valve is at least partially actuated,
   wherein the first activation member includes an active interface portion and an inactive interface portion.

2. The method of claim 1, wherein the first direction and the second direction are rotational directions.

3. The method of claim 1, wherein actuation of the first medical fluid delivery line valve causes the first medical fluid delivery line valve to transition from a biased position to a non-biased position.

4. The method of claim 1, wherein actuation of the first medical fluid delivery line valve causes the first medical fluid delivery line valve to transition from a closed position to an at least partially open position.

5. The method of claim 1, further comprising:
   determining that the first medical fluid delivery line valve is actuated; and
   de-actuating the first medical fluid delivery line valve.

6. The method of claim 5, wherein de-actuating the first medical fluid delivery line valve comprises operating the valve controller in the second direction to move the first activation member back to the first position from the second position.

7. The method of claim 1, wherein the active interface portion is adapted to interface with a corresponding actuator gear, and wherein the inactive portion is adapted to not interface with the corresponding actuator gear.

8. The method of claim 1, wherein the active interface portion is contiguous.

9. The method of claim 1, wherein the active interface portion is non-contiguous.

10. The method of claim 1, further comprising:
    interfacing a first medical fluid delivery line with a pump;
    engaging the medical fluid delivery line with the first medical fluid delivery line valve; and
    operating the pump to cause a fluid to flow through the first medical fluid delivery line.

11. The method of claim 10, wherein operating the pump comprises pinching the first medical fluid line against an anvil.

12. The method of claim 10, further comprising mechanically coupling a first portion of the pump with a cover.

13. The method of claim 12, wherein motion of the cover causes the first portion of the pump to move away from a second portion of the pump.

14. The method of claim 13, wherein motion of the first portion away from the second portion of the pump enables placement of the first medical fluid delivery line.

15. The method of claim 11, further comprising mechanically coupling the anvil to an angular element.

16. The method of claim 15, wherein angular motion of the angular element causes linear motion of the anvil.

17. The method of claim 16, wherein linear motion of the anvil enables placement of the first medical fluid delivery line between the anvil and a pump head.

18. A method of operating at least one medical fluid delivery line valve, the method comprising:
mechanically interfacing a valve controller with a first medical fluid delivery line valve, wherein the valve controller is operable in a first direction and a second direction, wherein operation of the valve controller causes a first activation member associated with the first medical fluid delivery line valve to move to at least a first position and a second position, and wherein operation of the valve controller in the second direction does not actuate the first medical fluid delivery line valve, and wherein operation of the valve controller in the first direction at least partially actuates the first medical fluid delivery line valve during movement of the first activation member from the first position to the second position;
operating the valve controller in the second direction to move the first activation member to the first position, wherein the first medical fluid delivery line valve is not actuated during operation of the valve controller in the second direction;
operating the valve controller in the first direction to move the first activation member to the second position, whereby the first medical fluid delivery line valve is at least partially actuated; and
coupling a first actuator clutch with the first medical fluid delivery line valve.

19. The method of claim 18, wherein the first actuator clutch engages in the first direction and slips in the second direction.

20. A valve operating system for use in delivering at least two medical fluids, the valve operating system comprising:
first and second valve interface members comprising first and second valve actuators adapted to operatively interface with first and second medical fluid delivery line valves, respectively; and
a valve controller mechanically interfaced with the first and second valve interface members, wherein the valve controller is operable in a first direction and a second direction, wherein operation of the valve controller in the first direction causes a first motion output and a second motion output, wherein the first motion output at least partially actuates the first valve actuator and wherein the second motion output at least partially actuates the second valve actuator, and wherein operation of the valve controller in the second direction causes a third motion output that does not actuate the first valve actuator or the second valve actuator.

21. The valve operating system of claim 20, wherein the first motion output and the second motion output are at least partially non-overlapping.

22. The valve operating system of claim 20, wherein the first direction and the second direction are rotational directions.

23. The valve operating system of claim 20, wherein the valve controller includes first and second activation members mechanically interfaced with the first and second valve interface members, respectively, and wherein the first motion output causes motion to the first activation member to thereby actuate the first valve actuator and the second motion output causes motion to the second activation member to thereby actuate the second valve actuator.

24. The valve operating system of claim 23, wherein the third motion output causes motion to one or more of the first activation member and the second activation member, without actuating the first valve actuator or the second valve actuator.

25. The valve operating system of claim 23, wherein the first activation member and the second activation member each comprises at least one active interface portion and at least one inactive interface portion.

26. The valve operating system of claim 25, wherein the at least one active interface portion is sized in relation to the number of valves associated with the medical fluid delivery system.

27. The valve operating system of claim 23, wherein the interface between the first activation member and the first interface member and the interface between the second activation member and the second interface member each comprises an active interface portion and an inactive interface portion.

28. The valve operating system of claim 25, wherein the at least one active interface portion is contiguous.

29. The valve operating system of claim 20, wherein the third motion output repositions the valve controller.

30. The valve operating system of claim 20, wherein the third motion output de-actuates the first or second valve actuator if the first or second valve actuator is in a non-biased position.

31. The valve operating system of claim 20, wherein the first valve interface member further comprises a first one-way actuator clutch.

32. The valve operating system of claim 31, wherein the first one-way actuator clutch engages in the first direction and slips in the second direction.

33. The valve operating system of claim 31, wherein the first valve interface member further comprises a first actuator gear, wherein the first actuator gear interfaces with the valve controller and the first one-way actuator clutch.

34. The valve operating system of claim 32, wherein the first one-way actuator clutch engages in response to the first motion output of the valve controller.

35. The valve operating system of claim 32, wherein the first one-way actuator clutch slips in response to the third motion output of the valve controller.

36. The valve operating system of claim 32, wherein engaging the first one-way actuator clutch at least partially actuates the first valve actuator and slipping the first one-way actuator clutch does not actuate the first valve actuator.

37. The valve operating system of claim 20, wherein the first motion output corresponds to movement of the valve controller in the first direction from a first controller orientation to a second controller orientation, wherein the third motion output corresponds to movement of the valve controller in the second direction from the second controller orientation to a third controller orientation, and wherein the second motion output corresponds to movement of the valve controller in the first direction from the third controller orientation to a fourth controller orientation.

38. The valve operating system of claim 25, wherein the degree of angular rotation associated with each of the active interface portions is a function of the number of medical fluid delivery line valves.

39. The valve operating system of claim 37, wherein a degree of angular movement of the third motion output is at least equal to a combination of the degree of angular movement of the first motion output and the degree of angular movement of the second motion output.

40. The valve operating system of claim 37, wherein in the first controller orientation the first valve actuator is in a non-actuated position and the second valve actuator is in a non-actuated position.

41. The valve operating system of claim 37, wherein in the second controller orientation the first valve actuator is in an actuated position and the second valve actuator is in a non-actuated position.

42. The valve operating system of claim 37, wherein in the third controller orientation the first valve actuator is in a non-actuated position and the second valve actuator is in a non-actuated position.

43. The valve operating system of claim 37, wherein in the fourth controller orientation the first valve actuator is in a non-actuated position and the second valve actuator is in an actuated position.

44. The valve operating system of claim 20, wherein the first valve actuator is adapted to automatically return to a starting position when not engaged by the valve controller.

45. The valve operating system of claim 20, wherein the first medical fluid delivery line valve is fixed in an open or closed position with at least one temporary biasing structure.

46. The valve operating system of claim 45, wherein the first valve actuator is biased with an actuator return member, wherein the actuator return member provides a motive force for automatically returning the first valve actuator to a starting position when not engaged by the valve controller and in the absence of the at least one temporary biasing structure.

47. The valve operating system of claim 46, wherein the at least one temporary biasing structure fixes the first medical fluid delivery line valve in a position opposite the starting position.

* * * * *